United States Patent
Ruvkun et al.

(10) Patent No.: US 11,738,056 B2
(45) Date of Patent: *Aug. 29, 2023

(54) COMPOSITIONS AND METHODS FOR IMPROVING MITOCHONDRIAL FUNCTION

(71) Applicant: THE GENERAL HOSPITAL CORPORATION, Boston, MA (US)

(72) Inventors: Gary Ruvkun, Newton, MA (US); J. Amaranath Govindan, Somerville, MA (US); Elamparithi Jayamani, Boston, MA (US)

(73) Assignee: THE GENERAL HOSPITAL CORPORATION, Boston, MA (US)

(*) Notice: Subject to any disclaimer, the term of this patent is extended or adjusted under 35 U.S.C. 154(b) by 338 days.

This patent is subject to a terminal disclaimer.

(21) Appl. No.: 17/196,271

(22) Filed: Mar. 9, 2021

(65) Prior Publication Data

US 2021/0213074 A1 Jul. 15, 2021

Related U.S. Application Data

(63) Continuation of application No. 16/293,789, filed on Mar. 6, 2019, now Pat. No. 10,973,860, which is a continuation of application No. PCT/US2019/014725, filed on Jan. 23, 2019.

(60) Provisional application No. 62/721,979, filed on Aug. 23, 2018, provisional application No. 62/620,641, filed on Jan. 23, 2018.

(51) Int. Cl.
| | |
|---|---|
| *A61K 35/74* | (2015.01) |
| *A61K 9/00* | (2006.01) |
| *C12N 9/04* | (2006.01) |
| *C12N 9/02* | (2006.01) |
| *C07K 14/195* | (2006.01) |
| *C12N 1/20* | (2006.01) |
| *A23L 33/135* | (2016.01) |
| *A23L 2/52* | (2006.01) |
| *A23K 10/18* | (2016.01) |

(52) U.S. Cl.
CPC ............ *A61K 35/74* (2013.01); *A23K 10/18* (2016.05); *A23L 2/52* (2013.01); *A23L 33/135* (2016.08); *A61K 9/0053* (2013.01); *A61K 9/0056* (2013.01); *C07K 14/195* (2013.01); *C12N 1/20* (2013.01); *C12N 9/0006* (2013.01); *C12N 9/0055* (2013.01); *C12N 9/0057* (2013.01); *C12Y 101/99* (2013.01); *C12Y 110/02002* (2013.01); *C12Y 110/0301* (2013.01); *A23V 2002/00* (2013.01); *C07K 2319/00* (2013.01); *C12N 2500/14* (2013.01); *C12N 2500/16* (2013.01); *C12N 2500/34* (2013.01)

(58) Field of Classification Search
None
See application file for complete search history.

(56) References Cited

U.S. PATENT DOCUMENTS

| | | | |
|---|---|---|---|
| 2012/0040014 | A1 | 2/2012 | Settineri et al. |
| 2019/0255124 | A1 | 8/2019 | Ruvkun et al. |

FOREIGN PATENT DOCUMENTS

| | | |
|---|---|---|
| CN | 1614007 A | 5/2005 |
| JP | 2006246701 A | 9/2006 |
| JP | 2007274907 A | 10/2007 |
| JP | 2013533309 A | 8/2013 |
| JP | 2015522256 A | 8/2015 |
| WO | 2013186570 A1 | 12/2013 |
| WO | 2019147652 A1 | 8/2019 |

OTHER PUBLICATIONS

Brenda (glucose 1-deyhdrogenase (PQQ, quinone), retrieved from the internet—https://www.brenda-enzymes.org/all_enzymes.php?ecno=1.1.5.2&table=Molecular_Weight, retrieved on Jul. 15, 2020.
Albers et al., "Mitochondrial dysfunction and oxidative stress in aging and neurodegenerative disease", In Advances in Dementia Research (pp. 133-154) (2000).
Amrit et al., "DAF-16 and TCER-1 Facilitate Adaptation to Germline Loss by Restoring Lipid Homeostasis and Repressing Reproductive Physiology in C. elegans", PLoS Genet 12(2) 21005788: 1-35 (2016).
Andersen et al., "Oxidative stress in neurodegeneration: cause or consequence?", Nature Reviews. Neuroscience, 10(7), S18-S25. (2004).
Back et al., "Exploring real-time in vivo redox biology of developing and aging Caenorhabditis elegans" Free Radic. Biol. Med. 52(5): 850-859 (2012).
Balaban et al., "Mitochondria, oxidants, and aging" Cell 120(4): 483-495 (2005).
Berendzen et al., "Neuroendocrine Coordination of Mitochondrial Stress Signaling and Proteostasis", Cell 166(6): 1553-1563.e10 (2016).
Braak et al., "Idiopathic Parkinson's disease: possible routes by which vulnerable neuronal types may be subject to neuroinvasion by an unknown pathogen", Journal of neural transmission 110(5): 517-536 (2003).
Braungart et al., "Caenorhabditis elegans MPP+ model of Parkinson's disease for high-throughput drug screenings", Neurodegener Dis, 1(4-5): 175-183 (2004).

(Continued)

*Primary Examiner* — Suzanne M Noakes
*Assistant Examiner* — Jae W Lee
(74) *Attorney, Agent, or Firm* — Nixon Peabody LLP; David S. Resnick; Mark J. FitzGerald

(57) ABSTRACT

Provided herein are methods and compositions comprising a bacterium or a metabolite thereof for enhancing mitochondrial and/or peroxisomal function.

17 Claims, 14 Drawing Sheets

Specification includes a Sequence Listing.

(56) References Cited

OTHER PUBLICATIONS

Brys et al., "Disruption of insulin signalling preserves bioenergetic competence of mitochondria in ageing Caenorhabditis elegans", BMC Biol. 8(1): 91 1-15 (2010).
Caldwell et al., "Traversing a wormhole to combat Parkinson's disease", Dis Model Mech 1(1): 32-36 (2008).
Cao et al., "Torsin-mediated protection from cellular stress in the dopaminergic neurons of Caenorhabditis elegans", J. Neurosci. 25(15): 3801-3812 (2005).
Cerosimo et al., "Pathological correlates of gastrointestinal dysfunction in Parkinson's disease", Neurobiology of disease 46(3): 559-564 (2012).
Chavez et al., Oxidative stress enzymes are required for DAF-16-mediated immunity due to generation of reactive oxygen species by Caenorhabditis elegans. Genetics 176(3): 1567-1577 (2007).
Chen et al., "Using C. elegans to discover therapeutic compounds for ageing-associated neurodegenerative diseases", Chem Cent J 9(1): 65 1-20 (2015).
Collier et al., "Ageing as a primary risk factor for Parkinson's disease: evidence from studies of non-human primates". Nature Reviews. Neuroscience, 12(6), 359-366 (2011).
Dancy et al., "Effects of the mitochondrial respiratory chain on longevity in C. elegans", Exp. Gerontol. 56: 245-255 (2014).
Devos et al., "Colonic inflammation in Parkinson's disease" Neurobiology of disease 50: 42-48 (2013).
Dias et al.,"The role of oxidative stress in Parkinson's disease", Journal of Parkinson's Disease, 3(4), 461-491 (2013).
Dingley et al., "Mitochondrial respiratory chain dysfunction variably increases oxidant stress in Caenorhabditis elegans", Mitochondrion 10(2): 125-136 (2010).
Durieux et al., "The cell-non-autonomous nature of electron transport chain-mediated longevity", Cell 144(1): 79-91 (2011).
Erkut et al., "The glyoxylate shunt is essential for desiccation tolerance in C. elegans and budding yeast", Elife 5, 12897 1-24 (2016).
Federico et al., "Mitochondria, oxidative stress and neurodegeneration", J. Neurol. Sci, 322(1-2): 254-262 (2012).
Feng et al., "Mitochondrial electron transport is a key determinant of life span in Caenorhabditis elegans" Dev. Cell 1 (5): 633-644 (2001).
Gruber et al., "Mitochondrial changes in ageing Caenorhabditis elegans—what do we learn from superoxide dismutase knockouts?", PLoS ONE 6(5): e19444 1-16 (2011).
Haigis et al., "The aging stress response" Mol. Cell 40(2) 333-344 (2010).
Harrington et al., "C. elegans as a model organism to investigate molecular pathways involved with Parkinson's disease", Dev. Dyn. 239: 1282-1295 (2010).
Hawkes et al., "Parkinson's disease: a dual-hit hypothesis", Neuropathology and applied neurobiology, 33(6): 599-614 (2007).
Hawkes et al., "Parkinson's disease: the dual hit theory revisited", Annals of the New York Academy of Sciences,1170(1) 615-622 (2009).
Hill et al., "The gastrointestinal tract microbiome and potential link to Alzheimer's disease" Front Neurol 5: 43 1-4 (2014).
Ishii et al., "A mutation in succinate dehydrogenase cytochrome b causes oxidative stress and ageing in nematodes", Nature 394(6694): 694-697 (1998).
Kayser et al., "GAS-1: a mitochondrial protein controls sensitivity to volatile anesthetics in the nematode Caenorhabditis elegans" Anesthesiology 90(2): 545-554 (1999).
Kuo et al., "Extensive enteric nervous system abnormalities in mice transgenic for artificial chromosomes containing Parkinson disease-associated α-synuclein gene mutations precede central nervous system changes", Human molecular genetics 19(9): 1633-1650 (2010).
Lagido et al., "A Screenable In Vivo Assay for Mitochondrial Modulators Using Transgenic Bioluminescent Caenorhabditis elegans", J Vis Exp e53083-e53083 1-12 (2015). doi:10.3791/53083.

Lakso et al., "Dopaminergic neuronal loss and motor deficits in Caenorhabditis elegans overexpressing human alpha-synuclein" J Neurochem 86(1): 165-172 (2003).
Lee et al., "Gain-of-Function Alleles in Caenorhabditis elegans Nuclear Hormone Receptor nhr-49 Are Functionally Distinct" PLoS ONE 11(9): e0162708 1-24 (2016).
Link et al., "C. elegans models of age-associated neurodegenerative diseases: lessons from transgenic worm models of Alzheimer's disease", Exp. Gerontol. 41(10): 1007-1013 (2006).
Link et al., "The beta amyloid peptide can act as a modular aggregation domain", Neurobiol. Dis. 32(3): 420-425 (2008).
Lublin et al., Alzheimer's disease drug discovery: in vivo screening using Caenorhabditis elegans as a model for β-amyloid peptide-induced toxicity. Drug Discov Today Technol 10(1): e115-119 (2013).
McColl et al., "Utility of an improved model of amyloid-beta ($A\beta_{1-42}$) toxicity in Caenorhabditis elegans for drug screening for Alzheimer's disease", Mol Neurodegener 7: 57 1-9(2012).
McCormack et al., "Pharmacologic targeting of sirtuin and PPAR signaling improves longevity and mitochondrial physiology in respiratory chain complex I mutant Caenorhabditis elegans", Mitochondrion 22, 45-59 (2015).
Meyer et al., "Effects of membrane-bound glucose dehydrogenase overproduction on the respitory chain of Gluconobacteroxydans" Appl. Microbiol Biotechnol 97(8): 3457-3466 (2013).
Moreira et al., "Mitochondrial dysfunction is a trigger of Alzheimer's disease pathophysiology", Biochim. Biophys. Acta 1802(1): 2-10 (2010).
Mukherjee et al., Gut dysfunction in Parkinson's disease. World Journal of Gastroenterology, 22(25), 5742-5752 (2016).
Muller et al., "Mitochondrial dysfunction: common final pathway in brain aging and Alzheimer's disease—therapeutic aspects", Mol Neurobiol. 41(2-3): 159-171 (2010).
Nass et al., "Neurotoxin-induced degeneration of dopamine neurons in Caenorhabditis elegans", Proceedings of the National Academy of Sciences 99(5): 3264 3269 (2002).
Ng et al., "The mitochondria-targeted antioxidant MitoQ extends lifespan and improves healthspan of a transgenic Caenorhabditis elegans model of Alzheimer disease" Free Radic. Biol. Med 71, 390-401 (2014).
Palikaras et al., Intracellular Assessment of ATP Levels in Caenorhabditis elegans. Bio Protoc 6(23):e22048 1-9 (2016).
Pellegrini et al., "Intestinal dysfunction in Parkinson's disease: Lessons learned from translational studies and experimental models", Neurogastroenterology & Motility, 28(12), 1781-1791 (2016).
Ratnappan et al., "Germline signals deploy NHR-49 to modulate fatty-acid β-oxidation and desaturation in somatic tissues of C. elegans", PLoS Genet 10(12), e1004829 1-20 (2014).
Rauthan et al., "A Mutation in Caenorhabditis elegans NDUF-7 Activates the Mitochondrial Stress Response and Prolongs Lifespan via ROS and CED-4", G3 (Bethesda) 5(8):1639-1648 (2015).
Gao et al. "Characterization of a group of pyrroloquinoline quinone-dependent dehydrogenases that are involved in the conversion of L-sorbose to 2-Keto-L-gulonic acid in Ketogulonicigenium vulgare WSH-001." Biotechnology Progress 29(6): 1398-1404 (2013).
Misra et al. "Pyrroloquinoline-quinone and its versatile roles in biological processes." Journal of Biosciences 37(2): 313-325 (2012).
Stites et al. "Physiological importance of quinoenzymes and the O-quinone family of cofactors." The Journal of Nutrition 130(4): 719-727 (2000).
Rolland et al., "The BCL-2-like protein CED-9 of C. elegans promotes FZO-1/Mfn1,2- and EAT-3/Opa1-dependent mitochondrial fusion" J. Cell Biol. 186(4): 525-540 (2009).
Shao et al., "Neuropeptide signals cell non-autonomous mitochondrial unfolded protein response" Cell Res 26(11): 1182-1196 (2016).
Sorrentino et al., Enhancing mitochondrial proteostasis reduces amyloid-β proteotoxicity. Nature 552(7684): 187-193 (2017).
TEKnova "Broth Glucose 1%" Ampicillin-50 (2013).
Van Gilst et al., "Nuclear hormone receptor NHR-49 controls fat consumption and fatty acid composition in C. elegans", PLoS Biol 3(2), e53 0301-0312 (2005).

(56) References Cited

OTHER PUBLICATIONS

Van Ham et al. "C. elegans model identifies genetic modifiers of alpha-synuclein inclusion formation during aging." PLoS Genet 4(3), e1000027 1-11 (2008).

Van Schie et al., "Glucose-dehydrogenase-mediated solute transport and ATP synthesis in Acinetobacter calcoaceticus" Journal of General Microbiology 133(12): 3427-3435 (1987).

Ved et al., "Similar patterns of mitochondrial vulnerability and rescue induced by genetic modification of alpha-synuclein, parkin, and DJ-1 in Caenorhabditis elegans", J Biol Chem 280(52): 42655-42668 (2005).

Winklhofer et al., "Mitochondrial dysfunction in Parkinson's disease", Biochim. Biophys. Acta 1802(1): 29-44 (2010).

Zhang et al., "Genetic and dietary regulation of lipid droplet expansion in Caenorhabditis elegans" Proc Natl Acad Sci U S A 107(10): 4640-4645 (2010).

Zhou et al., "Caenorhabditis elegans neuron degeneration and mitochondrial suppression caused by selected environmental chemicals", Int J Biochem Mol Biol 4(4): 191-200 (2013).

Zubovych et al., "Mitochondrial dysfunction confers resistance to multiple drugs in Caenorhabditis elegans" Mol Biol Cell 21(6:) 956-969 (2010).

Hrnjez et al. "The biological activity of fermented dairy products obtained by kombucha and conventional starter cultures during storage." journal of functional foods 10: 336-345 (2014).

Uniprot (a membrane-bound PQQ-dependent glucose dehydrogenase (mGDH), retrieved from the internet <<https://www.uniprot.org/uniprot/s6D688>>, retrieved on Jan. 7, 2020).

Uniprot (a ubiquionol-cytochrome c reductase iron-sulfur subunit, retrieved from the internet <<https://www.uniprot.org/uniprot/S6D5X7, retrieved on Jan. 7, 2020).

Uniprot (a TonB-dependent receptor, retrieved from the internet <<https://uniprot.org/uniprot/A0A149V8E0>>, retrieved on Jan. 7, 2020).

Uniprot (a carbon-nitrogen hydrolase, retrieved from the Internet <<http://www.uniprot.org/uniprot/S6CY88>>, retrieved on Jan. 7, 2020).

Uniprot (a ubiquinol oxidase subunit II, retrieved from the Internet <<http://www.uniprot.org/uniprot/P50653>>, retrieved on Jan. 7, 2020).

International Search Report and Written Opinion, PCT/US2019/014725,1-6, dated Sep. 7, 2019.

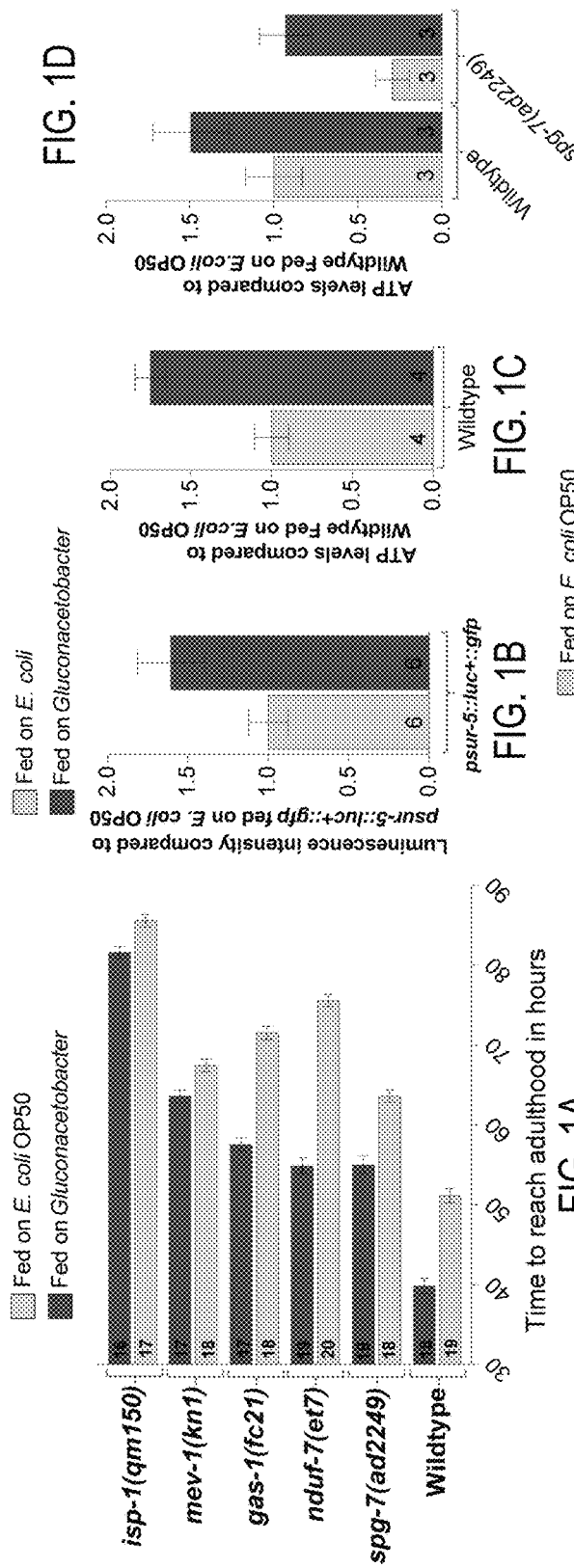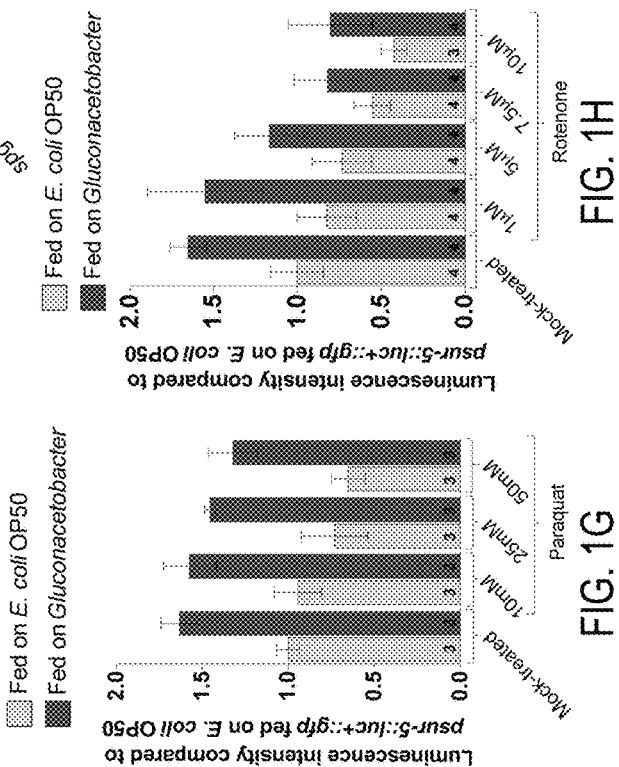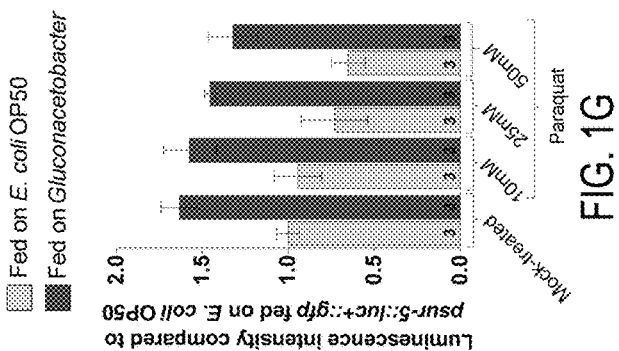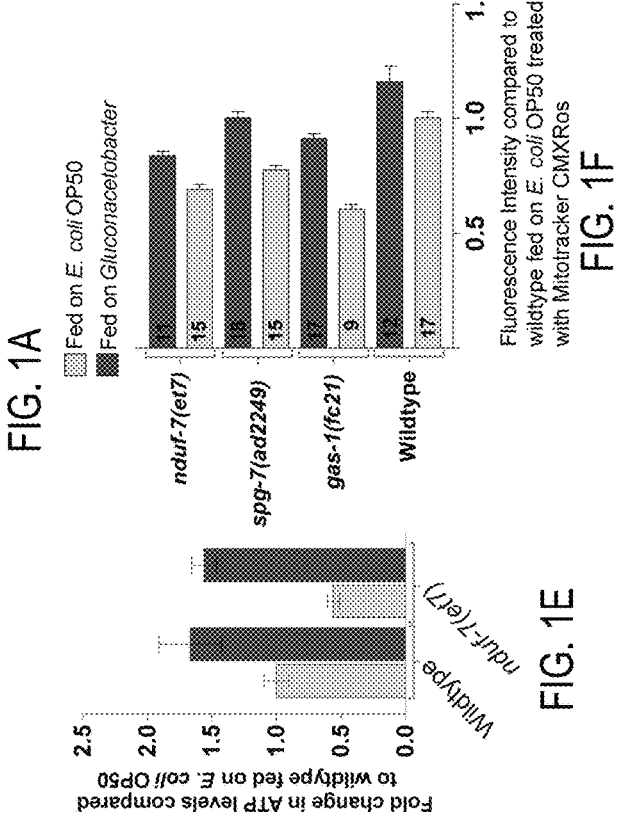

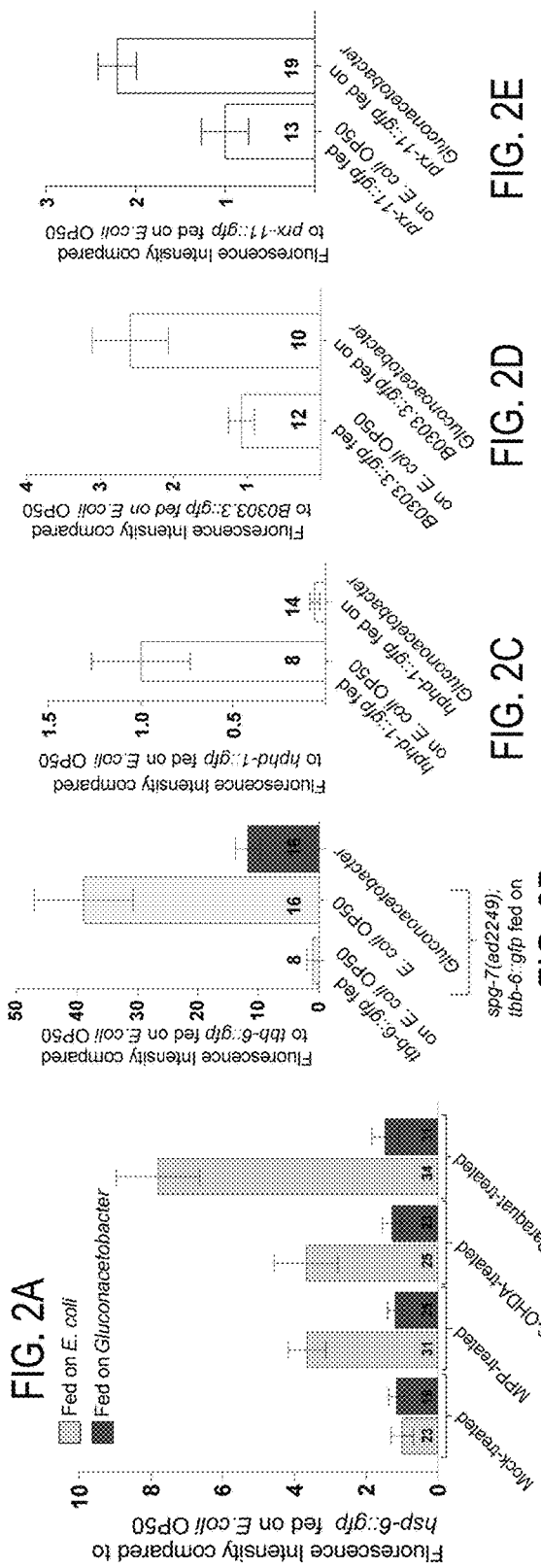
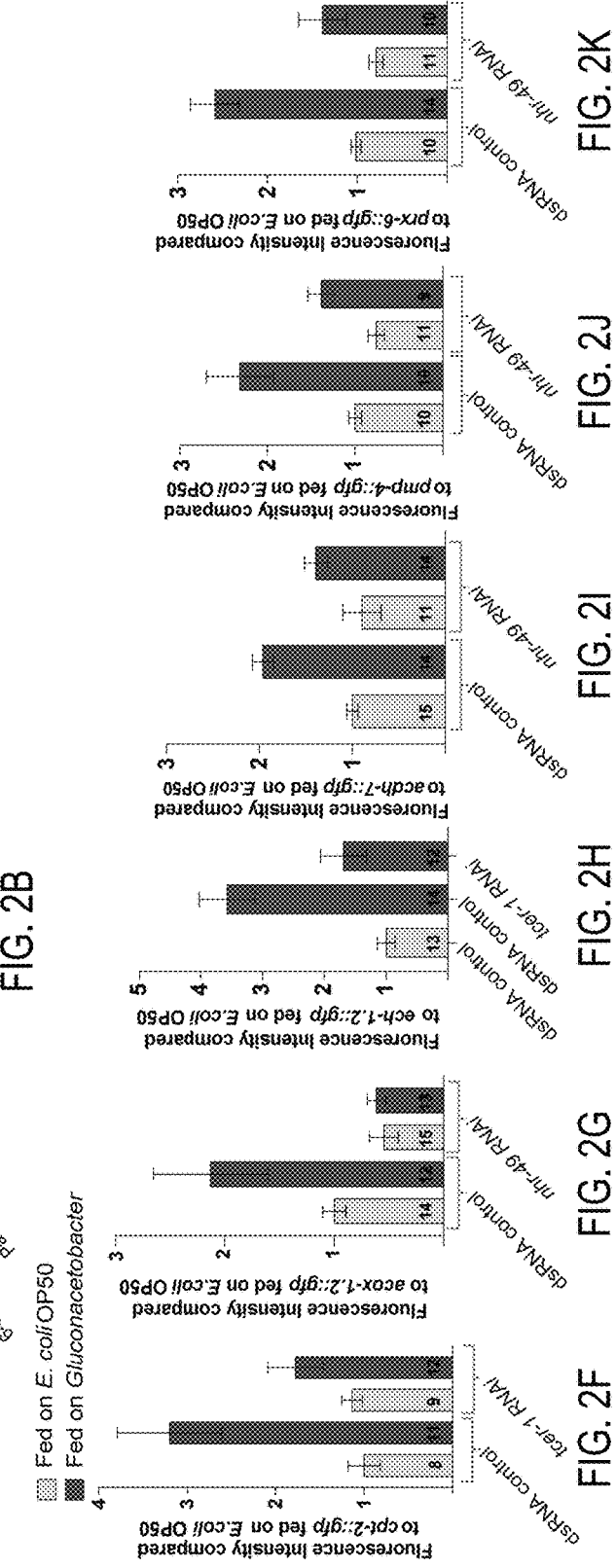

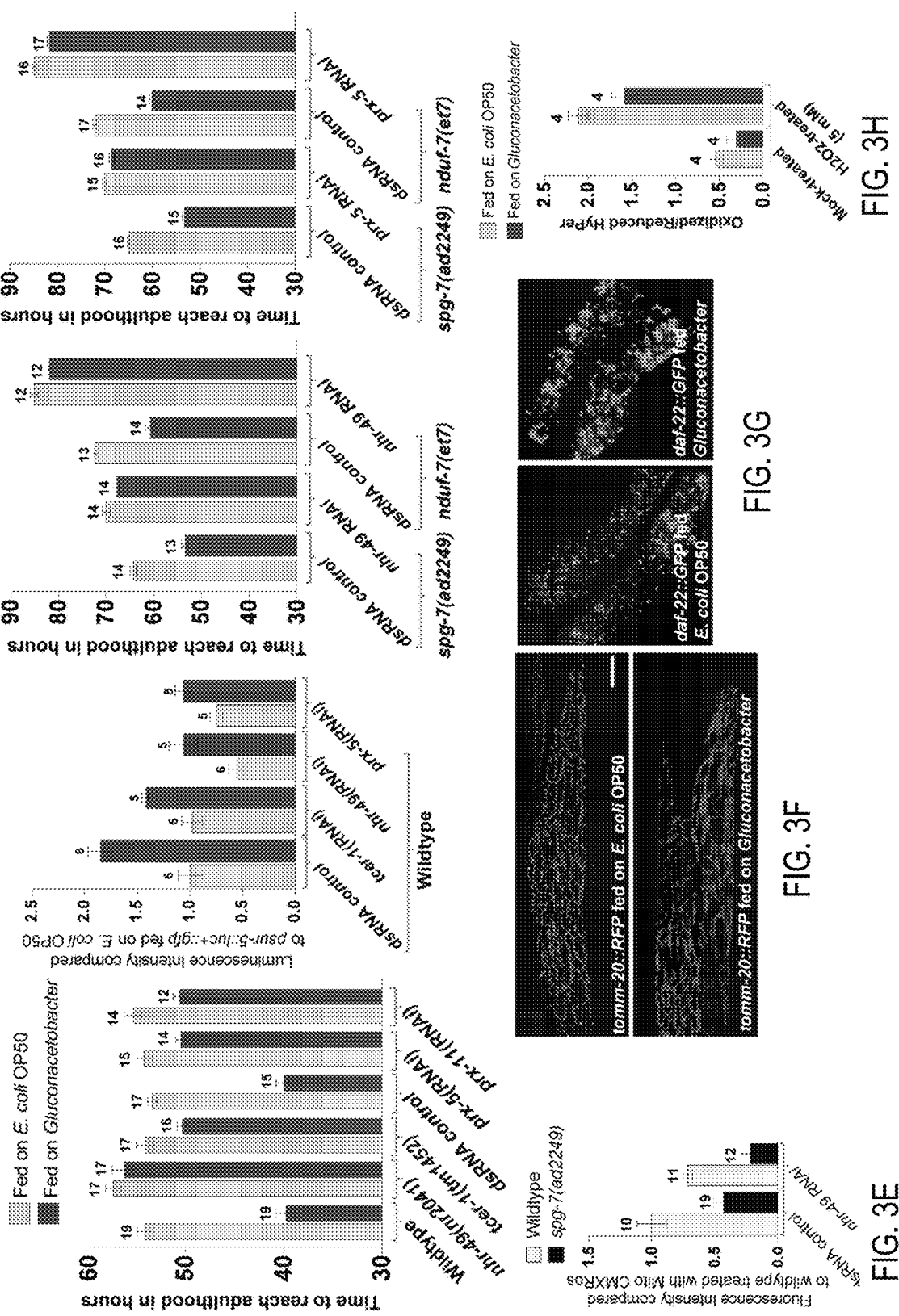

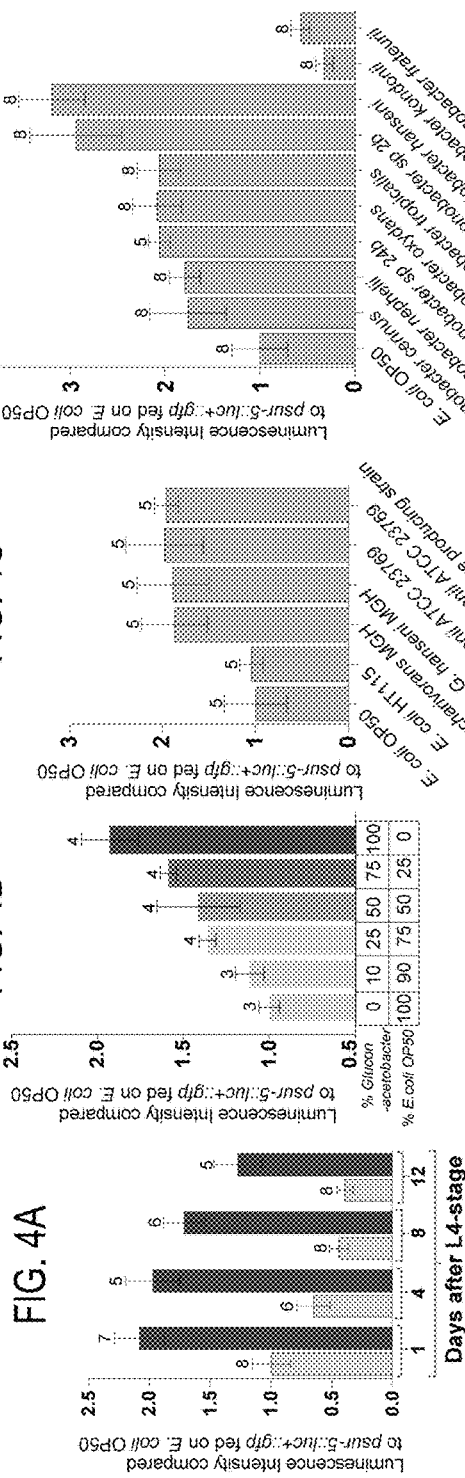
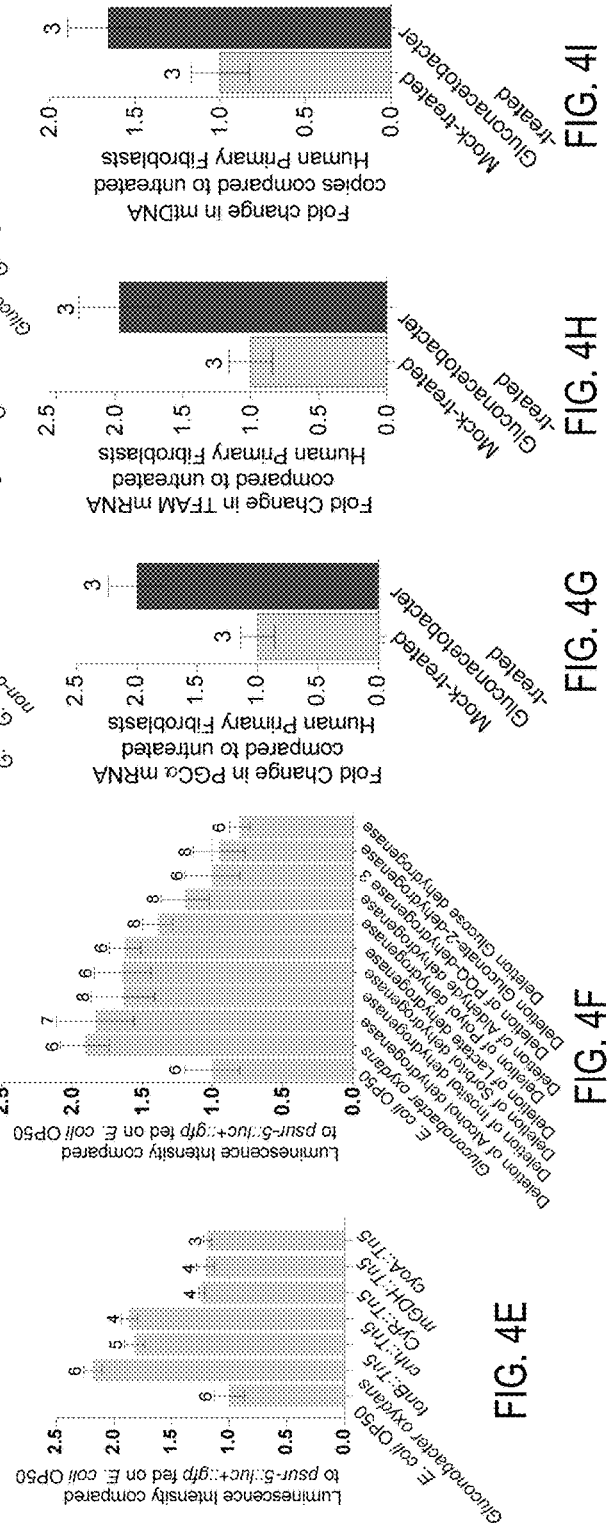

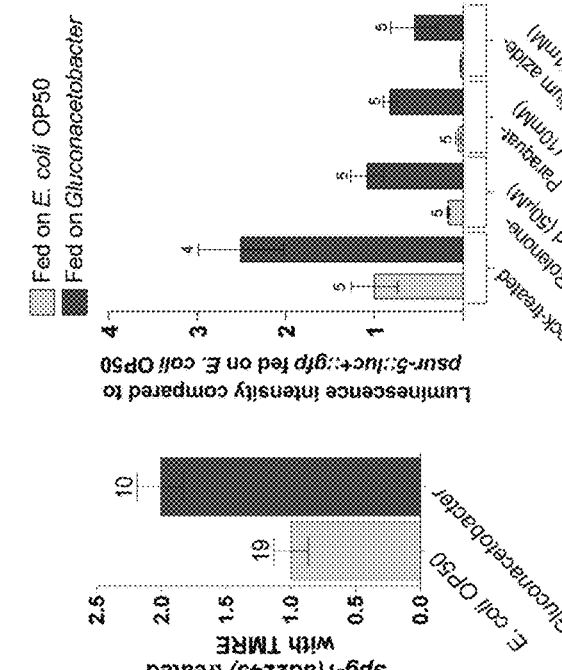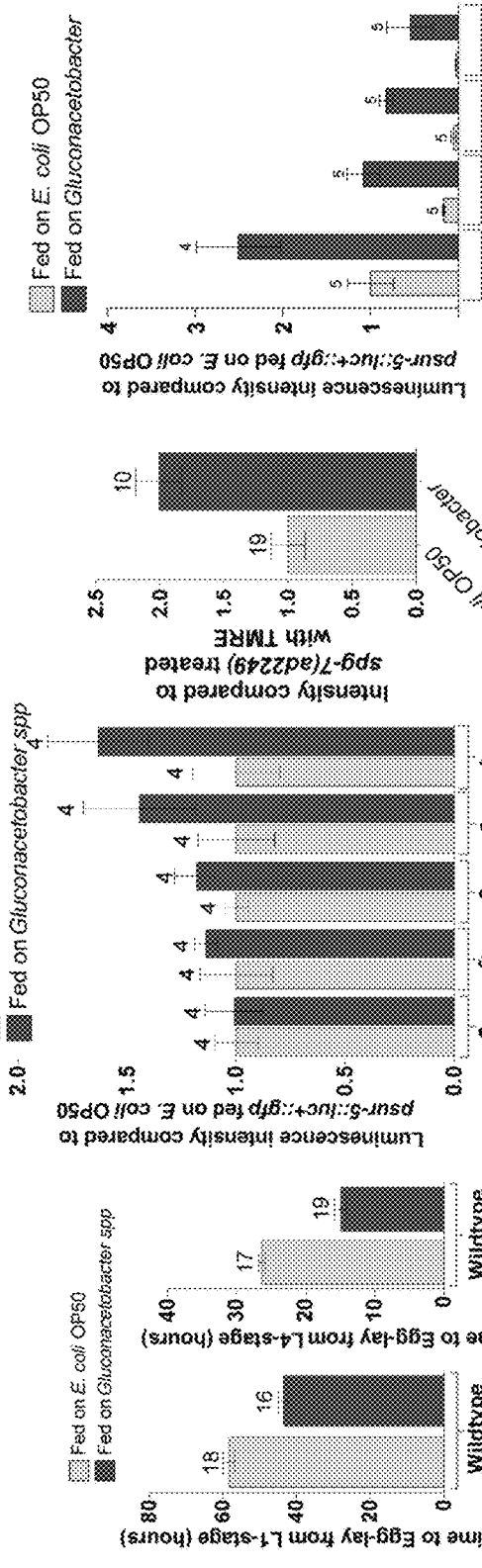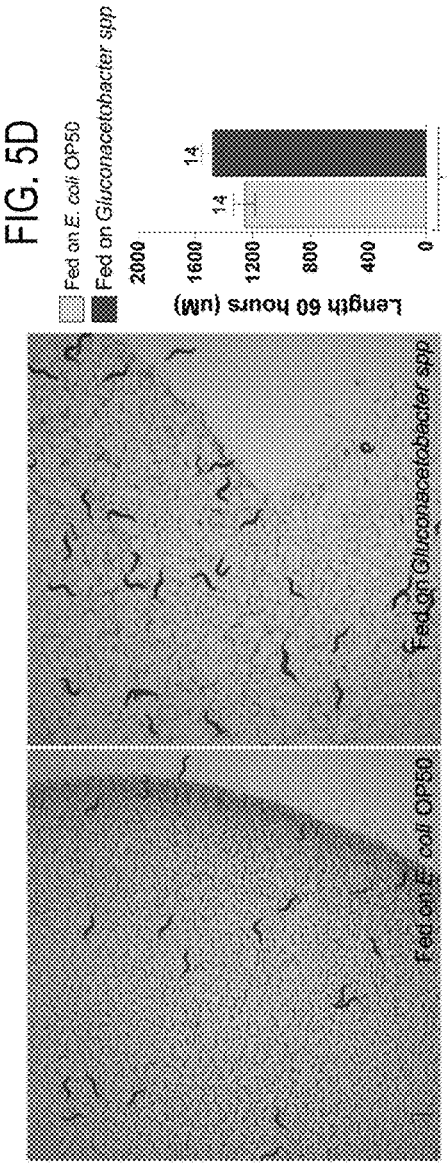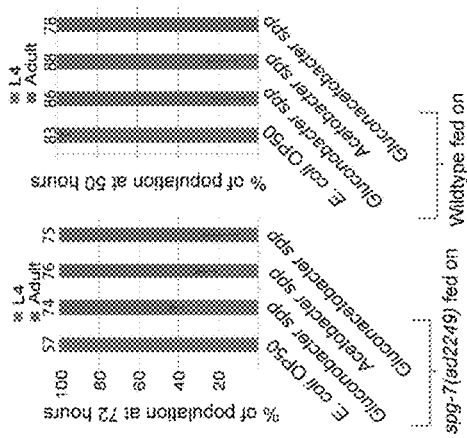

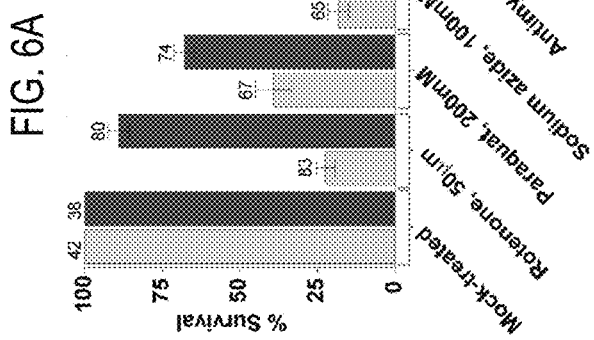
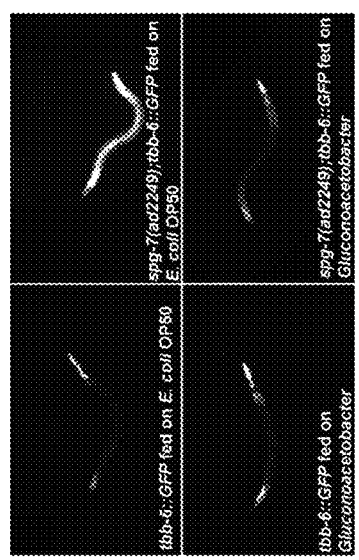
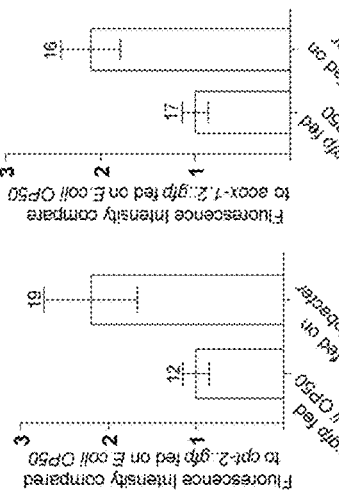
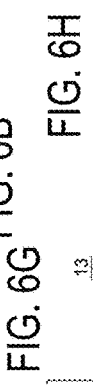
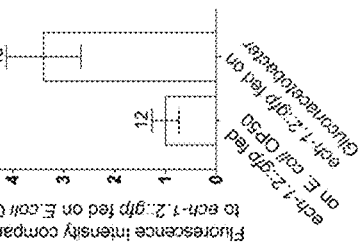
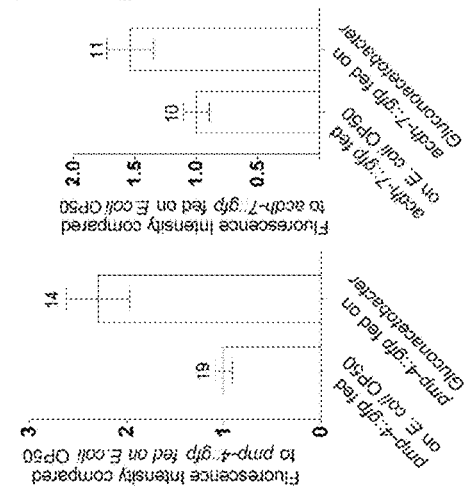

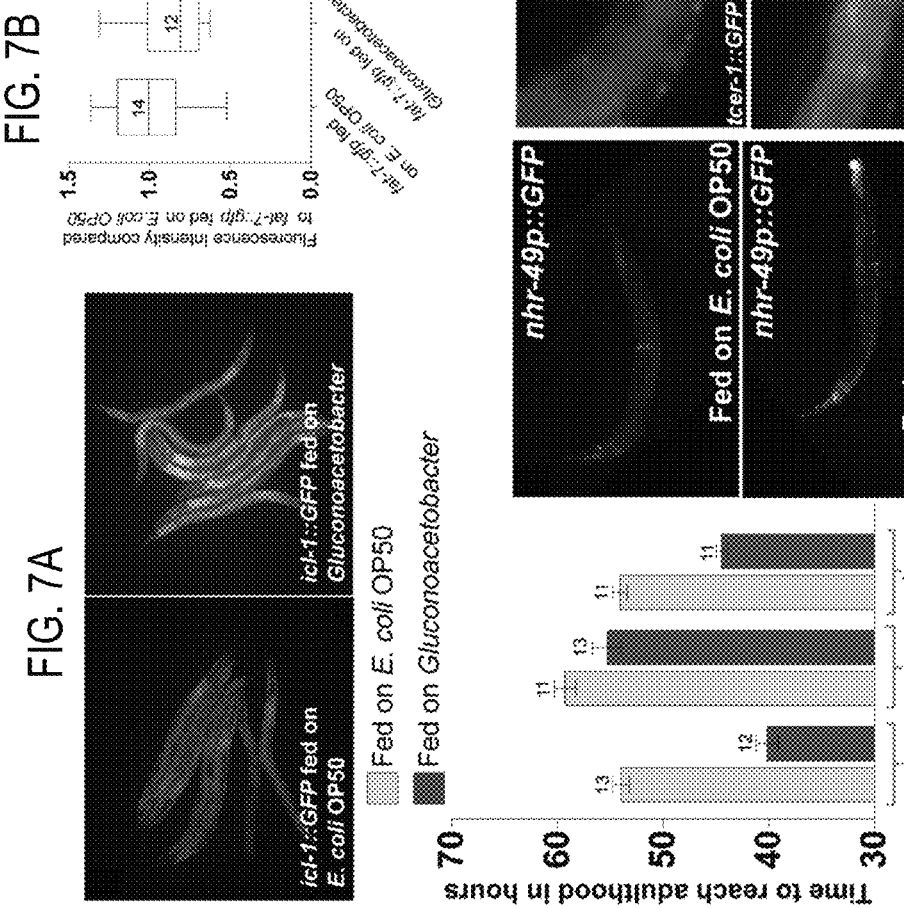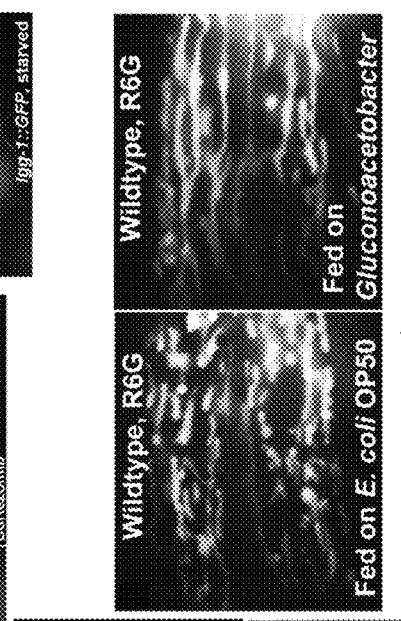

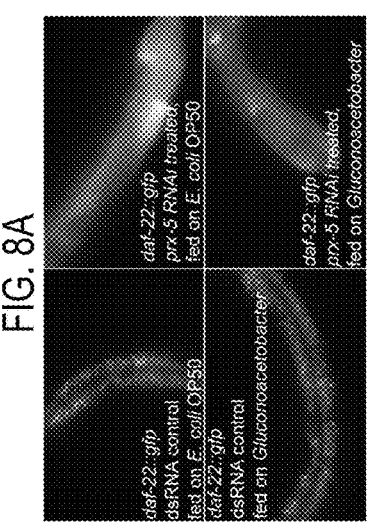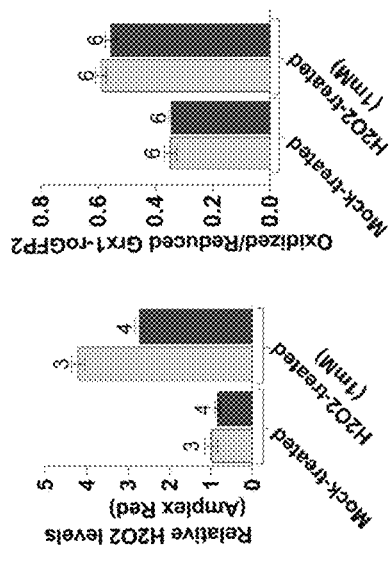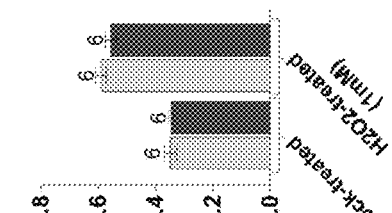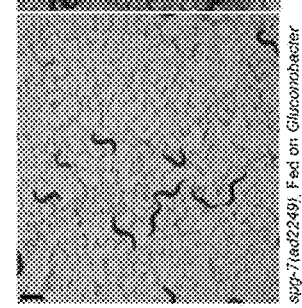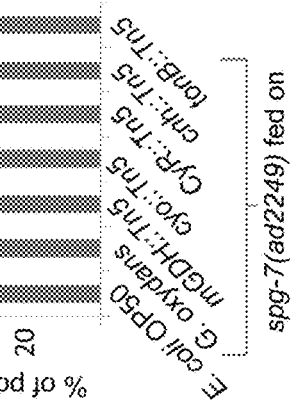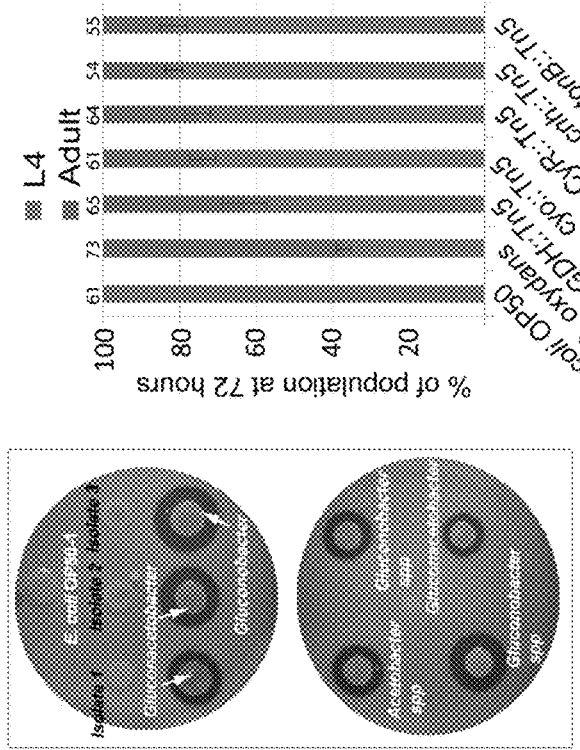

SEQUENCE LISTING

<160> NUMBER OF SEQ ID NOS: 44

<210> SEQ ID NO 1
<211> LENGTH: 2427
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1

```
atgagcacaa tttcccggcc agggctctgg gccctgataa cggccgcggt attcgcgctt        60
tgcggcgcga tccttaccgt tggcggcgca tgggtcgctg ccatcggcgg ccctctttat       120
tatgtcatcc ttggcctggc acttctcgcc acggctttcc tctcattccg gcgcaatccg       180
gctgccctct atctgttcgc agtcgtcgtc ttcggaacgg tcatctggga actcaccgtt       240
gtcggtctcg acatctgggc cctgatcccg cgctcggaca tcgtcatcat cctcggcatc       300
tggctgctgc tgccgttcgt ctcgcgccag atcggtggca cgcggacgac cgtcctgccg       360
ctcgccggcg ccgttggcgt tgcggttctg gccctgttcg ccagcctctt caccgacccg       420
catgacatca gcggcgaact gccgacgcag atcgcaaacg cctcccccgc cgacccggac       480
aacgttccgg ccagcgagtg gcacgcttat ggtcgtacgc aggccggtga ccgctggtcc       540
ccgctgaacc agatcaatgc gacgaacgtc agcaacctca aggtcgcatg gcatatccac       600
accaaggata tgatgaactc caacgacccg ggcgaagcga cgaacgaagc gacgccgatc       660
gagttcaaca acacgcttta tatgtgctca ctgcatcaga agctgtttgc ggttgatggt       720
```

-continued

```
gccaccggca acgtcaagtg ggtctacgat ccgaagctcc agatcaaccc tggcttccag      780
catctgacct gccgtggcgt cagcttccac gaaacgccgg ccaatgccat ggattccgat      840
ggcaatcctg ctccgacgga ctgcgccaag cgcatcatcc tgccggtcaa tgatggccgt      900
ctggttgaag tcgatgccga cacgggcaag acctgctccg gcttcggcaa caatggcgag      960
atcgacctgc gcgttccgaa ccagccttac gacgcctg gccagtacga gccgacgtcc       1020
ccgccggtca tcacagacaa gctgatcatc gccaacagcg ccatcaccga taacggttcg     1080
gtcaagcagg cttcgggcgc cacgcaggca ttcgacgtct acaccggcaa gcgcgtctgg     1140
gtgttcgatg cgtccaaccc ggatccgaac cagcttccgg atgagagcca ccctgtcttc    1200
cacccgaact cgccaaactc ctggatcgtg tcgtcctacg acgccaacct gaacctcgtg    1260
tacatcccga tgggcgtggg gactcccgac cagtgggggcg gtgaccgcac gaaggattcc    1320
gagcgtttcg ctccgggtat cgttgcgctg aacgccgata cgggcaagct cgcctggttc    1380
taccagaccg ttcatcacga tctgtgggac atggacgttc cgtcccagcc gagcctcgtg    1440
gatgtgacac agaaggacgg cacgcttgtt ccggccatct acgctccgac caagaccggc   1500
gacattttcg tcctcgaccg tcgtaccggc aaggaaatcg tcccggctcc ggaaaccccg   1560
gttccccagg gtgctgctcc gggtgaccac accagcccga cccagccgat gtcgcagctg   1620
accctgcgtc cgaagaaccc gctgaacgac tccgatatct ggggcggcac gatcttcgac  1680
cagatgttct gcagcatcta tttccacacc ctccgctacg aaggcccctt cacgccgccg  1740
tcgctcaagg gctcgctcat cttcccgggt gatctgggaa tgttcgaatg gggtggtctg   1800
gccgtcgatc cgcagcgtca ggtggctttc gccaacccga tttccctgcc gttcgtctct   1860
cagcttgttc cccgcggacc gggcaacccg ctctggcctg aaggaaatgc caagggcacg   1920
ggtggtgaaa ccggcctgca gcacaactat ggcatcccgt atgccgtcaa cctgcatccg   1980
ttcctggatc cggtgctgct gccgttcggc atcaagatgc cgtgccgcac gccgccctgg  2040
ggctatgtcg ccggtattga cctgaagacc aacaaggtcg tctggcagca ccgcaacggc  2100
accctgcgtg actcgatgta tggcagctcc ctgccgatcc gctgccgcc gatcaagatc   2160
ggtgtcccga gcctcggtgg cccgctctcc acggctggca atctcggctt cctgacggcg  2220
tccatggatt actacatccg tgcgtacaac ctgacgacgg gcaaggtgct gtggcaggac   2280
cgtctgccgg ctggtgctca ggcaacgccg atcacctatg ccatcaacgg caagcagtac   2340
atcgtgacct atgcaggcgg acacaactcg ttcccgaccc gcatgggcga cgacatcatc   2400
gcctacgccc tgcccgatca gaaatga                                          2427
```

<210> SEQ ID NO 2
<211> LENGTH: 808
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 2

```
Met Ser Thr Ile Ser Arg Pro Gly Leu Trp Ala Leu Ile Thr Ala Ala
1               5                   10                  15

Val Phe Ala Leu Cys Gly Ala Ile Leu Thr Val Gly Gly Ala Trp Val
            20                  25                  30

Ala Ala Ile Gly Gly Pro Leu Tyr Tyr Val Ile Leu Gly Leu Ala Leu
        35                  40                  45
```

```
Leu Ala Thr Ala Phe Leu Ser Phe Arg Arg Asn Pro Ala Ala Leu Tyr
 50                  55                  60

Leu Phe Ala Val Val Phe Gly Thr Val Ile Trp Glu Leu Thr Val
 65              70                  75                  80

Val Gly Leu Asp Ile Trp Ala Leu Ile Pro Arg Ser Asp Ile Val Ile
             85                  90                  95

Ile Leu Gly Ile Trp Leu Leu Leu Pro Phe Val Ser Arg Gln Ile Gly
             100                 105                 110

Gly Thr Arg Thr Thr Val Leu Pro Leu Ala Gly Ala Val Gly Val Ala
         115                 120                 125

Val Leu Ala Leu Phe Ala Ser Leu Phe Thr Asp Pro His Asp Ile Ser
 130                 135                 140

Gly Glu Leu Pro Thr Gln Ile Ala Asn Ala Ser Pro Ala Asp Pro Asp
 145                 150                 155                 160

Asn Val Pro Ala Ser Glu Trp His Ala Tyr Gly Arg Thr Gln Ala Gly
                 165                 170                 175

Asp Arg Trp Ser Pro Leu Asn Gln Ile Asn Ala Thr Asn Val Ser Asn
             180                 185                 190

Leu Lys Val Ala Trp His Ile His Thr Lys Asp Met Met Asn Ser Asn
         195                 200                 205

Asp Pro Gly Glu Ala Thr Asn Glu Ala Thr Pro Ile Glu Phe Asn Asn
 210                 215                 220

Thr Leu Tyr Met Cys Ser Leu His Gln Lys Leu Phe Ala Val Asp Gly
 225                 230                 235                 240

Ala Thr Gly Asn Val Lys Trp Val Tyr Asp Pro Lys Leu Gln Ile Asn
                 245                 250                 255

Pro Gly Phe Gln His Leu Thr Cys Arg Gly Val Ser Phe His Glu Thr
             260                 265                 270

Pro Ala Asn Ala Met Asp Ser Asp Gly Asn Pro Ala Pro Thr Asp Cys
         275                 280                 285

Ala Lys Arg Ile Ile Leu Pro Val Asn Asp Gly Arg Leu Val Glu Val
     290                 295                 300

Asp Ala Asp Thr Gly Lys Thr Cys Ser Gly Phe Gly Asn Asn Gly Glu
 305                 310                 315                 320

Ile Asp Leu Arg Val Pro Asn Gln Pro Tyr Thr Thr Pro Gly Gln Tyr
                 325                 330                 335

Glu Pro Thr Ser Pro Val Ile Thr Asp Lys Leu Ile Ile Ala Asn
             340                 345                 350

Ser Ala Ile Thr Asp Asn Gly Ser Val Lys Gln Ala Ser Gly Ala Thr
         355                 360                 365

Gln Ala Phe Asp Val Tyr Thr Gly Lys Arg Val Trp Val Phe Asp Ala
     370                 375                 380

Ser Asn Pro Asp Pro Asn Gln Leu Pro Asp Glu Ser His Pro Val Phe
 385                 390                 395                 400

His Pro Asn Ser Pro Asn Ser Trp Ile Val Ser Ser Tyr Asp Ala Asn
                 405                 410                 415

Leu Asn Leu Val Tyr Ile Pro Met Gly Val Gly Thr Pro Asp Gln Trp
             420                 425                 430

Gly Gly Asp Arg Thr Lys Asp Ser Glu Arg Phe Ala Pro Gly Ile Val
         435                 440                 445

Ala Leu Asn Ala Asp Thr Gly Lys Leu Ala Trp Phe Tyr Gln Thr Val
 450                 455                 460

His His Asp Leu Trp Asp Met Asp Val Pro Ser Gln Pro Ser Leu Val
```

```
                465                 470                 475                 480
        Asp Val Thr Gln Lys Asp Gly Thr Leu Val Pro Ala Ile Tyr Ala Pro
                        485                 490                 495
        Thr Lys Thr Gly Asp Ile Phe Val Leu Asp Arg Arg Thr Gly Lys Glu
                        500                 505                 510
        Ile Val Pro Ala Pro Glu Thr Pro Val Pro Gln Gly Ala Ala Pro Gly
                        515                 520                 525
        Asp His Thr Ser Pro Thr Gln Pro Met Ser Gln Leu Thr Leu Arg Pro
                        530                 535                 540
        Lys Asn Pro Leu Asn Asp Ser Asp Ile Trp Gly Thr Ile Phe Asp
        545                 550                 555                 560
        Gln Met Phe Cys Ser Ile Tyr Phe His Thr Leu Arg Tyr Glu Gly Pro
                        565                 570                 575
        Phe Thr Pro Pro Ser Leu Lys Gly Ser Leu Ile Phe Pro Gly Asp Leu
                        580                 585                 590
        Gly Met Phe Glu Trp Gly Gly Leu Ala Val Asp Pro Gln Arg Gln Val
                        595                 600                 605
        Ala Phe Ala Asn Pro Ile Ser Leu Pro Phe Val Ser Gln Leu Val Pro
                        610                 615                 620
        Arg Gly Pro Gly Asn Pro Leu Trp Pro Glu Gly Asn Ala Lys Gly Thr
        625                 630                 635                 640
        Gly Gly Glu Thr Gly Leu Gln His Asn Tyr Gly Ile Pro Tyr Ala Val
                        645                 650                 655
        Asn Leu His Pro Phe Leu Asp Pro Val Leu Leu Pro Phe Gly Ile Lys
                        660                 665                 670
        Met Pro Cys Arg Thr Pro Pro Trp Gly Tyr Val Ala Gly Ile Asp Leu
                        675                 680                 685
        Lys Thr Asn Lys Val Val Trp Gln His Arg Asn Gly Thr Leu Arg Asp
                        690                 695                 700
        Ser Met Tyr Gly Ser Ser Leu Pro Ile Pro Leu Pro Pro Ile Lys Ile
        705                 710                 715                 720
        Gly Val Pro Ser Leu Gly Gly Pro Leu Ser Thr Ala Gly Asn Leu Gly
                        725                 730                 735
        Phe Leu Thr Ala Ser Met Asp Tyr Tyr Ile Arg Ala Tyr Asn Leu Thr
                        740                 745                 750
        Thr Gly Lys Val Leu Trp Gln Asp Arg Leu Pro Ala Gly Ala Gln Ala
                        755                 760                 765
        Thr Pro Ile Thr Tyr Ala Ile Asn Gly Lys Gln Tyr Ile Val Thr Tyr
                        770                 775                 780
        Ala Gly Gly His Asn Ser Phe Pro Thr Arg Met Gly Asp Asp Ile Ile
        785                 790                 795                 800
        Ala Tyr Ala Leu Pro Asp Gln Lys
                        805

<210> SEQ ID NO 3
<211> LENGTH: 657
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3
atgacccagg acgatgcctc tctcatttct gatccaacgt cttccagaca ggaggagggg     60
tctcgccgca gggatgtgct ggcaacggta acagttgcca tgggatgtgc aggcgcgtgt    120
```

```
gctgtggcct atcctttct ggacagcctg aatgggacgc gcgccaatca tgtcggggag      180
agcgacatcc tggacgtgga tctctctacc ctcaaagccg ccagcagat tgttgtgaca      240 tggcggggt ggcccgtgtt cgtgcagaga agaacgccag aaatgctgaa aacgcttcag     300
gatccggcaa tcctgcagaa actacgagat cctgagtcct gcattttcca acaacccaaa    360
gacgcaacaa actggcatcg ttccgtcagc ccgatatcg gcgtcatgat tgggatctgt     420
acccatctcg gctgcgtgcc gactttcgac gccccgacgc aggcagaacc tgccgggaaa    480
tacctctgcc cctgtcatgg ttcacagttt gacagtgcag gccgcgccta caggaacgcc    540
cctgcaccat acaatctgcc ggttccgccc gtgacaatga tttccgatac gcatctgcga    600
attggagaaa gcaaaaacga tcctgacttt gatattgcta acatccagca gatctga       657
```

<210> SEQ ID NO 4
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Met Thr Gln Asp Asp Ala Ser Leu Ile Ser Asp Pro Thr Ser Ser Arg
1               5                   10                  15

Gln Glu Glu Gly Ser Arg Arg Asp Val Leu Ala Thr Val Thr Val
            20                  25                  30

Ala Met Gly Cys Ala Gly Ala Cys Ala Val Ala Tyr Pro Phe Leu Asp
        35                  40                  45

Ser Leu Asn Gly Thr Arg Ala Asn His Val Gly Glu Ser Asp Ile Leu
    50                  55                  60

Asp Val Asp Leu Ser Thr Leu Lys Ala Gly Gln Gln Ile Val Val Thr
65                  70                  75                  80

Trp Arg Gly Trp Pro Val Phe Val Gln Arg Arg Thr Pro Glu Met Leu
                85                  90                  95

Lys Thr Leu Gln Asp Pro Ala Ile Leu Gln Lys Leu Arg Asp Pro Glu
            100                 105                 110

Ser Cys Ile Phe Gln Gln Pro Lys Asp Ala Thr Asn Trp His Arg Ser
        115                 120                 125

Val Ser Pro Asp Ile Gly Val Met Ile Gly Ile Cys Thr His Leu Gly
    130                 135                 140

Cys Val Pro Thr Phe Asp Ala Pro Thr Gln Ala Glu Pro Ala Gly Lys
145                 150                 155                 160

Tyr Leu Cys Pro Cys His Gly Ser Gln Phe Asp Ser Ala Gly Arg Ala
                165                 170                 175

Tyr Arg Asn Ala Pro Ala Pro Tyr Asn Leu Pro Val Pro Pro Val Thr
            180                 185                 190

Met Ile Ser Asp Thr His Leu Arg Ile Gly Glu Ser Lys Asn Asp Pro
        195                 200                 205

Asp Phe Asp Ile Ala Asn Ile Gln Gln Ile
    210                 215

<210> SEQ ID NO 5
<211> LENGTH: 2940
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 5

| | | | | | |
|---|---|---|---|---|---|
| atgatcgtat | cgcgtcgcaa | tacgttactt | tgcgcatcgg | tgctggggat | ggggggcgctt | 60 |
| tcgagcgttg | ctcatgcggc | aaccgaaagc | actcacacgt | cctcacatgt | gcgccacaag | 120 |
| actgtgactc | atggtccggt | gcgttctgct | gcgacgcctg | caacaacagc | tccggtctcg | 180 |
| gtagctcgtc | cggtggcagc | tccgcagttt | tctgcacctg | tagcggtcaa | ccggtcccat | 240 |
| gccgttcgtt | ccattgattc | cggaacgcag | gaaagcgttg | tggtcacggg | gtcggctctg | 300 |
| agcacgtcta | acaatcagaa | cgcgaacccg | gtccagatcg | tgaccagcaa | gcagatcgag | 360 |
| cagactggca | tcaacactct | gggtgattac | ctgcagcgcc | tgccgtctgt | cggttcttcg | 420 |
| ggtacgacga | acagccaaac | caacaatacg | gcgggtgttt | cttgcacgga | tatccgtaac | 480 |
| cttggcaaaa | gccgtgttct | ggttctgatt | gatggcaagc | gtgcagcaat | tgacggctcg | 540 |
| tcaagctgct | ttgatctgaa | caccatcaat | attcaccagg | tggcgagtgt | cgaaatcctc | 600 |
| aaggatggtg | gttctgagct | gtatggtgct | gatgccgttt | ccggtgtcat | caacatcaag | 660 |
| ctcaaacaca | atctggatga | cgcgaacctg | acggttcgtg | gaggcatcac | tgaccgtgga | 720 |
| gatgccagt | ccggcatgat | ttctggctac | aagggctgga | attttgatca | tggccgcggc | 780 |
| aacgtgacgg | tctccggatc | ttacatgacc | cagagcggga | tccgtcagaa | cagccgtgac | 840 |
| tgggccaacc | cggttgtgtc | tggtctgatt | gcaccgggtg | gttcgccgac | ttacggatcg | 900 |
| tccatcccga | cggcgggtcg | tttcatcact | gatactgcgg | ataatgttcc | caatggtgat | 960 |
| ggatcgttcc | acaatttcag | caagaaagat | cgctacaact | acggtaatga | tcagagcctg | 1020 |
| acgaactcct | tgcaggatgc | cacgctgtcg | ttcgatgcac | attacgacgt | gaaccgtcat | 1080 |
| ttcacgccgt | atggcaactt | cctgtattcg | catcgtaact | ctaatacgca | gatggcgccg | 1140 |
| attccggtgt | ctggtagcat | ctacccgtcc | actctgccgg | tagccatcac | cattccagga | 1200 |
| agtgcgccgt | acaattcgct | tggcgaagat | gccacgatgt | acaagcgtat | gggtgaatgg | 1260 |
| ggtgatcgcg | tcagtcagac | tgctaccgac | acatacacgg | caaagattgg | cgcttcgggt | 1320 |
| gatatcaccc | acggttggaa | atatgacctg | tcctataccctc | acggatggaa | ccaggtcatg | 1380 |
| tcccagactt | ctggcgttgg | taattattcc | aagctgcttc | agagctacgg | tctatccgct | 1440 |
| gaagagccgg | gcaatcctga | cagtgcgctg | gtttacaacc | cgtcgatctg | cactgcagcg | 1500 |
| gctggctgca | cactgtccaa | cccctttcaac | aagctttcgc | cgcaagcggc | tgattactcg | 1560 |
| aactacacgt | cgcacgatca | ctactactat | cagctgcgtg | atctgaacct | gcgtattaac | 1620 |
| aataaccatg | ttgttcacat | gccgtggaag | aacggtggcg | atctaggtat | cgcgctgggt | 1680 |
| atggagcatc | gtggtgagca | gcttgcctat | catccggatg | ccctcgttga | atctggccag | 1740 |
| acgctgacga | actctgcttc | ctacacgggt | ggtggattca | acgtcacgga | aggctacctc | 1800 |
| gaaggtaaag | ccacgctgct | gcacaatgca | ttccttgcca | aggatctgac | gattgacggt | 1860 |
| cagggccgtt | actcgtctta | caacacgttc | ggcagcacga | agaactggaa | ggcgtccatc | 1920 |
| aactgggcac | cggttcagga | catccgcttc | cgtgcaacgc | ttggcacgtc | ctaccgtcag | 1980 |
| cctaacgtct | atgagctgta | tggcggtcag | tctctcggct | atgcatcagc | aactgaccca | 2040 |
| tgcgacagcg | ggcaggtcgg | cacatatggc | agtctgacgc | caattgtggc | ggcaaattgc | 2100 |
| gccaagcagg | ggattaacag | cagtaatttc | gtgtctgctt | cctccagtca | ggttccgacc | 2160 |
| ctgtttggtg | gcaatcccaa | gctgaagcct | gaaactggcc | gtacctacac | gtttggtaca | 2220 |
| acggtcacgc | cgcgttggat | tccaggcctc | tcggcttccg | tggaatactg | gcattacacg | 2280 |

-continued

```
ctcaagaaca tgatttcgta cctgagcagt cagtacatca tgaaccagtg ctacacgggt    2340
gcaaacacgt catattgcaa tgacattacc cgcgttggca gcacgaacca gctaaactcc    2400
gtgacagctc tgtatggcaa catcggcgga ctgaagacga gcggcatcga ctttgacctt    2460
gactaccgta tccgcgttac atctcgcgac gttctgacat tgtccaacaa cttttcagcaa   2520 cttgtgagct atcttcagca gaacgagctc ggcggaaagt ggtacaatta tgcaggtcgc    2580
atgttctacc aaaacggtac tggcaacccc cgcgttcgtg attatgcgac cgttggctgg    2640
cagcatggtg caattggcgt cacatatatg atgagctata tgggtggtat cgttggaac    2700 gactcggaaa ctgatgtgac ccgttcagct tcgggccgca tcaagacgcc tggcatcttc    2760
tctcatgatg ttacggtgac ttatcgttgg aaaaagtgga acttcgaagc tggtgtgaac   2820
aacctgctcg acaagaagcc tccctttgtt tctggtggga cagacaacag cgcggctgcc    2880
ctttatggca acctttacat gggacgtaac gtcttcctgc aggcaggcgt gaacttctga    2940
```

```
<210> SEQ ID NO 6
<211> LENGTH: 979
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Met Ile Val Ser Arg Arg Asn Thr Leu Leu Cys Ala Ser Val Leu Gly
1               5                   10                  15

Met Gly Ala Leu Ser Ser Val Ala His Ala Ala Thr Glu Ser Thr His
            20                  25                  30

Thr Ser Ser His Val Arg His Lys Thr Val Thr His Gly Pro Val Arg
        35                  40                  45

Ser Ala Ala Thr Pro Ala Thr Thr Ala Pro Val Ser Val Ala Arg Pro
    50                  55                  60

Val Ala Ala Pro Gln Phe Ser Ala Pro Val Ala Val Asn Arg Ser His
65                  70                  75                  80

Ala Val Arg Ser Ile Asp Ser Gly Thr Gln Glu Ser Val Val Val Thr
                85                  90                  95

Gly Ser Ala Leu Ser Thr Ser Asn Asn Gln Asn Ala Asn Pro Val Gln
            100                 105                 110

Ile Val Thr Ser Lys Gln Ile Glu Gln Thr Gly Ile Asn Thr Leu Gly
        115                 120                 125

Asp Tyr Leu Gln Arg Leu Pro Ser Val Gly Ser Ser Gly Thr Thr Asn
    130                 135                 140

Ser Gln Thr Asn Asn Thr Ala Gly Val Ser Cys Thr Asp Ile Arg Asn
145                 150                 155                 160

Leu Gly Lys Ser Arg Val Leu Val Leu Ile Asp Gly Lys Arg Ala Ala
                165                 170                 175

Ile Asp Gly Ser Ser Ser Cys Phe Asp Leu Asn Thr Ile Asn Ile His
            180                 185                 190

Gln Val Ala Ser Val Glu Ile Leu Lys Asp Gly Gly Ser Glu Leu Tyr
        195                 200                 205

Gly Ala Asp Ala Val Ser Gly Val Ile Asn Ile Lys Leu Lys His Asn
    210                 215                 220

Leu Asp Asp Ala Asn Leu Thr Val Arg Gly Gly Ile Thr Asp Arg Gly
225                 230                 235                 240
```

```
Asp Gly Gln Ser Gly Met Ile Ser Gly Tyr Lys Gly Trp Asn Phe Asp
                245                 250                 255

His Gly Arg Gly Asn Val Thr Val Ser Gly Ser Tyr Met Thr Gln Ser
            260                 265                 270

Gly Ile Arg Gln Asn Ser Arg Asp Trp Ala Asn Pro Val Val Ser Gly
        275                 280                 285

Leu Ile Ala Pro Gly Gly Ser Pro Thr Tyr Gly Ser Ser Ile Pro Thr
    290                 295                 300

Ala Gly Arg Phe Ile Thr Asp Thr Ala Asp Asn Val Pro Asn Gly Asp
305                 310                 315                 320

Gly Ser Phe His Asn Phe Ser Lys Lys Asp Arg Tyr Asn Tyr Gly Asn
                325                 330                 335

Asp Gln Ser Leu Thr Asn Ser Leu Gln Asp Ala Thr Leu Ser Phe Asp
            340                 345                 350

Ala His Tyr Asp Val Asn Arg His Phe Thr Pro Tyr Gly Asn Phe Leu
        355                 360                 365

Tyr Ser His Arg Asn Ser Asn Thr Gln Met Ala Pro Ile Pro Val Ser
    370                 375                 380

Gly Ser Ile Tyr Pro Ser Thr Leu Pro Val Ala Ile Thr Ile Pro Gly
385                 390                 395                 400

Ser Ala Pro Tyr Asn Ser Leu Gly Glu Asp Ala Thr Met Tyr Lys Arg
                405                 410                 415

Met Gly Glu Trp Gly Asp Arg Val Ser Gln Thr Ala Thr Asp Thr Tyr
            420                 425                 430

Thr Ala Lys Ile Gly Ala Ser Gly Asp Ile Thr His Gly Trp Lys Tyr
        435                 440                 445

Asp Leu Ser Tyr Thr Tyr Gly Trp Asn Gln Val Met Ser Gln Thr Ser
    450                 455                 460

Gly Val Gly Asn Tyr Ser Lys Leu Leu Gln Ser Tyr Gly Leu Ser Ala
465                 470                 475                 480

Glu Glu Pro Gly Asn Pro Asp Ser Ala Leu Val Tyr Asn Pro Ser Ile
                485                 490                 495

Cys Thr Ala Ala Ala Gly Cys Thr Leu Ser Asn Pro Phe Asn Lys Leu
            500                 505                 510

Ser Pro Gln Ala Ala Asp Tyr Ser Asn Tyr Thr Ser His Asp His Tyr
        515                 520                 525

Tyr Tyr Gln Leu Arg Asp Leu Asn Leu Arg Ile Asn Asn His Val
    530                 535                 540

Val His Met Pro Trp Lys Asn Gly Gly Asp Leu Gly Ile Ala Leu Gly
545                 550                 555                 560

Met Glu His Arg Gly Glu Gln Leu Ala Tyr His Pro Asp Ala Leu Val
                565                 570                 575

Glu Ser Gly Gln Thr Leu Thr Asn Ser Ala Ser Tyr Thr Gly Gly Gly
            580                 585                 590

Phe Asn Val Thr Glu Gly Tyr Leu Glu Gly Lys Ala Thr Leu Leu His
        595                 600                 605

Asn Ala Phe Leu Ala Lys Asp Leu Thr Ile Asp Gly Gln Gly Arg Tyr
    610                 615                 620

Ser Ser Tyr Asn Thr Phe Gly Ser Thr Lys Asn Trp Lys Ala Ser Ile
625                 630                 635                 640

Asn Trp Ala Pro Val Gln Asp Ile Arg Phe Arg Ala Thr Leu Gly Thr
                645                 650                 655

Ser Tyr Arg Gln Pro Asn Val Tyr Glu Leu Tyr Gly Gly Gln Ser Leu
```

```
            660                665                670
Gly Tyr Ala Ser Ala Thr Asp Pro Cys Asp Ser Gly Gln Val Gly Thr
            675                680                685

Tyr Gly Ser Leu Thr Pro Ile Val Ala Ala Asn Cys Ala Lys Gln Gly
        690                695                700

Ile Asn Ser Ser Asn Phe Val Ser Ala Ser Ser Gln Val Pro Thr
705                710                715                720

Leu Phe Gly Gly Asn Pro Lys Leu Lys Pro Glu Thr Gly Arg Thr Tyr
                725                730                735

Thr Phe Gly Thr Thr Val Thr Pro Arg Trp Ile Pro Gly Leu Ser Ala
            740                745                750

Ser Val Glu Tyr Trp His Tyr Thr Leu Lys Asn Met Ile Ser Tyr Leu
        755                760                765

Ser Ser Gln Tyr Ile Met Asn Gln Cys Tyr Thr Gly Ala Asn Thr Ser
        770                775                780

Tyr Cys Asn Asp Ile Thr Arg Val Gly Ser Thr Asn Gln Leu Asn Ser
785                790                795                800

Val Thr Ala Leu Tyr Gly Asn Ile Gly Gly Leu Lys Thr Ser Gly Ile
                805                810                815

Asp Phe Asp Leu Asp Tyr Arg Ile Arg Val Thr Ser Arg Asp Val Leu
                820                825                830

Thr Leu Ser Asn Asn Phe Gln Gln Leu Val Ser Tyr Leu Gln Gln Asn
            835                840                845

Glu Leu Gly Gly Lys Trp Tyr Asn Tyr Ala Gly Arg Met Phe Tyr Gln
850                855                860

Asn Gly Thr Gly Asn Pro Arg Val Arg Asp Tyr Ala Thr Val Gly Trp
865                870                875                880

Gln His Gly Ala Ile Gly Val Thr Tyr Met Met Ser Tyr Met Gly Gly
                885                890                895

Met Arg Trp Asn Asp Ser Glu Thr Asp Val Thr Arg Ser Ala Ser Gly
                900                905                910

Arg Ile Lys Thr Pro Gly Ile Phe Ser His Asp Val Thr Val Thr Tyr
            915                920                925

Arg Trp Lys Lys Trp Asn Phe Glu Ala Gly Val Asn Asn Leu Leu Asp
        930                935                940

Lys Lys Pro Pro Phe Val Ser Gly Gly Thr Asp Asn Ser Ala Ala Ala
945                950                955                960

Leu Tyr Gly Asn Leu Tyr Met Gly Arg Asn Val Phe Leu Gln Ala Gly
                965                970                975

Val Asn Phe

<210> SEQ ID NO 7
<211> LENGTH: 843
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7
atgcgcgttg ccctgatcca gatggctcct tcggcggacc ggagtgccaa tatccttcaa      60
gctcagcggc tggtttcaga agctgtcaaa gctcggaagc cagatcttgt ggtgctgcct     120
gaaatctgga gctgtctggg tggttcggct gcgaccaagc aggctaatgc agagcttcta     180
cctgatccag gcgatgctgg aggtgtactc tacgaagcgt tgagggccat ggcccgggaa     240
```

```
cataatgtct gggttcacgg tggttcaatc ggagaacttg tagggcctga gtcgggcgac    300
aagcttgcca atacttcact cgttttcaac cctgatggcg aggaatgtgg gcgttacaga    360
aaaatccatc tcttcgatgt tattacaccc aatggggacg gctatcgtga aagcgataat    420
tatgtgcccg gggaagcgat cgaagtcgtc gatattgatg gcgtcccaac cggcctcgcg    480
atttgctatg atttgaggtt tgctgagctg tttcttgcac ttcgggctgc ggatgttgag    540
atgattgttc tgcccgcagc gtttacgcag caaacgggtg aagctcactg ggacattctt    600
gtccgtgctc gcgctattga gtctcagacg tgggtgatag cgtgtggaac aacgggctgg    660
catgtcgatg gcaaggcaa tcagcgccag acctatggcc attccatgat cgtcagccca    720
tggggcgagg ttgttcttca attgggtagt gaagaaggct gggggggtggc tgatcttgat    780 atggatgagg ttcgacaggt gcgggagaga atgcctgtgc agataaacag gcggctgatt    840
tga                                                                  843
```

<210> SEQ ID NO 8
<211> LENGTH: 280
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

```
Met Arg Val Ala Leu Ile Gln Met Ala Pro Ser Ala Asp Arg Ser Ala
1               5                   10                  15

Asn Ile Leu Gln Ala Gln Arg Leu Val Ser Glu Ala Val Lys Ala Arg
            20                  25                  30

Lys Pro Asp Leu Val Val Leu Pro Glu Ile Trp Ser Cys Leu Gly Gly
        35                  40                  45

Ser Ala Ala Thr Lys Gln Ala Asn Ala Glu Leu Leu Pro Asp Pro Gly
    50                  55                  60

Asp Ala Gly Gly Val Leu Tyr Glu Ala Leu Arg Ala Met Ala Arg Glu
65                  70                  75                  80

His Asn Val Trp Val His Gly Ser Ile Gly Glu Leu Val Gly Pro
                85                  90                  95

Glu Ser Gly Asp Lys Leu Ala Asn Thr Ser Leu Val Phe Asn Pro Asp
            100                 105                 110

Gly Glu Glu Cys Gly Arg Tyr Arg Lys Ile His Leu Phe Asp Val Ile
        115                 120                 125

Thr Pro Asn Gly Asp Gly Tyr Arg Glu Ser Asp Asn Tyr Val Pro Gly
    130                 135                 140

Glu Ala Ile Glu Val Val Asp Ile Asp Gly Val Pro Thr Gly Leu Ala
145                 150                 155                 160

Ile Cys Tyr Asp Leu Arg Phe Ala Glu Leu Phe Leu Ala Leu Arg Ala
                165                 170                 175

Ala Asp Val Glu Met Ile Val Leu Pro Ala Ala Phe Thr Gln Gln Thr
            180                 185                 190

Gly Glu Ala His Trp Asp Ile Leu Val Arg Ala Arg Ala Ile Glu Ser
        195                 200                 205

Gln Thr Trp Val Ile Ala Cys Gly Thr Thr Gly Trp His Val Asp Gly
    210                 215                 220

Gln Gly Asn Gln Arg Gln Thr Tyr Gly His Ser Met Ile Val Ser Pro
225                 230                 235                 240
```

Trp Gly Glu Val Val Leu Gln Leu Gly Ser Glu Gly Trp Gly Val
                245                 250                 255

Ala Asp Leu Asp Met Asp Glu Val Arg Gln Val Arg Glu Arg Met Pro
        260                 265                 270

Val Gln Ile Asn Arg Arg Leu Ile
    275                 280

<210> SEQ ID NO 9
<211> LENGTH: 939
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9
atgatgaaag caggaccgat gaaaaaactc tggcgatatc tcccagcgtt gccggcgctg      60
atgctatcgg gttgcacggt tgatctgctt cagccgcgcg gtccgatcgc agaaatgaac     120
cgcgacgtta tggtggcaga atttgccatc atgatggcga ttgtggttcc gacctgtatc     180
gcaacgcttt attttgcttg gaagtatcgc gcttccaata cccaggccga atatctgccg     240
acctgggatc actcaacgaa gattgagtat gtcatctggg gcgtccctgc tctgatcatt     300
attgcccttg gcgcgatcag ctggtacagc acccatgctt atgacccgta ccgcccgctc     360
cagacggctg acaacgtcaa gccgctgaac gttcaggtgg tctctctcga ctggaaatgg     420
ctgttcatct atccggatct ggggatcgcc acgatcaacc agctggatgt gcccacgaac     480
acgccgctga acttccagat cacctctgac actgtcatga cgtcgttctt catcccgcgt     540
ctgggatcaa tgatctactc catgccgggt cagcagacac agctgcatct tcttgcaact     600
gagtcgggtg actatctggg tgaagcttcc cagttcagtg gtcgcggttt ctctgacatg     660
aagttccgca ccctcgccat ggcacctgaa gaattcagcg cctgggtcga aaggtgaag      720 agcggcagcg aaaaccctcga tgacacgact tatccgaagt acgccgcccc gcaggaagct     780
gcgccggttc agtatttcgc gcatgtccag ccggatctct tcgacggcat cgtcgccaag     840
tacaacaatg gcatgatggt tgagaagacg acgggcaagg tcatgcatat gcagtccgct     900
tccagcgctg caccgtccga cactggcatg aaggaataa                          939

<210> SEQ ID NO 10
<211> LENGTH: 312
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Met Met Lys Ala Gly Pro Met Lys Lys Leu Trp Arg Tyr Leu Pro Ala
1               5                   10                  15

Leu Pro Ala Leu Met Leu Ser Gly Cys Thr Val Asp Leu Leu Gln Pro
            20                  25                  30

Arg Gly Pro Ile Ala Glu Met Asn Arg Asp Val Met Val Ala Glu Phe
        35                  40                  45

Ala Ile Met Met Ala Ile Val Val Pro Thr Cys Ile Ala Thr Leu Tyr
    50                  55                  60

Phe Ala Trp Lys Tyr Arg Ala Ser Asn Thr Gln Ala Glu Tyr Leu Pro
65                  70                  75                  80

Thr Trp Asp His Ser Thr Lys Ile Glu Tyr Val Ile Trp Gly Val Pro

```
                    85                  90                  95
Ala Leu Ile Ile Ile Ala Leu Gly Ala Ile Ser Trp Tyr Ser Thr His
                100                 105                 110

Ala Tyr Asp Pro Tyr Arg Pro Leu Gln Thr Ala Asp Asn Val Lys Pro
            115                 120                 125

Leu Asn Val Gln Val Val Ser Leu Asp Trp Lys Trp Leu Phe Ile Tyr
        130                 135                 140

Pro Asp Leu Gly Ile Ala Thr Ile Asn Gln Leu Asp Val Pro Thr Asn
145                 150                 155                 160

Thr Pro Leu Asn Phe Gln Ile Thr Ser Asp Thr Val Met Thr Ser Phe
                165                 170                 175

Phe Ile Pro Arg Leu Gly Ser Met Ile Tyr Ser Met Pro Gly Gln Gln
            180                 185                 190

Thr Gln Leu His Leu Leu Ala Thr Glu Ser Gly Asp Tyr Leu Gly Glu
        195                 200                 205

Ala Ser Gln Phe Ser Gly Arg Gly Phe Ser Asp Met Lys Phe Arg Thr
210                 215                 220

Leu Ala Met Ala Pro Glu Glu Phe Ser Ala Trp Val Glu Lys Val Lys
225                 230                 235                 240

Ser Gly Ser Glu Asn Leu Asp Asp Thr Thr Tyr Pro Lys Tyr Ala Ala
                245                 250                 255

Pro Gln Glu Ala Ala Pro Val Gln Tyr Phe Ala His Val Gln Pro Asp
            260                 265                 270

Leu Phe Asp Gly Ile Val Ala Lys Tyr Asn Asn Gly Met Met Val Glu
        275                 280                 285

Lys Thr Thr Gly Lys Val Met His Met Gln Ser Ala Ser Ser Ala Ala
290                 295                 300

Pro Ser Asp Thr Gly Met Lys Glu
305                 310

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
aacaagccag ggatgtaacg                                              20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
cagcaacacc ttcttcacga                                              20

<210> SEQ ID NO 13
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 13
cagctgacgc ttcgtccgaa gaacccgctc tccgatgccg atatctgggg tggcacaatc    60

<210> SEQ ID NO 14
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
ctacatcccg accaagacgg gcgatatctt tgtcctcgac cgccgtacgg gcaaggaag     59

<210> SEQ ID NO 15
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
agcacccacg cctacgaccc gtaccgcccc cttcagacgg ctgacaacgt caagccctg     59

<210> SEQ ID NO 16
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
cgcaccaaca aggtggtctg gcagcatcgt aacggtacgc tccgtgactc catgcacggc    60

<210> SEQ ID NO 17
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
tacaagtggt atcgattggg attttgatta tcggatccgt ctgactagca tggattccat    60

<210> SEQ ID NO 18
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
catcggcgtc atgatcggga tctgcacgca tctgggc                             37

<210> SEQ ID NO 19
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
```
cgatgcagaa accgggcaga agtgttccgg ctttggcaac gacggcgaac tggaacctg    59

<210> SEQ ID NO 20
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
tcttaatgcg cttctatgtg tttgtccgaa ggtcaagtgc    40

<210> SEQ ID NO 21
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
gcagtaattt cgtgtctgct tcctccagtc aggttccgac cctgttt    47

<210> SEQ ID NO 22
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
tggcgatcgc tggtctccgc tgaagcagat caattcgacc aatgttcaga acctcaaggt    60

<210> SEQ ID NO 23
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
agactcaata gcgcgagcac ggacaagaat gtcccagtga gcttcacccg tttgctgcgt    60

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
agagtttgat cmtggctcag    20

<210> SEQ ID NO 25
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
tacggytacc ttgttacgac tt                                          22

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
caccagccta accagatttc                                             20

<210> SEQ ID NO 27
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
gggttgtatt gatgagatta gt                                          22

<210> SEQ ID NO 28
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
gcttctgaca caactgtgtt cactagc                                     27

<210> SEQ ID NO 29
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
caccaacttc atccacgttc acc                                         23

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
tgttcacaat ggataggcac                                             20

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
tctgggtttt ccaaagcaag                                             20

<210> SEQ ID NO 32
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
tgaagacgga ttgccctcat t                                          21

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
gctggtgcca gtaagagctt                                            20

<210> SEQ ID NO 34
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
ggcacaatct tcgaccagat gttctgcagc atctacttcc actccctgcg ctacgaaggt    60

<210> SEQ ID NO 35
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
gggcaaggaa gtcgtcgctg ctcctgaaac accagttcca ggtggtgcag ctccgggcga    60

<210> SEQ ID NO 36
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
gacagcgtca agccactgaa tgttcaggtg gtctctctcg actggaaatg gctgttcatc    60

<210> SEQ ID NO 37
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
atgcacggca gctccctgcc catcccgctg cctccgatca agatcggtgt tccgagcctt    60

<210> SEQ ID NO 38
<211> LENGTH: 60
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 38
ggattccatc actgtcagca ataacctgca gaacctggtc aattttttccc agcagcagac    60

<210> SEQ ID NO 39
<211> LENGTH: 47
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 39
tgcgtgccga ctttcgacgc cccgacgcag gcagaacctg ccgggaa    47

<210> SEQ ID NO 40
<211> LENGTH: 60
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 40
gaactggaac tgcgcgagcc gaaccagcct tacgtcacgc caggcatgta tgagccgacg    60

<210> SEQ ID NO 41
<211> LENGTH: 58
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 41
aggtcaagtg ctgcaccaaa taacagctct aggaacatca tgagcacatc ttcccggc    58

<210> SEQ ID NO 42
<211> LENGTH: 51
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 42
ggtggtaata caaagctgcg tccagaagca gggcgtacct acacctttgg t    51

<210> SEQ ID NO 43
<211> LENGTH: 60
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 43
cctcaaggtg gcatggcaca tccacaccaa ggatctgatg ggaccgaatg atccgggcga    60

```
<210> SEQ ID NO 44
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
aaacgctgcg ggcagaacaa tcatctcaac atccgcagcc cgaag                45
```

COMPOSITIONS AND METHODS FOR IMPROVING MITOCHONDRIAL FUNCTION

CROSS-REFERENCE TO RELATED APPLICATIONS

This application is a continuation of U.S. application Ser. No. 16/293,789, filed Mar. 6, 2019, which is a continuation of PCT Application No. PCT/US2019/014725, filed Jan. 23, 2019, which claims benefit under 35 U.S.C. § 119(e) of U.S. Provisional Application No. 62/620,641, filed Jan. 23, 2018 and U.S. Provisional Application No. 62/721,979, filed Aug. 23, 2018, the contents of each of which are incorporated herein by reference in their entirety.

GOVERNMENT SUPPORT

This invention was made with government support under Grant No. AG043181-16A, awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Feb. 21, 2019, is named 030258-091760WOPT_SL.txt and is 42,162 bytes in size.

FIELD OF THE INVENTION

The field of the invention relates to bacterial compositions or bacterial extracts for the treatment of a symptom of a disease associated with mitochondrial dysfunction.

BACKGROUND

Mitochondria play a crucial role in ATP generation, fatty acid β-oxidation, catabolism of amino acids, ketogenesis, generation of reactive oxygen species (ROS) and calcium homeostasis. Mitochondrial dysfunction is associated with a number of human diseases, including neurological and muscular degeneration, cardiovascular disorders, obesity, diabetes, and conditions such as aging. Mitochondria contribute to aging through decreased ATP production, increased ROS production, and activation of apoptotic pathways. Decreases in mitochondrial energy production combined with increased oxidative stress, play a causal role in several neurodegenerative disease including Alzheimer's disease, Parkinson's disease, Huntington's disease, and amyotrophic lateral sclerosis. Also, aging is by far the greatest risk factor for several of these neurodegenerative diseases. Regardless of whether a primary or secondary cause, mitochondrial dysfunction holds promise as a target for identifying therapeutics for neurodegenerative diseases. With the increasing average life expectancy worldwide, the number of people affected by aging related decline in mitochondrial function will rise considerably in the near future. Thus, there is a significant clinical unmet need for new therapeutic approaches that not only can be used to slow neurodegenerative diseases but also as preventive measures for protecting or improving mitochondrial function in the aging population.

SUMMARY

The methods, compositions and treatments described herein are based, in part, on the discovery of a bacterial extract or bacterial composition that improves mitochondrial function by, for example, increasing production of intracellular energy (e.g., ATP). Accordingly, provided herein are bacterial extracts and compositions for the treatment of mitochondrial dysfunction associated with metabolic disorders, neurodegenerative disorders (e.g., Parkinson's disease, among others) and peroxisomal disorders.

The present invention relates generally to the use of members of live or inactivated Acetobacteriaceae family microbes, a microbial combination, an extract, active fraction or metabolites, or a combination thereof for promoting, enhancing and/or restoring mitochondrial function. Such compositions can be used for treatment or prevention of diseases, developmental delays, and symptoms related to mitochondrial dysfunction, such as aging, metabolic disorders, muscular disorders and neurodegenerative diseases.

Provided herein in one aspect is a composition comprising a measured amount of one or more bacterium that comprises and expresses one or more nucleic acid sequences encoding one or more of membrane-bound PQQ-dependent glucose dehydrogenase (mGDH), ubiquinol-cytochrome c reductase iron-sulfur subunit, TonB-dependent receptor, carbon-nitrogen hydrolase, and ubiquinol oxidase subunit II.

In one embodiment of this aspect and all other aspects described herein, the bacterium is from the Acetobacteriaceae family.

In another embodiment of this aspect and all other aspects described herein, the bacterium is *Gluconobacter* spp, *Acetobacter* spp., *Gluconoacaetobacter* spp., *Acidomonas* spp, *Ameyamaea* spp., *Asaia* spp., *Granulibacter* spp., *Kozakia* spp., *Neoasaia* spp., *Neokomagataea* spp., *Saccharibacter* spp., *Swaminathania* spp., or *Tanticharoenia* spp. or combination of two or more of these (e.g., a combination of three or more, 4 or more, 5 or more, 6 or more, 7 or more, 8 or more, 9 or more, 10 or more, 11 or more, or 12 or more of these).

In another embodiment of this aspect and all other aspects described herein, the bacterium is *Gluconobacter albidus, Gluconobacter cerinus, Gluconobacter frateruii, Gluconobacter japonicus, Gluconobacter kondonii, Gluconobacter nephelii, Gluconobacter oxydans, Gluconoacetobacter diazotrophicus, Gluconoacetobacter hansenii, Gluconoacetobacter saccharivorans, Acetobacter aceti* or *Acetobacter malorum*. In another embodiment of this aspect and all other aspects provided herein, the bacterium is *Gluconobacter* EBT 405. In another embodiment, the composition comprises at least two or more, at least three or more, at least four or more, at least five or more, at least six or more, at least seven or more, at least eight or more, at least nine or more, at least ten or more, at least eleven or more, at least twelve (or each of) these bacterial species.

In another embodiment of this aspect and all other aspects described herein, one or more of the nucleic acid sequences are exogenous nucleic acid sequences.

In another embodiment of this aspect and all other aspects described herein, the bacterium comprises and expresses nucleic acid sequences encoding each of membrane-bound PQQ-dependent glucose dehydrogenase (mGDH), ubiquinol-cytochrome c reductase iron-sulfur subunit, TonB-dependent receptor, carbon-nitrogen hydrolase, and ubiquinol oxidase subunit II.

In another embodiment of this aspect and all other aspects described herein, the measured amount of the one or more bacterium is lyophilized.

In another embodiment of this aspect and all other aspects described herein, the measured amount is an amount effective to induce expression and/or activity of mitochondrial transcription factor A (TFAM), or peroxisome proliferator activated receptor gamma coactivator 1 (PGC) in a human cell upon administration to a subject in need thereof.

In another embodiment of this aspect and all other aspects described herein, the amount effective to induce expression and/or activity of TFAM, or PGC in a human cell is $1 \times 10^6$ bacteria.

In another embodiment of this aspect and all other aspects described herein, the composition further comprises one or more added bacterial metabolites selected from the group consisting of gluconic acid, 2-keto-gluconic acid, 5-keto-gluconic acid, and 2,5-diketo-D-gluconic acid.

In another embodiment of this aspect and all other aspects described herein, the bacterium is viable, attenuated or heat-inactivated.

In another embodiment of this aspect and all other aspects described herein, the composition is formulated as a food, a beverage, a feed composition, a probiotic, a nutritional supplement, or a pharmaceutical composition.

In another embodiment of this aspect and all other aspects described herein, the composition further comprises a prebiotic.

In another embodiment of this aspect and all other aspects described herein, the prebiotic comprises a fructooligosaccharide, an inulin, an isomaltooligosaccharide, lactilol, lactosucrose, lactulose, a soy oligosaccharide, a transgalactooligosaccharide or a xylooligosaccharide, In another embodiment of this aspect and all other aspects described herein, the composition further comprises a pharmaceutically acceptable carrier.

In another embodiment of this aspect and all other aspects described herein, the composition is formulated for oral administration.

In another embodiment of this aspect and all other aspects described herein, the composition is an enteric-coated formulation.

Another aspect provided herein relates to a composition comprising a therapeutically effective amount of an extract or fraction derived from at least one bacterium that comprises and expresses one or more nucleic acid sequences encoding an enzyme selected from the group consisting of membrane-bound PQQ-dependent glucose dehydrogenase (mGDH), ubiquinol-cytochrome c reductase iron-sulfur subunit, TonB-dependent receptor, carbon-nitrogen hydrolase, and ubiquinol oxidase subunit II.

In one embodiment of this aspect and all other aspects provided herein, the at least one bacterium comprises and expresses each of the enzymes membrane-bound PQQ-dependent glucose dehydrogenase (mGDH), ubiquinol-cytochrome c reductase iron-sulfur subunit, TonB-dependent receptor, carbon-nitrogen hydrolase, and ubiquinol oxidase subunit II.

In another embodiment of this aspect and all other aspects provided herein, the extract or fraction comprises one or more metabolites selected from gluconic acid, 2-keto-gluconic acid, 5-keto-gluconic acid, and 2,5-diketo-D-gluconic acid.

In another embodiment of this aspect and all other aspects provided herein, the extract or fraction is from bacterial cells cultured in a medium comprising: (i) standard Lysogeny broth (1% tryptone, 0.5% yeast extract, and 1% sodium chloride) containing 1% glucose, (ii) standard Hestrin-Schramm broth (D-glucose 2%, 0.5% yeast extract, 0.5% peptone, 0.27% disodium phosphate, 0.115% citric acid) or (iii) $CaCO_3$ medium comprising 8% glucose, 0.5% yeast extract, 0.2% mannitol, 0.05% magnesium sulphate, and 10% calcium carbonate.

In another embodiment of this aspect and all other aspects provided herein, the extract or fraction comprises metabolites or bacterial byproducts that promote ATP production in at least one cell type of a host mammal administered the composition.

In another embodiment of this aspect and all other aspects provided herein, the extract or fraction does not comprise viable bacterial cells.

In another embodiment of this aspect and all other aspects provided herein, the extract or fraction lacks detectable bacteria.

In another embodiment of this aspect and all other aspects provided herein, the extract or fraction further comprises attenuated or heat-inactivated bacteria.

In another embodiment of this aspect and all other aspects provided herein, the bacterium is from the Acetobacteriaceae family.

In another embodiment of this aspect and all other aspects provided herein, the bacterium is *Gluconobacter* spp, *Acetobacter* spp., *Gluconoacaetobacter* spp., *Acidomonas* spp, *Ameyamaea* spp., *Asaia* spp., *Granulibacter* spp., *Kozakia* spp., *Neoasaia* spp., *Neokomagataea* spp., *Saccharibacter* spp., *Swaminathania* spp., or *Tanticharoenia* spp. or combination of two or more of these (e.g., a combination of three or more, 4 or more, 5 or more, 6 or more, 7 or more, 8 or more, 9 or more, 10 or more, 11 or more, or 12 or more of these).

In another embodiment of this aspect and all other aspects described herein, the bacterium is *Gluconobacter albidus*, *Gluconobacter cerinus*, *Gluconobacter frateruii*, *Gluconobacter japonicus*, *Gluconobacter kondonii*, *Gluconobacter nephelii*, *Gluconobacter oxydans*, *Gluconoacetobacter diazotrophicus*, *Gluconoacetobacter hansenii*, *Gluconoacetobacter saccharivorans*, *Acetobacter aceti* or *Acetobacter malorum*. In another embodiment of this aspect and all other aspects provided herein, the bacterium is *Gluconobacter* EBT 405. In another embodiment, the composition comprises at least two or more, at least three or more, at least four or more, at least five or more, at least six or more, at least seven or more, at least eight or more, at least nine or more, at least ten or more, at least eleven or more, at least twelve (or each of) these bacterial species.

In another embodiment of this aspect and all other aspects provided herein, one or more of the nucleic acid sequences is/are an exogenous nucleic acid sequence(s).

In another embodiment of this aspect and all other aspects provided herein, the composition is formulated as a food, a beverage, a feed composition, a nutritional supplement, or a pharmaceutical composition.

In another embodiment of this aspect and all other aspects provided herein, the composition further comprises a pharmaceutically acceptable carrier.

In another embodiment of this aspect and all other aspects provided herein, the composition is formulated for oral administration.

Also provided herein, in another aspect, is a method for increasing cellular ATP production in at least one cell type of a subject in need thereof, the method comprising administering to the subject a composition comprising an amount of at least one bacterium that comprises and expresses one or more nucleic acid sequences encoding one or more of membrane-bound PQQ-dependent glucose dehydrogenase (mGDH), ubiquinol-cytochrome c reductase iron-sulfur subunit, TonB-dependent receptor, carbon-nitrogen hydrolase, and ubiquinol oxidase subunit II, or an extract or fraction thereof, effective to increase cellular ATP production in at least one cell type.

In one embodiment of this aspect and all other aspects provided herein, the at least one bacterium expresses each of membrane-bound PQQ-dependent glucose dehydrogenase (mGDH), ubiquinol-cytochrome c reductase iron-sulfur subunit, TonB-dependent receptor, carbon-nitrogen hydrolase, and ubiquinol oxidase subunit II.

In another embodiment of this aspect and all other aspects provided herein, the at least one bacterium produces one or more of gluconic acid, 2-keto-gluconic acid, 5-keto-gluconic acid, and 2,5-diketo-D-gluconic acid.

In another embodiment of this aspect and all other aspects provided herein, the at least one bacterium produces each of gluconic acid, 2-keto-gluconic acid, 5-keto-gluconic acid, and 2,5-diketo-D-gluconic acid.

In another embodiment of this aspect and all other aspects provided herein, one or more of the nucleic acid sequences is exogenous to the bacterium.

In another embodiment of this aspect and all other aspects provided herein, the activity of complex I and/or complex II of the mitochondrial electron transport chain is increased in the one or more cell types.

In another embodiment of this aspect and all other aspects provided herein, the administering increases mitochondrial membrane potential.

In another embodiment of this aspect and all other aspects provided herein, the subject is human.

In another embodiment of this aspect and all other aspects provided herein, expression of peroxisome proliferator-activated receptor gamma coactivator 1-α (PGC-1α), and/or mitochondrial transcription factor A (TFAM) is increased.

In another embodiment of this aspect and all other aspects provided herein, AMP-activated protein kinase (AMPK) phosphorylation levels, nuclear respiratory factor-2 (Nrf2) protein levels, PGCα mRNA levels TFAM mRNA levels and/or mitochondrial DNA replication is increased.

In another embodiment of this aspect and all other aspects provided herein, the mitochondrial DNA copy number (mtDNA) is increased.

In another embodiment of this aspect and all other aspects provided herein, the method increases the developmental growth rate of a subject carrying a mutations in mitochondrial respiratory Complex I NADH:ubiquinone reductase.

In another embodiment of this aspect and all other aspects provided herein, the expression of at least one mitochondrial β-oxidation enzyme is increased.

In another embodiment of this aspect and all other aspects provided herein, the at least one mitochondrial β-oxidation enzyme is B0303.3, cpt-2, cpt-1, ech-1.2, or acdh-7.

In another embodiment of this aspect and all other aspects provided herein, the longevity of the subject is increased.

In another embodiment of this aspect and all other aspects provided herein, mitochondrial biogenesis is maintained or increased.

In another embodiment of this aspect and all other aspects provided herein, cellular ATP production is increased by at least 10% compared to the cellular ATP production prior to administration of the composition.

Another aspect provided herein relates to a method for making a bacterial extract, the method comprising culturing at least one bacterium that comprises and expresses one or more nucleic acid sequences encoding one or more of membrane-bound PQQ-dependent glucose dehydrogenase (mGDH), ubiquinol-cytochrome c reductase iron-sulfur subunit, TonB-dependent receptor, carbon-nitrogen hydrolase, and ubiquinol oxidase subunit II in a medium comprising: (i) standard Lysogeny broth (1% tryptone, 0.5% yeast extract, and 1% sodium chloride) containing 1% glucose, (ii) standard Hestrin-Schramm broth (D-glucose 2%, 0.5% yeast extract, 0.5% peptone, 0.27% disodium phosphate, 0.115% citric acid) or (iii) $CaCO_3$ medium comprising 8% glucose, 0.5% yeast extract, 0.2% mannitol, 0.05% magnesium sulphate, and 10% calcium carbonate.

In one embodiment of this aspect and all other aspects provided herein, the at least one bacterium comprises and expresses nucleic acid sequences encoding each of membrane-bound PQQ-dependent glucose dehydrogenase (mGDH), ubiquinol-cytochrome c reductase iron-sulfur subunit, TonB-dependent receptor, carbon-nitrogen hydrolase, and ubiquinol oxidase subunit II.

In another embodiment of this aspect and all other aspects provided herein, the at least one bacterium produces one or more of gluconic acid, 2-keto-gluconic acid, 5-keto-gluconic acid, and 2,5-diketo-D-gluconic acid.

Also provided herein, in another aspect, is a composition comprising an amount of gluconic acid, 2-keto-gluconic acid, 5-keto-gluconic acid, and/or 2,5-diketo-D-gluconic acid effective to increase cellular ATP production in at least one cell type of a host mammal administered the composition.

Another aspect provided herein relates to a composition comprising an amount of gluconic acid, 2-keto-gluconic acid, 5-keto-gluconic acid, and/or 2,5-diketo-D-gluconic acid effective to increase the expression and/or activity of mitochondrial transcription factor A (TFAM), or peroxisome proliferator activated receptor gamma coactivator 1 (PGC) in at least one cell type of a human subject administered the composition.

In one embodiment of this aspect and all other aspects provided herein, the composition comprises a bacterial extract or active fraction thereof.

In another embodiment of this aspect and all other aspects provided herein, the composition is formulated as a food, a beverage, a feed composition, a nutritional supplement, or a pharmaceutical composition.

Provided herein, in another aspect, is a method of treating Parkinson's disease, the method comprising administering to a subject having Parkinson's disease, a composition comprising a therapeutically effective amount of at least one bacterium that comprises and expresses one or more nucleic acid sequences encoding one or more of membrane-bound PQQ-dependent glucose dehydrogenase (mGDH), ubiquinol-cytochrome c reductase iron-sulfur subunit, TonB-dependent receptor, carbon-nitrogen hydrolase, and ubiquinol oxidase subunit II, or an extract or fraction thereof, thereby reducing at least one symptom of Parkinson's disease.

In one embodiment of this aspect and all other aspects provided herein, the at least one bacterium expresses each of membrane-bound PQQ-dependent glucose dehydrogenase (mGDH), ubiquinol-cytochrome c reductase iron-sulfur subunit, TonB-dependent receptor, carbon-nitrogen hydrolase, and ubiquinol oxidase subunit II.

In another embodiment of this aspect and all other aspects provided herein, the at least one bacterium produces one or more of gluconic acid, 2-keto-gluconic acid, 5-keto-gluconic acid, and/or 2,5-diketo-D-gluconic acid.

In another embodiment of this aspect and all other aspects provided herein, the at least one bacterium produces each of gluconic acid, 2-keto-gluconic acid, 5-keto-gluconic acid, and/or 2,5-diketo-D-gluconic acid.

In another embodiment of this aspect and all other aspects provided herein, the at least one symptom is selected from the group consisting of: tremor, sleep disturbance, mobility impairment, involuntary movement, muscle rigidity, rhythmic muscle contraction, slow bodily movement, slow shuffling gait, fatigue, dizziness, impaired balance, restlessness, amnesia, confusion, dementia, cognitive impairment, impaired speech, anxiety, apathy, distorted or loss of sense of smell, urinary incontinence, reduced facial expression, weight loss and constipation.

In another embodiment of this aspect and all other aspects provided herein, the bacterium is *Gluconobacter* EBT 405.

Another aspect provided herein relates to a method of treating a mitochondrial electron transport chain disorder, the method comprising administering to a subject having a mitochondrial electron transport chain disorder, a composition comprising a therapeutically effective amount of at least one bacterium that comprises and expresses one or more nucleic acid sequences encoding one or more of membrane-bound PQQ-dependent glucose dehydrogenase (mGDH), ubiquinol-cytochrome c reductase iron-sulfur subunit, TonB-dependent receptor, carbon-nitrogen hydrolase, and ubiquinol oxidase subunit II, or an extract or fraction thereof, thereby reducing at least one symptom of the mitochondrial electron transport chain disorder.

In one embodiment of this aspect and all other aspects provided herein, the mitochondrial electron transport chain disorder comprises a disorder or impaired activity in Complex I and/or Complex II.

In another embodiment of this aspect and all other aspects provided herein, the mitochondrial electron transport chain disorder is NADH dehydrogenase (NADH-CoQ reductase) deficiency, succinate dehydrogenase deficiency, Leigh Disease, mitochondrial DNA depletion, or mitochondrial insufficiency.

In another embodiment of this aspect and all other aspects provided herein, the at least one symptom is selected from the group consisting of: myopathy, mitochondrial encephalomyopathy, failure to thrive, developmental delay, hypotonia, lethargy, respiratory failure, ataxia, myoclonus, lactic acidosis, seizures, fatigue, nystagmus, poor reflexes, difficulty eating or swallowing, breathing difficulties, ataxia, congenital myopathy, infantile myopathy and hepatopathy.

In another embodiment of this aspect and all other aspects provided herein, the at least one bacterium expresses each of membrane-bound PQQ-dependent glucose dehydrogenase (mGDH), ubiquinol-cytochrome c reductase iron-sulfur subunit, TonB-dependent receptor, carbon-nitrogen hydrolase, and ubiquinol oxidase subunit II.

In another embodiment of this aspect and all other aspects provided herein, the at least one bacterium produces one or more of gluconic acid, 2-keto-gluconic acid, 5-keto-gluconic acid, and/or 2,5-diketo-D-gluconic acid.

In another embodiment of this aspect and all other aspects provided herein, the at least one bacterium produces each of gluconic acid, 2-keto-gluconic acid, 5-keto-gluconic acid, and/or 2,5-diketo-D-gluconic acid.

Another aspect provided herein relates to a method of treating a peroxisomal disorder, the method comprising administering to a subject having a peroxisomal disorder, a composition comprising a therapeutically effective amount of at least one bacterium that comprises one or more nucleic acid sequences such that the bacterium expresses the following enzymes: membrane-bound PQQ-dependent glucose dehydrogenase (mGDH), ubiquinol-cytochrome c reductase iron-sulfur subunit, TonB-dependent receptor, carbon-nitrogen hydrolase, and ubiquinol oxidase subunit II, or a bacterial extract thereof, thereby reducing at least one symptom of the peroxisomal disorder.

In another embodiment of this aspect and all other aspects provided herein, the peroxisomal disorder is Zellweger syndrome spectrum (PBD-ZSD), or rhizomelic chondrodysplasia punctate type 1 (RCDP1).

In another embodiment of this aspect and all other aspects provided herein, the PBD-ZSD is infantile Refsum disease, neonatal adrenoleukodystrophy, or Zellweger syndrome.

In another embodiment of this aspect and all other aspects provided herein, the at least one symptom is selected from the group consisting of: skeletal and craniofacial dysmorphism, liver dysfunction, progressive sensorineural hearing loss and retinopathy.

In another embodiment of this aspect and all other aspects provided herein, the at least one bacterium expresses each of membrane-bound PQQ-dependent glucose dehydrogenase (mGDH), ubiquinol-cytochrome c reductase iron-sulfur subunit, TonB-dependent receptor, carbon-nitrogen hydrolase, and ubiquinol oxidase subunit II.

In another embodiment of this aspect and all other aspects provided herein, the at least one bacterium produces one or more of gluconic acid, 2-keto-gluconic acid, 5-keto-gluconic acid, and/or 2,5-diketo-D-gluconic acid.

In another embodiment of this aspect and all other aspects provided herein, the at least one bacterium produces each of gluconic acid, 2-keto-gluconic acid, 5-keto-gluconic acid, and/or 2,5-diketo-D-gluconic acid.

Also provided herein, in another aspect, is a method for increasing the biogenesis of cellular mitochondria or peroxisomes, the method comprising administering to a subject, a composition comprising an amount of at least one bacterium that comprises and expresses one or more nucleic acid sequences encoding membrane-bound PQQ-dependent glucose dehydrogenase (mGDH), ubiquinol-cytochrome c reductase iron-sulfur subunit, TonB-dependent receptor, carbon-nitrogen hydrolase, and ubiquinol oxidase subunit II, or a fraction or extract thereof, effective to increase the biogenesis of cellular mitochondria or peroxisomes.

In one embodiment of this aspect and all other aspects provided herein, the size and/or number of peroxisomes is increased.

In one embodiment of this aspect and all other aspects provided herein, mitochondrial activity is increased.

In another embodiment of this aspect and all other aspects provided herein, the at least one bacterium expresses each of encoding membrane-bound PQQ-dependent glucose dehydrogenase (mGDH), ubiquinol-cytochrome c reductase iron-sulfur subunit, TonB-dependent receptor, carbon-nitrogen hydrolase, and ubiquinol oxidase subunit II.

In another embodiment of this aspect and all other aspects provided herein, the at least one bacterium produces one or more of gluconic acid, 2-keto-gluconic acid, 5-keto-gluconic acid, and/or 2,5-diketo-D-gluconic acid.

In another embodiment of this aspect and all other aspects provided herein, the at least one bacterium produces each of gluconic acid, 2-keto-gluconic acid, 5-keto-gluconic acid, and/or 2,5-diketo-D-gluconic acid.

Also provided herein, in another aspect, is a method of treating Alzheimer's disease, the method comprising administering to a subject having Alzheimer's disease, a composition comprising a therapeutically effective amount of at least one bacterium that comprises and expresses one or more nucleic acid sequences encoding one or more of membrane-bound PQQ-dependent glucose dehydrogenase (mGDH), ubiquinol-cytochrome c reductase iron-sulfur subunit, TonB-dependent receptor, carbon-nitrogen hydrolase, and ubiquinol oxidase subunit II, or an extract or fraction thereof, thereby reducing at least one symptom of Alzheimer's disease.

In one embodiment of this aspect and all other aspects provided herein, the at least one bacterium expresses each of membrane-bound PQQ-dependent glucose dehydrogenase (mGDH), ubiquinol-cytochrome c reductase iron-sulfur subunit, TonB-dependent receptor, carbon-nitrogen hydrolase, and ubiquinol oxidase subunit II.

In another embodiment of this aspect and all other aspects provided herein, the at least one bacterium produces one or more of gluconic acid, 2-keto-gluconic acid, 5-keto-gluconic acid, and/or 2,5-diketo-D-gluconic acid.

In another embodiment of this aspect and all other aspects provided herein, the at least one bacterium produces each of gluconic acid, 2-keto-gluconic acid, 5-keto-gluconic acid, and/or 2,5-diketo-D-gluconic acid.

In another embodiment of this aspect and all other aspects provided herein, the at least one symptom is selected from the group consisting of: cognitive decline, confusion, delusion, disorientation, forgetfulness, difficulty concentrating, inability to generate new memories, inability to do simple math, inability to recognize common items, aggression, agitation, irritability, meaningless repetition of own words, personality changes, restlessness, lack of restraint, wandering, anger, apathy, general discontent, loneliness, mood swings, depression, hallucination, paranoia, loss of appetite, inability to combine muscle movements and jumbled speech.

In another embodiment of this aspect and all other aspects provided herein, the bacterium is *Gluconobacter* EBT 405.

Another aspect provided herein relates to the use of a composition comprising gluconic acid, 2-keto-gluconic acid, 5-keto-gluconic acid, and/or 2,5-diketo-D-gluconic acid for the treatment of Parkinson's disease or Alzheimer's disease.

Another aspect provided herein relates to the use of composition as described herein in the treatment of Parkinson's disease or Alzheimer's disease.

Another aspect provided herein relates to the use of a composition comprising gluconic acid, 2-keto-gluconic acid, 5-keto-gluconic acid, and/or 2,5-diketo-D-gluconic acid for increasing cellular ATP production.

Another aspect provided herein relates to the use of a composition as described herein for increasing cellular ATP production.

Another aspect provided herein relates to the use of a composition comprising gluconic acid, 2-keto-gluconic acid, 5-keto-gluconic acid, and/or 2,5-diketo-D-gluconic acid for treating a mitochondrial electron transport chain disorder or a peroxisomal disorder.

Another aspect provided herein relates to the use of a composition as described herein for the treatment of a mitochondrial electron transport chain disorder or a peroxisomal disorder.

Another aspect provided herein relates to the use of a composition comprising gluconic acid, 2-keto-gluconic acid, 5-keto-gluconic acid, and/or 2,5-diketo-D-gluconic acid for increasing cellular biogenesis of mitochondria or peroxisomes.

Another aspect provided herein relates to the use of a composition as described herein for increasing cellular biogenesis of mitochondria or peroxisomes.

Another aspect provided herein relates to the use of a composition comprising gluconic acid, 2-keto-gluconic acid, 5-keto-gluconic acid, and/or 2,5-diketo-D-gluconic acid for increasing the expression and/or activity of TFAM or peroxisome proliferator activated receptor gamma coactivator 1 (PGC-1).

Another aspect provided herein relates to the use of a composition of as described herein for increasing the expression and/or activity of TFAM or peroxisome proliferator activated receptor gamma coactivator 1 (PGC-1).

Another aspect provided herein relates to the use of a composition comprising a measured amount of one or more bacterium that comprises and expresses one or more nucleic acid sequences encoding one or more of membrane-bound PQQ-dependent glucose dehydrogenase (mGDH), ubiquinol-cytochrome c reductase iron-sulfur subunit, TonB-dependent receptor, carbon-nitrogen hydrolase, and ubiquinol oxidase subunit II for the treatment or prevention of Alzheimer's disease or Parkinson's disease.

In one embodiment of this aspect and all other aspects provided herein, the one or more bacterium comprises *Gluconobacter* EBT 405.

Definitions

The terms "patient," "subject" and "individual" are used interchangeably herein, and refer to an animal, particularly a human, to whom treatment, including prophylactic treatment is provided. The term "subject" as used herein refers to human and non-human animals. The term "non-human animals" and "non-human mammals" are used interchangeably herein and includes all vertebrates, e.g., mammals, such as non-human primates, (particularly higher primates), sheep, dog, rodent (e.g. mouse or rat), guinea pig, goat, pig, cat, rabbits, cows, and non-mammals such as chickens, amphibians, reptiles etc. In one embodiment, the subject is human. In another embodiment, the subject is an experimental animal or animal substitute as a disease model. In another embodiment, the subject is a domesticated animal including companion animals (e.g., dogs, cats, rats, guinea pigs, hamsters etc.). It is specifically contemplated herein that a subject can be of any developmental age including, but not limited to, a fetus, a neonate, an infant, a toddler, a child, an adolescent, an adult, post-menopausal, or a geriatric subject.

As used herein, a "prebiotic" refers to an ingredient that allows or promotes specific changes, both in the composition and/or activity in the gastrointestinal microbiota that may (or may not) confer benefits upon the host. In some embodiments, a prebiotic can include one or more of the following: fructooligosaccharide, galactooligosaccharides, hemicelluloses (e.g., arabinoxylan, xylan, xyloglucan, and glucomannan), inulin, chitin, lactulose, mannan oligosaccharides, oligofructose-enriched inulin, gums (e.g., guar gum, gum arabic and carrageenan), oligofructose, oligodextrose, tagatose, resistant maltodextrins (e.g., resistant starch), trans-galactooligosaccharide, pectins (e.g., xylogalactouronan, citrus pectin, apple pectin, and rhamnogalacturonan-I), dietary fibers (e.g., soy fiber, sugar beet fiber, pea fiber, corn bran, and oat fiber) and xylooligosaccharides.

As used herein, the terms "administering," "introducing" and "transplanting" are used interchangeably in the context of the placement of cells, e.g., a bacterial composition, as described herein into a subject, by a method or route which results in at least partial localization of the introduced cells at a desired site, such as the intestines or a region thereof, such that a desired effect(s) is produced (e.g., increased mitochondrial ATP production). The cells can be administered by any appropriate route which results in delivery to a desired location in the subject where at least a portion of the delivered cells or components of the cells remain viable. The period of viability of the cells after administration to a subject can be as short as a few hours, e.g., six to twenty-four hours, to a few days, to as long as several years, i.e., long-term engraftment. In some embodiments, the term "administering" refers to the administration of a bacterial extract or preparation comprising one or more bacterial metabolites and/or byproducts but lacking fully viable bacterial cells.

As used herein "preventing" or "prevention" refers to any methodology where the disease state does not occur due to the actions of the methodology (such as, for example, administration of a composition as described herein). In one aspect, it is understood that prevention can also mean that the disease is not established to the extent that occurs in untreated controls. For example, there can be a 5, 10, 15, 20, 25, 30, 35, 40, 50, 60, 70, 80, 90, or 100% reduction in the establishment of disease frequency relative to untreated controls. Accordingly, prevention of a disease encompasses a reduction in the likelihood that a subject will develop the disease, relative to an untreated subject (e.g. a subject who is not treated with a composition as described herein).

"Synergy" or "synergistic interactions" refers to the interaction or cooperation of two or more microbes or metabolites to produce a combined effect greater than the sum of their separate effects. For example, in one embodiment, "synergy" between two or more microbes can result from a first microbe secreting a waste product or metabolite that the second microbe uses to fuel growth or other processes.

The terms "decrease", "reduced", "reduction", or "inhibit" are all used herein to mean a decrease or lessening of a property, level, or other parameter by a statistically significant amount. In some embodiments, "reduce," "reduction" or "decrease" or "inhibit" typically means a decrease by at least 10% as compared to a reference level (e.g., the absence of a given treatment) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to a reference level. A decrease can be preferably down to a level accepted as within the range of normal for an individual without a given disorder.

The terms "increased," "increase" or "enhance" or "activate" are all used herein to generally mean an increase of a property, level, or other parameter by a statistically significant amount; for the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, at least about a 20-fold increase, at least about a 50-fold increase, at least about a 100-fold increase, at least about a 1000-fold increase or more as compared to a reference level.

The term "pharmaceutically acceptable" can refer to compounds and compositions which can be administered to a subject (e.g., a mammal or a human) without undue toxicity.

As used herein, the term "pharmaceutically acceptable carrier" can include any material or substance that, when combined with an active ingredient, allows the ingredient to retain biological activity and is substantially non-reactive with the subject's immune system (unless desired). Examples include, but are not limited to, any of the standard pharmaceutical carriers such as a phosphate buffered saline solution, emulsions such as oil/water emulsion, and various types of wetting agents. The term "pharmaceutically acceptable carriers" excludes tissue culture and bacterial culture media.

As used herein, the term "comprising" means that other elements can also be present in addition to the defined elements presented. The use of "comprising" indicates inclusion rather than limitation.

As used herein the term "consisting essentially of" refers to those elements required for a given embodiment. The term permits the presence of additional elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

Further, unless otherwise required by context, singular terms shall include pluralities and plural terms shall include the singular.

Other than in the operating examples, or where otherwise indicated, all numbers expressing quantities of ingredients or reaction conditions used herein should be understood as modified in all instances by the term "about." The term "about" when used in connection with percentages can mean±1%.

BRIEF DESCRIPTION OF THE FIGURES

FIGS. 1A-1H. FIG. 1A, *Gluconoacetobacter* feeding suppresses the developmental delay phenotype of spg-7 (ad2249), nduf-7(et7), and gas-1(fc21) mutants. FIG. 1B, *Gluconoacetobacter* feeding increases ATP content in wild-type animals compared to worms fed on *E. coli* OP50-1 as assessed using a strain that expresses Luciferase in all somatic cells. FIG. 1C, *Gluconoacetobacter* feeding increases ATP content in wildtype animals compared to worms fed on *E. coli* OP50-1 as assessed by measuring the endogenous ATP levels using biochemical method. FIG. 1D, *Gluconoacetobacter* feeding restores the ATP content in spg-7(ad2249) animals to wildtype levels. FIG. 1E, *Gluconoacetobacter* feeding restores the ATP content in nduf-7(et7) animals to wildtype levels. FIG. 1F, *Gluconoacetobacter* feeding increases the mitochondrial membrane potential in spg-7(ad2249), nduf-7(et7), and gas-1(fc21) mutants animals compared to the corresponding mutant worms fed on *E. coli* OP50-1 as assessed using MitoTracker Red CMXRos. FIG. 1G, Animals fed on *Gluconacetobacter* spp and treated with varying doses of paraquat had significantly higher levels of bioluminescence, a surrogate for ATP levels, compared to animals fed on *E. coli* OP50 and treated with paraquat. FIG. 1H, Animals fed on *Gluconacetobacter* spp and treated with varying doses of rotenone had significantly higher levels of bioluminescence, a surrogate for ATP levels, compared to animals fed on *E. coli* OP50 and treated with rotenone.

FIGS. 2A-2K. FIG. 2A, Worms fed *E. coli* OP50 and treated with either MPP+ or 6-OHDA or paraquat induced mitochondrial stress reporter hsp-6::gfp expression while worms fed on *Gluconacetobacter* spp failed to induce the GFP expression. FIG. 2B, Feeding spg-7(ad2249); tbb-6::gfp animals on *Gluconacetobacter* spp suppressed the activation of tbb-6::gfp expression. FIG. 2C, *Gluconoacetobacter* feeding suppresses hphd-1::gfp expression. FIG. 2D, *Gluconoacetobacter* feeding increases B0303.3::gfp expression. FIG. 2E, *Gluconoacetobacter* feeding increases prx-11::gfp expression. FIG. 2F, tcer-1(RNAi) suppresses the induction of cpt-2::gfp in worms fed on *Gluconoacetobacter* spp. FIG. 2G, nhr-49(RNAi) suppresses the induction of acox-1.2::gfp in worms fed on *Gluconoacetobacter* spp. FIG. 2H, tcer-1 (RNAi) suppresses the induction of ech-1.2::gfp in worms fed on *Gluconoacetobacter* spp. FIG. 2I, nhr-49(RNAi) suppresses the induction of acdh-7::gfp in worms fed on *Gluconoacetobacter* spp. FIG. 2J, nhr-49 (RNAi) suppresses the induction of pmp-4::gfp in worms fed on *Gluconoacetobacter* spp. FIG. 2K, nhr-49(RNAi) suppresses the induction ofprx-6::gfp in worms fed on *Gluconoacetobacter* spp.

FIGS. 3A-3H. FIG. 3A, tcer-1(tm1452) and nhr-49 (nr2041) animals fed on *Gluconacetobacter* spp feeding grew slower compared to wildtype worms fed on *Gluconacetobacter* spp. FIG. 3B, RNAi of tcer-1, nhr-49, and prx-5 suppressed the *Gluconacetobacter* spp feeding induced increase in bioluminescence phenotype. FIG. 3C, nhr-49 (RNAi) suppressed the accelerated developmental progression phenotype of spg-7(ad2249) and nduf-7(et19) mutant worms fed on *Gluconacetobacter* spp. FIG. 3D, prx-5 (RNAi) suppressed the accelerated developmental progression phenotype of spg-7(ad2249) and nduf-7(et19) mutant worms fed on *Gluconacetobacter* spp. FIG. 3E, nhr-49 (RNAi) exacerbated the reduced mitochondrial membrane potential of spg-7(ad2249) mutants as assessed using Mito CMXRos. FIG. 3F, Representative picture showing the fused mitochondria phenotype in the muscle of worms fed on *Gluconacetobacter* spp compared to the worms fed on *E. coli* OP50 as assessed using a mitochondrially targeted TOM20-RFP fusion protein. FIG. 3G, Representative picture showing increased punctate structures in the intestine of worms fed on *Gluconacetobacter* spp indicating an increase in peroxisomes as assessed using the peroxisomally targeted GFP-DAF-22 fusion protein. FIG. 3H, Worms fed on *Gluconacetobacter* spp had slightly lower levels of $H_2O_2$ indicating that *Gluconacetobacter* spp as assessed using transgenic worms expressing HyPer sensor.

FIGS. 4A-4I. FIG. 4A, Worms fed on *Gluconacetobacter* spp had significantly higher levels of bioluminescence, a surrogate for ATP levels, compared to animals fed on *E. coli* OP50 as the worms age. FIG. 4B, Dilution of *Gluconacetobacter* spp with *E. coli* induces significantly higher levels of bioluminescence, a surrogate for ATP levels. FIG. 4C, *Gluconacetobacter* strains including *Gluconacetobacter hanseni* (MGH isolate), the canonical *Gluconacetobacter hanseni* ATCC 23769, and non-cellulose producing mutant of *G. hanseni* ATCC 23769 induces significantly higher levels of bioluminescence, a surrogate for ATP levels compared worms fed on *E. coli* OP50. FIG. 4D, Members of Acetobacteraceae induce significantly higher levels of bioluminescence, a surrogate for ATP levels, compared worms fed on *E. coli* OP50. FIG. 4E, Worms fed on mutants in membrane-bound PQQ-dependent glucose dehydrogenase, cytochrome o ubiquinol oxidase subunit II, and ubiquinol-cytochrome c reductase iron-sulfur subunit have lower levels of bioluminescence, a surrogate for ATP levels, compared to worms fed on wildtype *G. oxydans*. FIG. 4F, ATP production was decreased in worms fed on deletion mutations in Membrane-bound PQQ-dependent glucose dehydrogenase, FAD-dependent Membrane-bound dehydrogenase, and Membrane-bound PQQ-dependent dehydrogenase 3 compared to worms fed on wildtype *G. oxydans*. FIG. 4G, PGC-1α gene expression was increased in human primary dermal fibroblasts exposed to *Gluconacetobacter* spp compared to mock-treated cells as assessed by RT-PCR. FIG. 4H, TFAM gene expression was increased in human primary dermal fibroblasts exposed to *Gluconacetobacter* spp compared to mock-treated cells as assessed by RT-PCR. FIG. 4I, mtDNA copy numbers were increased in human primary dermal fibroblasts exposed to *Gluconacetobacter* spp compared to mock-treated cells.

FIGS. 5A-5I. FIG. 5A, *Gluconacetobacter* spp, *Acetobacter* spp, and *Gluconobacter* spp suppresses the developmental delay phenotype of spg-7(ad2249). FIG. 5B, *Gluconacetobacter* spp, *Acetobacter* spp, and *Gluconobacter* spp accelerates the developmental growth rate of wildtype animals compared to the worms fed on *E. coli* OP50-1. FIG. 5C, Representative picture showing the accelerated developmental growth of wildtype worms fed on *Gluconacetobacter* spp. FIG. 5D, Wildtype worms fed on *Gluconacetobacter* spp are slightly longer compared to the worms fed on *E. coli* OP50-1. *Gluconacetobacter* spp feeding reduces the time taken for animals to reach egg-laying adult stage from L1-larval stage. FIG. 5E, *Gluconacetobacter* spp feeding reduces the time taken for animals to reach egg-laying adult stage from L4-larval stage. FIG. 5F, *Gluconacetobacter* spp induces increase in bioluminescence, a surrogate for ATP production, within 6 hours of initiating feeding with maximal levels by 18 hours of feeding spg-7(ad2249) mutants fed on *Gluconacetobacter* spp had significantly increased mitochondrial membrane potential compared to animals fed on *E. coli* OP50 as assessed using TMRE dye. FIG. 5G, Animals fed on *Gluconacetobacter* spp and treated with rotenone or paraquat or sodium azide had significantly higher levels of bioluminescence, a surrogate for ATP levels, compared to animals fed on *E. coli* OP50 and treated with rotenone or paraquat or sodium azide. FIG. 5H, spg-7 (ad2249) mutants fed on *Gluconacetobacter* spp. had significantly increased mitochondrial membrane potential compared to animals fed on *E. coli* OP50 as assessed using TMRE dye. FIG. 5I, Animals fed on *Gluconacetobacter* spp and treated with rotenone or paraquaqt or sodium azide had significantly higher levels of bioluminescence, a surrogate for ATP levels, compared to animals fed on *E. coli* OP50 and treated with rotenone or paraquat or sodium azide.

FIGS. 6A-6L. FIG. 6A, Animals fed on *Gluconacetobacter* spp were more resistant to rotenone or paraquat than animals fed on *E. coli* OP50. FIG. 6B, Feeding spg-7 (ad2249); tbb-6::gfp animals on *Gluconacetobacter* spp suppressed the activation of tbb-6::gfp expression. FIGS. 6C-6G, *Gluconoacetobacter* feeding increases cpt-2::gfp (FIG. 6C), acox-1.2::gfp (FIG. 6D), pmp-4::gfp (FIG. 6E), acdh-7::gfp (FIG. 6F), ech-1.2::gfp (FIG. 6G) expression compared to worms fed on *E. coli* OP50. FIG. 6H, Representative figure showing the increased expression of B0303. 3::gfp in worms fed on *Gluconoacetobacter* compared to fed on *E. coli* OP50. FIG. 6I, Representative figure showing the increased expression of acdh-7::gfp in worms fed on *Gluconoacetobacter* compared to fed on *E. coli* OP50. FIG. 6J, Representative figure showing the increased expression of acox-1.2::gfp in worms fed on *Gluconoacetobacter* compared to those fed on *E. coli* OP50. FIG. 6K, Representative figure showing the increased expression of cpt-1::gfp in worms fed on *Gluconoacetobacter* compared to fed on *E. coli* OP50. FIG. 6L, Representative figure showing no change in expression of rpt-3::gfp in worms fed on *Gluconoacetobacter* compared to fed on *E. coli* OP50.

FIGS. 7A-7H. FIG. 7A, Representative figure showing the increased expression of icl-1::gfp in worms fed on *Gluconoacetobacter* compared to worms fed on *E. coli* OP50. FIG. 7B, *Gluconoacetobacter* feeding does not affect fat-7::gfp expression. FIG. 7C, Representative figure showing that *Gluconoacetobacter* feeding does not affect UbV-gfp expression while treatment with Bortezomib stabilizes UbV-gfp. FIG. 7D, Representative figure showing that *Gluconoacetobacter* feeding does not induce autophagy while starvation induces autophagy as assessed using the lgg-1::GFP strain. FIG. 7E, Intestine-specific overexpression of nhr-49 was sufficient to accelerate growth rate of nhr-49 (nr2041) mutants fed on *Gluconacetobacter* spp. FIG. 7F, Representative figure showing that the nhr-49 gene expression was induced in the worms fed on *Gluconacetobacter* spp as assessed using a nhr-49::GFP transcriptional fusion. FIG. 7G, Representative figure showing that TCER-1::GFP expression is increased in the intestinal cell nuclei compared to worms fed on *E. coli* OP50. FIG. 7H, Representative figure showing that *Gluconoacetobacter* feeding induces mitochondrial fusion in the hypodermis of worms compared to worms fed on *E. coli* OP50 as assessed using Rhodamine 6G dye, which stains mitochondria.

FIGS. 8A-8H. FIG. 8A, Representative figure showing that *Gluconoacetobacter* feeding does not restore the peroxisomal targeting defect in prx-5(RNAi) treated worms. FIG. 8B, Representative figure showing that *Gluconoacetobacter* feeding does not affect the golgi morphology or distribution as assessed by a transgenic strain that targets GFP to the golgi. FIG. 8C, Representative figure showing that *Gluconoacetobacter* feeding does not affect the gut lysosomal morphology or distribution as assessed by a transgenic strain that targets GFP to the lysosomes. FIG. 8D, Representative figure showing that *Gluconoacetobacter* feeding does not affect the Endoplasmic Reticulum (ER) morphology or distribution as assessed by a transgenic strain that targets GFP to the ER. FIG. 8E, Worms fed on *Gluconacetobacter* spp and treated with $H_2O_2$ had lower levels of $H_2O_2$ compared to the worms fed on *E. coli* OP50 as assessed using the Amplex red assay. FIG. 8F, Glutathione intracellular concentrations were not affected in worms fed on *Gluconoacetobacter* spp compared to worms fed on *E. coli* OP50. FIG. 8G, Representative figure showing the Halo formation around colonies in $CaCO_3$ media plates produced by different members of Acetobacteraceae. FIG. 8H, *Gluconobacter oxydans* transposon mutants failed to suppress the slow developmental growth phenotype of *C. elegans* spg-7(ad2249).

FIG. 9A, Representative figure showing the *Gluconobacter oxydans* transposon mutants that failed to suppress the slow developmental growth phenotype of wild-type animals. FIG. 9B, Mutants in membrane-bound PQQ-dependent glucose dehydrogenase, cytochrome o ubiquinol oxidase subunit II, ubiquinol-cytochrome c reductase iron-sulfur subunit, and carbon-nitrogen hydrolase fail to form clear halo around media plates containing $CaCO_3$. FIG. 9C, Deletion alleles in various dehydrogenases and found that spg-7(ad2249) mutant worms fed on deletion mutations in Membrane-bound PQQ-dependent glucose dehydrogenase, FAD-dependent Membrane-bound dehydrogenase, and Membrane-bound PQQ-dependent dehydrogenase 3 grew slower compared to worms fed on wildtype *G. oxydans* FIG. 9D, Exposure of *E. coli* OP50 to human primary dermal fibroblasts results in significant reduction in the ATP production while *Gluconacetobacter* spp does not affect ATP production compared to the mock-treated cells. FIG. 9E, *Gluconoacetobacter* spp does not reduce the cellular ATP production even at higher doses of the bacteria.

FIG. 10A, Transgenic worms expressing human α-synuclein and GFP in the dopaminergic neurons were fed with *E. coli* op50 or EBT405 from first larval stage and subjected to Rotenone treatment at the L4-larval stage. Arrows show the axons of CEP neurons. In the rotenone treated animals, the CEP neurons are degenerating or lost. FIG. 10B, Quantification of the CEP neuron loss. Three independent trials were performed and each trial consisted of 20-30 animals.

DETAILED DESCRIPTION

Figure 9A:
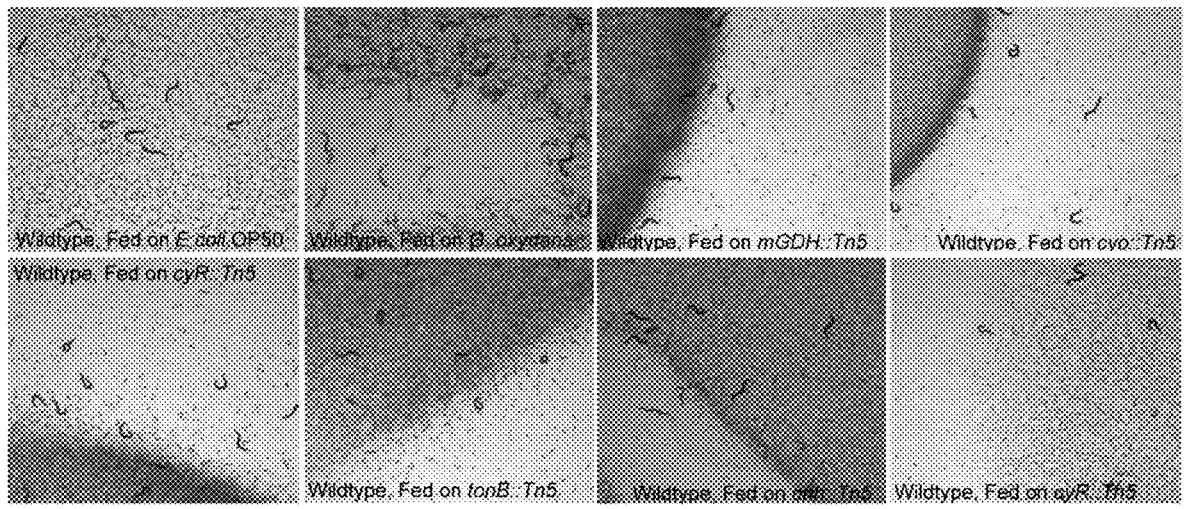
FIGS. 9A-9E.
Figure 9B:
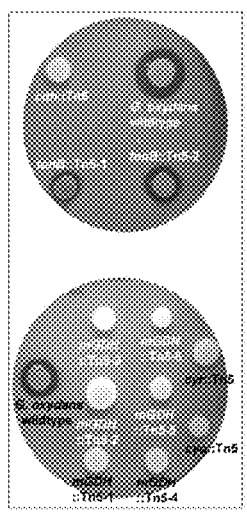

Provided herein are methods and compositions for the treatment or prevention of diseases and/or disorders involving or characterized by mitochondrial dysfunction and/or peroxisomal dysfunction. Such compositions comprise one or more bacterial species from the Acetobacteriaceae family or a bacterial extract or component derived therefrom.

Mitochondrial Function/Dysfunction and Production of Intracellular ATP

Mitochondria are intracellular organelles present in most eukaryotic cells, which primarily function to produce energy, in the form of ATP, through oxidative phosphorylation for use in a multitude of cellular processes. For example, energy derived from the metabolism of glucose or fatty acids is converted to ATP, which is then used to drive various energy-requiring biosynthetic reactions and other metabolic activities. Mitochondria have their own genomes, separate from nuclear DNA, comprising circular, double-stranded DNA with about 16,000 base pairs in human cells. Each mitochondrion may have multiple copies of its genome, and individual cells may have hundreds of mitochondria. Mitochondria play a role in the tricarboxylic acid (TCA) cycle, heme synthesis, β-oxidation of fatty acids, amino acid metabolism, and the like. Moreover, functions for maintaining calcium homeostasis, an active oxygen production system, and transport systems for metabolites, ions, proteins, and the like are present in mitochondria. Hence, mitochondria play an important role in both catabolic and anabolic reactions in eukaryotic cells.

It has been shown that mitochondrial dysfunction can contribute to a variety of diseases. Some mitochondrial diseases are due to mutations or deletions in the mitochondrial genome. Mitochondria divide and proliferate with a faster turnover rate than their host cells, and their replication is under control of the nuclear genome. Thus, if a threshold proportion of mitochondria in a cell are defective, and if a threshold proportion of such cells within a tissue have defective mitochondria, symptoms of tissue or organ dysfunction can result. Practically any tissue can be affected, and a large variety of symptoms may be present, depending on the extent to which different tissues are involved.

Diseases of the mitochondria are apparent most often in organs that have a high energy demand, such as the brain, heart, liver, skeletal muscles, kidney and the endocrine and respiratory systems. Even a mild impairment in mitochondrial function can be reflected by symptoms of disease. Symptoms of a mitochondrial disease can include loss of motor control, muscle weakness and pain, seizures, visual/hearing problems, cardiac diseases, liver diseases, gastrointestinal disorders, swallowing difficulties and more. A mitochondrial disease can be inherited or can be due to spontaneous mutations, either of which can lead to altered functions of the proteins or RNA molecules normally residing in the mitochondria.

It is important to note that the bacterial compositions, extracts and/or components described herein will have the greatest effect in cells, tissues, organs, etc. of a subject who retains at least some mitochondrial activity, even if the activity is impaired. While the bacterial compositions, extracts and/or components described herein can induce both mitochondrial and peroxisomal biogenesis (thereby enhancing total cellular metabolic function), the benefit of the compositions described herein is thought to be due to an enhancement of existing mitochondrial function through the electron transport chain. That is, the compositions described herein do not provide an exogenous gene for repair of mitochondrial dysfunction, but rather will enhance the existing function of mitochondria by either increasing the number of mitochondria and/or the function of the electron transport chain within each mitochondrion. This enhancement of function is likely due, in part, to the metabolites generated by the bacteria as described herein.

Disorders associated with impaired mitochondrial function also include, for example, metabolic disorders, neurodegenerative disorders, aging related disorders and chronic inflammatory disorders. Mitochondrial disorders can also include diseases with inherited and/or acquired mitochondrial dysfunction, such as Charcot-Marie-Tooth Disease Type 2A2, Mitochondrial Encephalopathy Lactic Acidosis and Stroke (MELAS), Leigh syndrome, Barth syndrome, Leber's optic neuropathy, fatty acid oxidation disorders, inherited forms of deafness and blindness, metabolic abnormalities induced by exposure to toxic chemicals and/or drugs (e.g., cisplatin induced deafness).

To reiterate, the methods and compositions described herein are not intended to cure diseases or disorders with impaired mitochondrial function but rather are useful in reducing at least one symptom of disease that is associated with impaired mitochondrial function. That is, while the compositions described herein cannot correct an inherited mitochondrial defect, they can be used to enhance mitochondrial function that is present in the cell despite the presence of disease. This can be achieved, for example, by increasing mitochondrial number or increasing flux through the electron transport chain (e.g., at complex I and complex III). Thus, in one embodiment, a subject to be treated with the compositions and methods described herein retains at least 10% mitochondrial and/or peroxisomal function as (prior to treatment) as compared to a non-affected subject. In other embodiments, the subject retains at least 20%, at least 30%, at least 40%, at least 50%, at least 60%, at least 70%, at least 80%, at least 90%, at least 95%, or at least 99% mitochondrial and/or peroxisomal function (prior to treatment) as compared to a non-affected individual.

It is also contemplated herein that individuals who retain normal mitochondrial and/or peroxisomal function can be treated to enhance mitochondrial function to enhance performance, for example, athletic performance.

In certain embodiments, the methods and compositions described herein can increase mitochondrial and/or peroxisomal function by at least 10% (e.g., as assessed by measuring ATP production) compared to the mitochondrial and/or peroxisomal function prior to such treatment. In some embodiments, mitochondrial and/or peroxisomal function is increased by at least 20%, at least 30%, at least 40%, at least 50%, at least 60%, at least 70%, at least 80%, at least 90%, at least 95%, at least 99%, at least 1-fold, at least 2-fold, at least 5-fold, at least 10-fold, at least 20-fold, at least 50-fold, at least 100-fold, at least 1000-fold or more as compared to the mitochondrial and/or peroxisomal function prior to such treatment.

Deficiencies in the Electron Transport Chain: Many diseases have been found to involve a mitochondrial deficiency such as a Complex I, II, III or IV impairment or an enzyme deficiency e.g. pyruvate dehydrogenase impairment. Complex I, II, III and IV are protein complexes embedded in the inner membrane of the mitochondrion. They are known as the respiratory chain and function by coupling electron transfer between an electron donor (such as NADH) and an electron acceptor (such as $O_2$) with the transfer of H+ ions. The resulting electrochemical proton gradient over the inner membrane is used to generate chemical energy in the form of adenosine triphosphate (ATP) by oxidation of glucose, pyruvate and NADH, which all are produced in the cytosol of the cell. This process of cellular respiration, also known as aerobic respiration, is dependent on the presence of oxygen. When oxygen is limited, the glycolytic products will be metabolized by anaerobic fermentation, a process that is independent of the mitochondria. The production of ATP from glucose is about 13 times higher during aerobic respiration compared to fermentation.

Complexes I-IV carry electrons along four series of reactions, known as the Electron Transport Chain, resulting in energy production. A fifth group (Complex V) is an ATP synthase enzyme that generates ATP. Together, the electron transport chain and the ATP synthase form the respiratory chain and the entire process is known as oxidative phosphorylation or OXPHOS.

Complex I deficiency: Complex I, the first step in this chain, is the most common site for mitochondrial abnormalities, representing as much as one third of the respiratory chain deficiencies. Often presenting at birth or in early childhood, Complex I deficiency is usually a progressive neuro-degenerative disorder and is responsible for a variety of clinical symptoms, particularly in organs and tissues that require high energy levels, such as brain, heart, liver, and skeletal muscles. A number of specific mitochondrial disorders have been associated with Complex I deficiency including: Leber's hereditary optic neuropathy (LHON), mitochondrial myopathy, encephalopathy, lactic acidosis and stroke (MELAS), myoclonic epilepsy with ragged red fibers (MERRF), and Leigh Syndrome (LS).

To date, three major forms of Complex I deficiency have been identified: i) Fatal infantile multisystem disorder—characterized by poor muscle tone, developmental delay, heart disease, lactic acidosis, and respiratory failure; ii) Myopathy (muscle disease)—starting in childhood or adulthood, and characterized by weakness or exercise intolerance; and iii) Mitochondrial encephalomyopathy (brain and muscle disease)—beginning in childhood or adulthood and involving variable symptom combinations, which can include: eye muscle paralysis, pigmentary retinopathy (retinal color changes with loss of vision), hearing loss, sensory neuropathy (nerve damage involving the sense organs), seizures, dementia, ataxia (abnormal muscle coordination), and involuntary movements. This form of Complex I deficiency may cause Leigh Syndrome and MELAS. Most cases of Complex I deficiency result from autosomal recessive inheritance (combination of defective nuclear genes from both the mother and the father). Less frequently, the disorder is maternally inherited or sporadic and the genetic defect is in the mitochondrial DNA.

In one embodiment, the compositions and methods described herein increase intracellular ATP levels by at least 10%, at least 20%, at least 25%, at least 30%, at least 40%, at least 50%, at least 60%, at least 70%, at least 80%, at least 90%, at least 95%, at least 98%, at least 99%, at least 1-fold, at least 2-fold, at least 5-fold, at least 10-fold, at least 20 fold, at least 100-fold, at least 1000-fold or more compared to the level of intracellular ATP in a substantially similar cell or cell population, with the exception that the reference cells are not contacted with the compositions or metabolites described herein. In one embodiment, the compositions and methods described herein restore intracellular ATP levels in a subject having mitochondrial dysfunction relative to a subject (or group of subjects) not treated with such compositions and methods.

Metabolic Disorders: Metabolic disorders include, for example, type II diabetes, obesity, hyperglycemia, glucose intolerance, insulin resistance (i.e., hyperinsulinemia, metabolic syndrome, syndrome X), hypercholesterolemia, hypertension, hyperlipoproteinemia, hyperlipidemia (e.g., dyslipidemia), hypertriglyceridemia, cardiovascular disease, atherosclerosis, peripheral vascular disease, kidney disease, ketoacidosis, thrombotic disorders, nephropathy, diabetic neuropathy, diabetic retinopathy, sexual dysfunction, dermatopathy, dyspepsia, hypoglycemia, metabolic syndrome, cancer or edema. While the methods and compositions described herein may not address the underlying cause(s) of such diseases or disorders, the promotion of mitochondrial function provided by such methods and compositions can ameliorate those aspects of these diseases or disorders that are related to mitochondrial dysfunction or insufficiency.

In one embodiment of the methods and compositions provided herein, the subject is suffering from or is susceptible to developing a metabolic disorder. Subjects suffering from or at risk of developing a metabolic disorder are identified by methods known in the art. For example, diabetes can be diagnosed by measuring e.g., fasting blood glucose levels or insulin or by a glucose tolerance test. Normal adult glucose levels are 60-126 mg/dl. Normal insulin levels are 7 mU/mL±3 mU. Glucose intolerance is diagnosed by a two-hour glucose level of 140 to 199 mg per dL (7.8 to 11.0 mmol) on the 75-g oral glucose tolerance test. Insulin resistance is diagnosed by a fasting serum insulin level of greater than approximately 60 pmol/L. Hypoglycemia can be diagnosed by a blood glucose level lower than 2.8 to 3.0 mmol/L (50 to 54 mg/dl). Hypertension can be diagnosed by a blood pressure consistently at or above 140/90. Cardiovascular disease can be diagnosed, at least in part, by measuring cholesterol levels (e.g., LDL, HDL, VLDL etc.). For example, LDL cholesterol above 137 or total cholesterol above 200 is indicative of cardiovascular disease. Hyperglycemia is diagnosed by a blood glucose level higher than 10 mmol/l (180 mg/dl). Obesity is diagnosed for example, by body mass index. Alternatively, waist circumference (estimates fat distribution), waist-to-hip ratio (estimates fat distribution), skinfold thickness (if measured at several sites, estimates fat distribution), or bioimpedance (based on principle that lean mass conducts current better than fat mass (i.e., fat mass impedes current), estimates % fat) is measured. The parameters for normal, overweight, or obese individuals are as follows: Underweight: BMI<18.5; Normal: BMI 18.5 to 24.9; Overweight: BMI=25 to 29.9. Overweight individuals are characterized as having a waist circumference of >94 cm for men or >80 cm for women and waist to hip ratios of ≥0.95 in men and ≥0.80 in women. Obese individuals are characterized as having a BMI of 30 to 34.9, being greater than 20% above "normal" weight for height, having a body fat percentage >30% for women and 25% for men, and having a waist circumference >102 cm (40 inches) for men or 88 cm (35 inches) for women. Individuals with severe or morbid obesity are characterized as having a BMI of ≥35.

Neurodegenerative disease: Neurodegenerative disorders include diseases such as dementia, Alzheimer's disease, Parkinson's disease, and Huntington's disease.

In one embodiment, the neurodegenerative disorder is Parkinson's disease. Parkinson's disease (PD) is a neurodegenerative movement disorder characterized by resting tremor, rigidity, bradykinesia, and postural instability. PD symptoms are classically attributed to dopamine depletion and the degeneration of dopaminergic neurons in the substantia nigra pars compacta (SNc). However, additional neuronal circuits are affected, and non-motor symptoms are often present, suggesting a systemic pathology. There is compelling evidence that mitochondrial dysfunction is a primary event in the disease process. It has been reported that PD-related mutations and mitochondrial dynamics have a reciprocal relationship. PD-related mutations can perturb mitochondrial dynamics, and the consequences of these mutations can be modulated by mitochondrial dynamics.

In one embodiment, effective treatment of Parkinson's disease is determined by a reduction in the dose of pharmacological treatments, such as L-DOPA, required to maintain adequate control of symptoms of Parkinson's disease. In another embodiment, efficacy of treatment is monitored using the Unified Parkinson's Disease Rating Scale (UPDRS) as known in the art.

Alzheimer's disease, amyotrophic lateral sclerosis (ALS), Huntington's disease, Friedrich's ataxia, hereditary spastic paraplegia, neurodegeneration with brain iron accumulation (NBIA), and optic atrophy type I are also each associated with various mitochondrial activity deficits (see e.g., Lin et al. Nature 443: 787-795 (2006)).

Inflammatory disease: Chronic inflammatory diseases include disease such as celiac disease, vasculitis, lupus, chronic obstructive pulmonary disease (COPD), irritable bowel disease, atherosclerosis, arthritis, and psoriasis. While the methods and compositions described herein may not address the underlying cause(s) of such diseases or disorders, the promotion of mitochondrial function provided by such methods and compositions can ameliorate those aspects of these diseases or disorders that are related to mitochondrial dysfunction or insufficiency.

Aging: Aging is a progressive accumulation of metabolic and physiologic changes associated with an increasing susceptibility to disease. In the membrane hypothesis of aging (MHA), aging is related to decreasing effectiveness of cellular protective and reparative mechanisms secondary to damage from oxygen radicals. This yields biochemical and metabolic errors which progressively accumulate, resulting in cell aging and ultimately death. Therefore, the MHA suggests that reactive oxygen species (ROS) induced cell membrane structural damage is the primary mediator in cellular aging.

ROS are a normal byproduct of oxidative phosphorylation, and are also formed under conditions of ischemia, hypoperfusion and in response to environmental contaminants. Among the many detrimental activities of ROS, or free oxygen radicals, is direct damage to mitochondrial DNA (mtDNA). Progressive accumulation of mtDNA damage renders cells unable to conduct oxidative phosphorylation reactions effectively, thereby leading to a bioenergetically deficient cell. Over time, mitochondrial DNA damage accumulates and leads to cellular dysfunction with subsequent organ failure, aging and ultimately death. Additionally, there is evidence of a reduction in the oxidant-protective enzymes superoxide dismutase and catalase associated with aging. Thus not only are there increases in the deleterious effects of ROS, but there is a reduction in the enzymes and mitochondrial metabolites necessary for protection from ROS and for effective mitochondrial function.

Peroxisomal Disorders

In some embodiments, the subject has a peroxisomal disorder, with or without the presence of mitochondrial dysfunction.

Peroxisomes are intracellular organelles that are expressed in all eukaryotic cells except erythrocytes and play an important role in intracellular metabolism. Peroxisomes are dynamic organelles that change in shape and numbers based on the specific metabolic needs of different tissues and cell types. Peroxisomes are capable of catabolizing very long chain fatty acids to shorter fatty acids that can then enter the B-oxidation cycle. (VLCFA: carbon chain >22). Peroxisomes also play a role in intracellular antioxidant activity.

Peroxisomes are also involved in the synthesis of lipids such as bile acids, docosohexanoic acid, an omega 3 fatty acid, and plasmalogens, a specialized class of membrane phospholipids. Although a single cell may be able to survive without peroxisomes in certain conditions, this organelle is essential for the proper function and viability of tissues and organs. The importance of peroxisomes is most evident by the group of diseases resulting from the lack of functioning peroxisomes called Peroxisome Biogenesis Disorders or "PBD" (Weller et al., 2003).

In some embodiments, the methods and compositions described herein are not intended to cure peroxisomal diseases or disorders but rather are useful in reducing at least one symptom of disease that is associated with impaired peroxisomal function. That is, while the compositions described herein cannot correct an inherited peroxisomal defect, they can be used to enhance existing peroxisomal function. This can be achieved, for example, by increasing peroxisomal number or increasing flux through the metabolic pathways of the peroxisome (e.g., metabolism of very long chain fatty acids (VLCFA). Thus, in one embodiment, a subject to be treated with the compositions and methods described herein retains at least 10% of the peroxisomal function as compared to the peroxisomal function of a non-affected subject. In other embodiments, the subject retains at least 20%, at least 30%, at least 40%, at least 50%, at least 60%, at least 70%, at least 80%, at least 90%, at least 95%, or at least 99% peroxisomal function as compared to a non-affected individual.

Peroxisome Biogenesis Disorders are a continuum of disorders that are divided into three phenotypes based on the severity of the disorder. Zellweger Syndrome (ZS) is the most severe form; followed by neonatal adrenoleukodystrophy (NALD), an intermediate form, and infantile Refsum disease (IRD), which is the least severe. Children with ZS present early in the neonatal period with profound hypotonia, facial dysmorphisms, liver dysfunction, seizures, and rarely survive past their first year of life. At a biochemical level, laboratory tests show profound deficiencies in peroxisomal metabolism and cells from these patients show near absence of functional cellular peroxisomes. NALD and IRD are more difficult to distinguish from each other, form the majority of cases, and patients can live through adulthood. Both may present soon after birth, but are often diagnosed later by developmental delays, mild liver dysfunction, and hearing and visual impairment leading to their classification as deaf-blind children. A proportion of NALD-IRD children will develop a leukodystrophy that represents destruction of normal myelin. They may also develop adrenal gland insufficiency and osteopenia, the latter causing pathological fractures. Cells from patients with NALD-IRD contain more functional peroxisomes than ZS patients, and laboratory tests show higher residual peroxisome metabolism. Clinical features result from deficiency of products made by the peroxisome and toxicity of substrates that accumulate (such as very long chain fatty acids).

These autosomal recessive diseases are derived from dysfunction of peroxisomes and current treatment is primarily focused on supportive care, dietary management, symptomatic therapy and treatment strategies involving the use of pharmacological induction of peroxisomes. Administration of bacteria, or an extract or metabolite preparation, as described herein to a subject with a peroxisome deficiency can improve peroxisome activities or function and thereby provide therapeutic benefit.

Engineered Bacteria

In some embodiments, one or more of the compositions or bacterial extracts as described herein comprises an engineered microbe(s). For example, engineered microbes include microbes harboring one or more introduced genetic changes, such change being an insertion, deletion, translocation, or substitution, or any combination thereof, of one or more nucleotides contained on the bacterial chromosome or on an endogenous plasmid, wherein the genetic change can result in the alteration, disruption, removal, or addition of one or more protein coding genes, non-protein-coding genes, gene regulatory regions, or any combination thereof, and wherein such change can be a fusion of two or more separate genomic regions or can be synthetically derived. The engineered microbe(s) can be produced using techniques including but not limited to site-directed mutagenesis, transposon mutagenesis, knock-outs, knock-ins, polymerase chain reaction mutagenesis, chemical mutagenesis, ultraviolet light mutagenesis, transformation (chemically or by electroporation), phage transduction, or any combination thereof.

In one embodiment, the bacterium is from the Acetobacteriaceae family of gram negative bacteria. Members of the Acetobacteriaceae family are generally grouped according to their ability to oxidize sugars or ethanol to produce acetic acid during fermentation. In one embodiment, the bacterium is an *Acetobacter* spp., which is distinguished from other members of the Acetobacteriaceae family, including *Gluconobacter* spp., and *Gluconoacaetobacter* spp.

In another embodiment, the bacterium is a *Gluconobacter* spp. Non-limiting examples of *Gluconobacter* spp. include *Gluconobacter albidus*, *Gluconobacter asaii*, *Gluconobacter cerevisiae*, *Gluconobacter cerinus*, *Gluconobacter frateruii*, *Gluconobacter japonicus*, *Gluconobacter kanchanaburiensis*, *Gluconobacter kondonii*, *Gluconobacter nephelii*, *Gluconobacter oxydans*, *Gluconobacter sphaericus*, *Gluconobacter thailandicus*, *Gluconobacter uchimurae*, and *Gluconobacter wancherniae*.

In another embodiment, the bacterium is a *Gluconacetobacter* spp. Non-limiting examples of *Gluconacetobacter* spp. include *Gluconoacaetobacter aggeris*, *Gluconoacaetobacter asukensis*, *Gluconoacaetobacter azotocaptans*, *Gluconoacaetobacter diazotrophicus*, *Gluconoacaetobacter entanii*, *Gluconoacaetobacter europaeus*, *Gluconoacaetobacter hansenii*, *Gluconoacaetobacter intermedius*, *Gluconoacaetobacter johannae*, *Gluconoacaetobacter kakiaceti*, *Gluconoacaetobacter kombuchae*, *Gluconoacaetobacter liquefaciens*, *Gluconoacaetobacter maltaceti*, *Gluconoacaetobacter medellinensis*, *Gluconoacaetobacter nataicola*, *Gluconoacaetobacter oboediens*, *Gluconoacaetobacter rhaeticus*, *Gluconoacaetobacter sacchari*, *Gluconoacaetobacter saccharivorans*, *Gluconoacaetobacter sucrofermentans*, *Gluconoacaetobacter swingsii*, *Gluconoacaetobacter takamatsuzukensis*, *Gluconoacaetobacter tumulicola*, *Gluconoacaetobacter tumulisoli*, and *Gluconoacaetobacter xylinus*. In another embodiment of this aspect and all other aspects provided herein, the bacterium is *Gluconobacter* EBT 405.

In some embodiments, the bacterium is *Gluconobacter albidus*, *Gluconobacter cerinus*, *Gluconobacter frateruii*, *Gluconobacter japonicus*, *Gluconobacter kondonii*, *Gluconobacter nephelii*, *Gluconobacter oxydans*, *Gluconoacetobacter diazotrophicus*, *Gluconoacetobacter hansenii*, *Gluconoacetobacter saccharivorans*, *Acetobacter aceti* or *Acetobacter malorum*.

In some embodiments, the bacterium is not a member of the Acetobacteriaceae family but is genetically modified to produce similar metabolites (e.g., gluconic acid, 2-keto-gluconic acid, 5-keto-gluconic acid, and/or 2,5-diketo-D-gluconic acid). For example, in some embodiments, a bacterium as described herein is genetically modified to express, e.g., one or more of: membrane-bound PQQ-dependent glucose dehydrogenase (mGDH), ubiquinol-cytochrome c reductase iron-sulfur subunit, TonB-dependent receptor, carbon-nitrogen hydrolase, and ubiquinol oxidase subunit II. Methods of introducing heterologous genetic material to bacterial cells by transformation or transduction are well known, and include, as non-limiting examples, chemical transformation, particle bombardment, and electroporation. The approach best suited to a given bacterium will be known to those of ordinary skill in the art.

The following sequences are provided for selected metabolic pathway enzymes that can be expressed in an engineered bacterium.

```
>mGDH nucleotide sequence
                                                         SEQ ID NO: 1
atgagcacaatttcccggccagggctctgggccctgataacggccgcggtattcgcgctttgcggcgc gatccttaccgttggcggcgcatgggtcgctgccatcggcggccctctttattatgtcatccttggcc tggcacttctcgccacggcttcctctcattccggcgcaatccggctgccctctatctgttcgcagtc gtcgtcttcggaacggtcatctgggaactcaccgttgtcggtctcgacatctgggccctgatcccgcg ctcggacatcgtcatcatcctcggcatctggctgctgctgccgttcgtctcgcgccagatcggtggca cgcggacgaccgtcctgccgctcgccggcgccgttggcgttgcggttctggccctgttcgccagcctc ttcaccgacccgcatgacatcagcggcgaactgccgacgcagatcgcaaacgcctccccgccgaccc ggacaacgttccggccagcgagtggcacgcttatggtcgtacgcaggccggtgaccgctggtcccgc tgaaccagatcaatgcgacgaacgtcagcaacctcaaggtcgcatggcatatccacaccaaggatatg atgaactccaacgacccgggcgaagcgacgaacgaagcgacgccgatcgagttcaacaacacgcttta tatgtgctcactgcatcagaagctgtttgcggttgatggtgccaccggcaacgtcaagtgggtctacg atccgaagctccagatcaaccctggcttccagcatctgacctgccgtggcgtcagcttccacgaaacg ccggccaatgccatggattccgatggcaatcctgctccgacggactgcgccaagcgcatcatcctgcc ggtcaatgatggccgtctggtttgaagtcgatgccgacacgggcaagacctgctccggcttcggcaaca atggcgagatcgacctgcgcgttccgaaccagccttacacgacgcctggccagtacgagccgacgtcc ccgccggtcatcacagacaagctgatcatcgccaacagcgccatcaccgataacggttcggtcaagca
```

-continued

```
ggcttcgggcgccacgcaggcattcgacgtctacaccggcaagcgcgtctgggtgttcgatgcgtcca
acccggatccgaaccagcttccggatgagagccaccctgtcttccacccgaactcgccaaactcctgg
atcgtgtcgtcctacgacgccaacctgaacctcgtgtacatcccgatgggcgtggggactcccgacca
gtggggcggtgaccgcacgaaggattccgagcgtttcgctccgggtatcgttgcgctgaacgccgata
cgggcaagctcgcctggttctaccagaccgttcatcacgatctgtgggacatggacgttccgtcccag
ccgagcctcgtggatgtgacacagaaggacggcacgcttgttccggccatctacgctccgaccaagac
cggcgacattttcgtcctcgaccgtcgtaccggcaaggaaatcgtcccggctccggaaaccccggttc
cccagggtgctgctccgggtgaccacaccagcccgacccagccgatgtcgcagctgaccctgcgtccg
aagaacccgctgaacgactccgatatctggggcggcacgatcttcgaccagatgttctgcagcatcta
tttccacaccctccgctacgaaggcccttcacgccgccgtcgctcaagggctcgctcatcttcccgg
gtgatctgggaatgttcgaatggggtggtctggccgtcgatccgcagcgtcaggtggctttcgccaac
ccgatttccctgccgttcgtctctcagcttgttccccgcggaccgggcaaccccgctctggcctgaagg
aaatgccaagggcacgggtggtgaaaccggcctgcagcacaactatggcatcccgtatgccgtcaacc
tgcatccgttcctggatccggtgctgctgccgttcggcatcaagatgccgtgccgcacgccgcctgg
ggctatgtcgccggtattgacctgaagaccaacaaggtcgtctggcagcaccgcaacggcaccctgcg
tgactcgatgtatggcagctccctgccgatcccgctgccgccgatcaagatcggtgtcccgagcctcg
gtggcccgctctccacggctggcaatctcggcttcctgacggcgtccatggattactacatccgtgcg
tacaacctgacgacgggcaaggtgctgtggcaggaccgtctgccggctggtgctcaggcaacgccgat
cacctatgccatcaacggcaagcagtacatcgtgacctatgcaggcggacacaactcgttcccgaccc
gcatgggcgacgacatcatcgcctacgccctgcccgatcagaaatga
```

```
>mGDH protein sequence
                                                      SEQ ID NO: 2
MSTISRPGLWALITAAVFALCGAILTVGGAWVAAIGGPLYYVIL
GLALLATAFLSFRRNPAALYLFAVVVFGTVIWELTVVGLDIWALIPRSD
IVIILGIWLLLPFVSRQIGGTRTTVLPLAGAVGVAVLALFASLFTDPHD
ISGELPTQIANASPADPDNVPASEWHAYGRTQAGDRWSPLNQINATNVS
NLKVAWHIHTKDMMNSNDPGEATNEATPIEFNNTLYMCSLHQKLFAVDG
ATGNVKWVYDPKLQINPGFQHLTCRGVSFHETPANAMDSDGNPAPTDCA
KRIILPVNDGRLVEVDADTGKTCSGFGNNGEIDLRVPNQPYTTPGQYEP
TSPPVITDKLIIANSAITDNGSVKQASGATQAFDVYTGKRVWVFDASNP
DPNQLPDESHPVFHPNSPNSWIVSSYDANLNLVYIPMGVGTPDQWGGDR
TKDSERFAPGIVALNADTGKLAWFYQTVHHDLWDMDVPSQPSLVDVTQK
DGTLVPAIYAPTKTGDIFVLDRRTGKEIVPAPETPVPQGAAPGDHTSPT
QPMSQLTLRPKNPLNDSDIWGGTIFDQMFCSIYFHTLRYEGPFTPPSLK
GSLIFPGDLGMFEWGGLAVDPQRQVAFANPISLPFVSQLVPRGPGNPLW
PEGNAKGTGGETGLQHNYGIPYAVNLHPFLDPVLLPFGIKMPCRTPPWG
YVAGIDLKTNKVVWQHRNGTLRDSMYGSSLPIPLPPIKIGVPSLGGPLS
TAGNLGFLTASMDYYIRAYNLTTGKVLWQDRLPAGAQATPITYAINGKQ
YIVTYAGGHNSFPTRMGDDIIAYALPDQK
```

```
>ubiquinol-cytochrome c reductase iron-sulfur subunit nucleotide sequence
                                                      SEQ ID NO: 3
atgacccaggacgatgcctctctcatttctgatccaacgtcttccagacaggaggagggtctcgccg
cagggatgtgctggcaacggtaacagttgccatgggatgtgcaggcgcgtgtgctgtggcctatcctt
ttctggacagcctgaatgggacgcgcgccaatcatgtcggggagagcgacatcctggacgtggatctc
tctaccctcaaagccggccagcagattgttgtgacatggcgggggtggcccgtgttcgtgcagagaag
aacgccagaaatgctgaaaacgcttcaggatccggcaatcctgcagaaactacgagatcctgagtcct
gcattttccaacaacccaaagacgcaacaaactggcatcgttccgtcagccccgatatcggcgtcatg
attgggatctgtaccatctcggctgcgtgccgactttcgacgccccgacgcaggcagaacctgccgg
```

```
-continued
gaaatacctctgcccctgtcatggttcacagtttgacagtgcaggccgcgcctacaggaacgcccctg caccatacaatctgccggttccgcccgtgacaatgatttccgatacgcatctgcgaattggagaaagc aaaaacgatcctgactttgatattgctaacatccagcagatctga
```

>ubiquinol-cytochrome c reductase iron-sulfur
subunit protein sequence

SEQ ID NO: 4

```
MTQDDASLISDPTSSRQEEGSRRRDVLATVTVAMGCAGACAVAY
PFLDSLNGTRANHVGESDILDVDLSTLKAGQQIVVTWRGWPVFVQRRTP
EMLKTLQDPAILQKLRDPESCIFQQPKDATNWHRSVSPDIGVMIGICTH
LGCVPTFDAPTQAEPAGKYLCPCHGSQFDSAGRAYRNAPAPYNLPVPPV
TMISDTHLRIGESKNDPDFDIANIQQI
```

>TonB-dependent receptor nucleotide sequence

SEQ ID NO: 5

```
atgatcgtatcgcgtcgcaatacgttactttgcgcatcggtgctggggatgggggcgctttcgagcgt tgctcatgcggcaaccgaaagcactcacacgtcctcacatgtgcgccacaagactgtgactcatggtc cggtgcgttctgctgcgacgcctgcaacaacagctccggtctcggtagctcgtccggtggcagctccg cagttttctgcacctgtagcggtcaaccggtcccatgccgttcgttccattgattccggaacgcagga aagcgttgtggtcacggggtcggctctgagcacgtctaacaatcagaacgcgaacccggtccagatcg tgaccagcaagcagatcgagcagactggcatcaacactctgggtgattacctgcagcgcctgccgtct gtcggttcttcgggtacgacgaacagccaaaccaacaatacggcgggtgtttcttgcacggatatccg taaccttggcaaaagccgtgttctggttctgattgatggcaagcgtgcagcaattgacggctcgtcaa gctgctttgatctgaacaccatcaatattcaccaggtggcgagtgtcgaaatcctcaaggatggtggt tctgagctgtatggtgctgatgccgtttccggtgtcatcaacatcaagctcaaacacaatctggatga cgcgaacctgacggttcgtggaggcatcactgaccgtggagatggccagtccggcatgatttctggct acaagggctggaattttgatcatggccgcggcaacgtgacggtctccggatcttacatgacccagagc gggatccgtcagaacagccgtgactgggccaacccggttgtgtctggtctgattgcaccgggtggttc gccgacttacggatcgtccatcccgacggcgggtcgtttcatcactgatactgcggataatgttccca atggtgatggatcgttccacaatttcagcaagaaagatcgctacaactacggtaatgatcagagcctg acgaactccttgcaggatgccacgctgtcgttcgatgcacattacgacgtgaaccgtcatttcacgcc gtatggcaacttcctgtattcgcatcgtaactctaatacgcagatggcgccgattccggtgtctggta gcatctacccgtccactctgccggtagccatcaccattccaggaagtgcgccgtacaattcgcttggc gaagatgccacgatgtacaagcgtatgggtgaatggggtgatcgcgtcagtcagactgctaccgacac atacacggcaaagattggcgcttcgggtgatatcacccacggttggaaatatgacctgtcctatacct acggatggaaccaggtcatgtcccagacttctggcgttggtaattattccaagctgcttcagagctac ggtctatccgctgaagagccgggcaatcctgacagtgcgctggtttacaacccgtcgatctgcactgc agcggctggctgcacactgtccaacccctttcaacaagctttcgccgcaagcggctgattactcgaact acacgtcgcacgatcactactactatcagctgcgtgatctgaacctgcgtattaacaataaccatgtt gttcacatgccgtggaagaacggtggcgatctaggtatcgcgctgggtatggagcatcgtggtgagca gcttgcctatcatccggatgccctcgttgaatctggccagacgctgacgaactctgcttcctacacgg gtggtggattcaacgtcacggaaggctacctcgaaggtaaagccacgctgctgcacaatgcattcctt gccaaggatctgacgattgacggtcagggccgttactcgtcttacaacacgttcggcagcacgaagaa ctggaaggcgtccatcaactgggcaccggttcaggacatccgcttccgtgcaacgcttggcacgtcct accgtcagcctaacgtctatgagctgtatggcggtcagtctctcggctatgcatcagcaactgaccca tgcgacagcgggcaggtcggcacatatggcagtctgacgccaattgtggcggcaaattgcgccaagca
```

-continued

```
ggggattaacagcagtaatttcgtgtctgcttcctccagtcaggttccgaccctgtttggtggcaatc
ccaagctgaagcctgaaactggccgtacctacacgtttggtacaacggtcacgccgcgttggattcca
ggcctctcggcttccgtggaatactggcattacacgctcaagaacatgatttcgtacctgagcagtca
gtacatcatgaaccagtgctacacgggtgcaaacacgtcatattgcaatgacattacccgcgttggca
gcacgaaccagctaaactccgtgacagctctgtatggcaacatcggcggactgaagacgagcggcatc
gactttgaccttgactaccgtatccgcgttacatctcgcgacgttctgacattgtccaacaactttca
gcaacttgtgagctatcttcagcagaacgagctcggcggaaagtggtacaattatgcaggtcgcatgt
tctaccaaaacggtactggcaaccccgcgttcgtgattatgcgaccgttggctggcagcatggtgca
attggcgtcacatatatgatgagctatatgggtggtatgcgttggaacgactcggaaactgatgtgac
ccgttcagcttcgggccgcatcaagacgcctggcatcttctctcatgatgttacggtgacttatcgtt
ggaaaaagtggaacttcgaagctggtgtgaacaacctgctcgacaagaagcctcccttttgtttctggt
gggacagacaacagcgcggctgcccttatggcaaccttacatgggacgtaacgtcttcctgcaggc
aggcgtgaacttctga
```

>TonB-dependent receptor protein sequence
SEQ ID NO: 6

MIVSRRNTLLCASVLGMGALSSVAHAATESTHTSSHVRHKTVTH
GPVRSAATPATTAPVSVARPVAAPQFSAPVAVNRSHAVRSIDSGTQESV
VVTGSALSTSNNQNANPVQIVTSKQIEQTGINTLGDYLQRLPSVGSSGT
TNSQTNNTAGVSCTDIRNLGKSRVLVLIDGKRAAIDGSSSCFDLNTINI
HQVASVEILKDGGSELYGADAVSGVINIKLKHNLDDANLTVRGGITDRG
DGQSGMISGYKGWNFDHGRGNVTVSGSYMTQSGIRQNSRDWANPVVSGL
IAPGGSPTYGSSIPTAGRFITDTADNVPNGDGSFHNFSKKDRYNYGNDQ
SLTNSLQDATLSFDAHYDVNRHFTPYGNFLYSHRNSNTQMAPIPVSGSI
YPSTLPVAITIPGSAPYNSLGEDATMYKRMGEWGDRVSQTATDTYTAKI
GASGDITHGWKYDLSYTYGWNQVMSQTSGVGNYSKLLQSYGLSAEEPGN

-continued

PDSALVYNPSICTAAAGCTLSNPFNKLSPQAADYSNYTSHDHYYYQLRD
LNLRINNNHVVHMPWKNGGDLGIALGMEHRGEQLAYHPDALVESGQTLT
NSASYTGGGFNVTEGYLEGKATLLHNAFLAKDLTIDGQGRYSSYNTFGS
TKNWKASINWAPVQDIRFRATLGTSYRQPNVYELYGGQSLGYASATDPC
DSGQVGTYGSLTPIVAANCAKQGINSSNFVSASSSQVPTLFGGNPKLKP
ETGRTYTFGTTVTPRWIPGLSASVEYWHYTLKNMISYLSSQYIMNQCYT
GANTSYCNDITRVGSTNQLNSVTALYGNIGGLKTSGIDFDLDYRIRVTS
RDVLTLSNNFQQLVSYLQQNELGGKWYNYAGRMFYQNGTGNPRVRDYAT
VGWQHGAIGVTYMMSYMGGMRWNDSETDVTRSASGRIKTPGIFSHDVTV
TYRWKKWNFEAGVNNLLDKKPPFVSGGTDNSAAALYGNLYMGRNVFLQA
GVNF

>carbon-nitrogen hydrolase nucleotide sequence
SEQ ID NO: 7

```
atgcgcgttgccctgatccagatggctccttcggcggaccggagtgccaatatccttcaagctcagcg
gctggtttcagaagctgtcaaagctcggaagccagatcttgtggtgctgcctgaaatctggagctgtc
tgggtggttcggctgcgaccaagcaggctaatgcagagcttctacctgatccaggcgatgctggaggt
gtactctacgaagcgttgagggccatggcccgggaacataatgtctgggttcacggtggttcaatcgg
agaacttgtagggcctgagtcgggcgacaagcttgccaatacttcactcgttttcaaccctgatggcg
aggaatgtgggcgttacagaaaaatccatctcttcgatgttattacacccaatggggacggctatcgt
gaaagcgataattatgtgcccggggaagcgatcgaagtcgtcgatattgatggcgtcccaaccggcct
cgcgatttgctatgatttgaggtttgctgagctgtttcttgcacttcgggctgcggatgttgagatga
ttgttctgcccgcagcgtttacgcagcaaacgggtgaagctcactgggacattcttgtccgtgctcgc
gctattgagtctcagacgtgggtgatagcgtgtggaacaacgggctggcatgtcgatgggcaaggcaa
```

```
tcagcgccagacctatggccattccatgatcgtcagcccatggggcgaggttgttcttcaattgggta gtgaagaaggctggggggtggctgatcttgatatggatgaggttcgacaggtgcgggagagaatgcct gtgcagataaacaggcggctgatttga
```

\>carbon-nitrogen hydrolase protein sequence

SEQ ID NO: 8

```
MRVALIQMAPSADRSANILQAQRLVSEAVKARKPDLVVLPEIWS

CLGGSAATKQANAELLPDPGDAGGVLYEALRAMAREHNVWVHGGSIGEL

VGPESGDKLANTSLVFNPDGEECGRYRKIHLFDVITPNGDGYRESDNYV

PGEAIEVVDIDGVPTGLAICYDLRFAELFLALRAADVEMIVLPAAFTQQ

TGEAHWDILVRARAIESQTWVIACGTTGWHVDGQGNQRQTYGHSMIVSP

WGEVVLQLGSEEGWGVADLDMDEVRQVRERMPVQINRRLI
```

\>ubiquinol oxidase subunit II nucleotide sequence

SEQ ID NO: 9

```
atgatgaaagcaggaccgatgaaaaaactctggcgatatctcccagcgttgccggcgctgatgctatc gggttgcacggttgatctgcttcagccgcgcggtccgatcgcagaaatgaaccgcgacgttatggtgg cagaatttgccatcatgatggcgattgtggttccgacctgtatcgcaacgctttattttgcttggaag tatcgcgcttccaatacccaggccgaatatctgccgacctgggatcactcaacgaagattgagtatgt catctggggcgtccctgctctgatcattattgcccttggcgcgatcagctggtacagcacccatgctt atgacccgtaccgcccgctccagacggctgacaacgtcaagccgctgaacgttcaggtggtctctctc gactggaaatggctgttcatctatccggatctggggatcgccacgatcaaccagctggatgtgcccac gaacacgccgctgaacttccagatcacctctgacactgtcatgacgtcgttcttcatcccgcgtctgg gatcaatgatctactccatgccgggtcagcagacacagctgcatcttcttgcaactgagtcgggtgac tatctgggtgaagcttcccagttcagtggtcgcggtttctctgacatgaagttccgcacccctcgccat ggcacctgaagaattcagcgcctgggtcgagaaggtgaagagcggcagcgaaaacctcgatgacacga cttatccgaagtacgccgccccgcaggaagctgcgccggttcagtatttcgcgcatgtccagccggat ctcttcgacggcatcgtcgccaagtacaacaatggcatgatggttgagaagacgacgggcaaggtcat gcatatgcagtccgcttccagcgctgcaccgtccgacactggcatgaaggaataa
```

\>ubiquinol oxidase subunit II protein sequence

SEQ ID NO: 10

```
MMKAGPMKKLWRYLPALPALMLSGCTVDLLQPRGPIAEMNRDVM

VAEFAIMMAIVVPTCIATLYFAWKYRASNTQAEYLPTWDHSTKIEYVIWGVPALIIIA

LGAISWYSTHAYDPYRPLQTADNVKPLNVQVVSLDWKWLFIYPDLGIATINQLDVPTN

TPLNFQITSDTVMTSFFIPRLGSMIYSMPGQQTQLHLLATESGDYLGEASQFSGRGFS

DMKFRTLAMAPEEFSAWVEKVKSGSENLDDTTYPKYAAPQEAAPVQYFAHVQPDLFDG

IVAKYNNGMMVEKTTGKVMHMQSASSAAPSDTGMKE
```

In order to facilitate transfer of genetic material (e.g., a plasmid, DNA etc.) to a bacterium, artificial cell competence can be induced by exposing the bacterium to particular conditions. For example, one method of inducing cell competence is by incubating the bacterium in a solution with divalent cations (e.g., calcium chloride) to partially disrupt the membrane and then heat-shocking the host cells to induce them to take up e.g., plasmid DNA. An alternative method for inducing cell competence is electroporation, where the cells are exposed to an electric field, which can generate small holes in the cell membrane such that plasmid DNA can enter the cell.

The plasmid-supplied nucleic acid (e.g., DNA) can be stably integrated into the genome or can be maintained episomally, e.g., on a plasmid or other episomal vector. In some embodiments, a sequence directing the expression of the one or more enzymes described herein can be placed under the control of naturally-occurring regulatory elements in the cell. In other embodiments, constructs for the expression of at least one of: membrane-bound PQQ-dependent glucose dehydrogenase (mGDH), ubiquinol-cytochrome c reductase iron-sulfur subunit, TonB-dependent receptor, carbon-nitrogen hydrolase, and ubiquinol oxidase subunit II will generally include regulatory elements, including, promoters, enhancers, etc. that direct the expression of the encoded sequences. A gene under the control of a set of regulatory elements is generally referred to as "operably linked" to those elements. Typically, an expression vector comprises a transcription promoter, a transgene encoding sequence, and a transcription terminator.

An expression vector, or a vector, as described herein, is a nucleic acid molecule encoding a gene that is expressed when the molecule is introduced to a host-cell. Typically, an expression vector comprises a transcription promoter, a gene encoding sequence, and a transcription terminator. Gene expression in an expression vector is usually placed under the control of a promoter, and such a gene is said to be "operably linked to" the promoter. Similarly, a regulatory element and a core promoter are operably linked if the regulatory element modulates the activity of the core promoter.

In some embodiments it may be useful to include in the transformed cells a positive marker that permits the selection of cells positive for the plasmid-supplied nucleic acid sequence(s) in vitro. The positive selectable marker may be a gene that upon being introduced into the host cell expresses a dominant phenotype permitting positive selection of cells carrying the gene. Genes of this type are known in the art, and include, for example, an antibiotic resistance gene (e.g., resistance to blasticidin, mycophenolic acid, puromycin, zeocin, actinomycin, ampicillin, kanamycin, neomycin, polymixin B sulfate, or streptomycin), or an enzyme that converts a substrate to a colored product (e.g., blue/white screening by expression of B-galactosidase, which converts X-gal into galactose and an insoluble blue pigment) etc. Other selection tools can include e.g., radioactive nucleic acid probes, and labeled antibodies that are specific to the protein expressed by the transgene.

Prebiotics

A prebiotic is an ingredient or compositions that is not digestible by a bacterial host, e.g., a h human, but that is fermentable by, and selectively promotes the growth and/or activity of beneficial bacteria in the host. Such selective fermentation that allows specific changes, both in the composition and/or activity of the gastrointestinal microbiota, that confers neutral or positive benefits upon host well-being and health. Prebiotics can include complex carbohydrates, amino acids, peptides, or other nutritional components useful for the survival, colonization and persistence of the bacterial composition.

Suitable prebiotics are usually plant-derived complex carbohydrates, oligosaccharides or polysaccharides. Generally, prebiotics are indigestible or poorly digested by humans and serve as a food source for bacteria. Prebiotics, which can be used in the pharmaceutical dosage forms, and pharmaceutical compositions and methods provided herein include, without limitation, galactooligosaccharides (GOS), trans-galactooligosaccharides, fructooligosaccharides, or oligofructose (FOS), inulin, oligofructose-enriched inulin, lactulose, arabinoxylan, xylooligosaccharides (XOS), mannooligosaccharides, gum guar, gum Arabic, tagatose, amylose, amylopectic, xylan, pectin, combinations thereof, and the like.

In some embodiments, the prebiotic comprises a mixture of one or more non-digestible oligosaccharides, non-digestible polysaccharides, free monosaccharides, non-digestible saccharides, starch, or non-starch polysaccharides. Suitable oligosaccharides and their production methods are further described in Laere K J M, "Degradation of structurally different non-digestible oligosaccharides by intestinal bacteria: glycosylhydrolases of *Bi. Adolescentis* (2000) PhD thesis, Wageningen Agricultural University, Wageneingen, The Netherlands.

Culture and Storage of Bacteria

For banking, the strain(s) included in the bacterial composition can be (1) isolated directly from a specimen or taken from a banked stock, (2) optionally cultured on a nutrient agar or broth that supports growth to generate viable biomass, and (3) the biomass optionally preserved in multiple aliquots in long-term storage.

In embodiments using a culturing step, the agar or broth contains nutrients that provide essential elements and specific factors that enable growth. An example would be a medium composed of 20 g/L glucose, 10 g/L yeast extract, 10 g/L soy peptone, 2 g/L citric acid, 1.5 g/L sodium phosphate monobasic, 100 mg/L ferric ammonium citrate, 80 mg/L magnesium sulfate, 10 mg/L hemin chloride, 2 mg/L calcium chloride, and 1 mg/L menadione. A variety of microbiological media and variations are well known in the art (e.g. R. M. Atlas, *Handbook of Microbiological Media* (2010) CRC Press). Medium can be added to the culture at the start, can be added during the culture, or can be intermittently/continuously flowed through the culture. The strains in the bacterial composition can be cultivated alone, as a subset population of a bacterial composition, or as an entire population of different species or strains comprising a bacterial composition. As an example, a first strain can be cultivated together with a second strain in a mixed continuous culture, at a dilution rate lower than the maximum growth rate of either cell to prevent the culture from washing out of the cultivation.

The inoculated culture is incubated under favorable conditions for a time sufficient to build biomass. For bacterial compositions for human use this is often at normal body temperature (37° C.), pH, and other parameter with values similar to the normal human niche. The environment can be actively controlled, passively controlled (e.g., via buffers), or allowed to drift. For example, for anaerobic bacterial compositions (e.g., gut microbiota), an anoxic/reducing environment can be employed. This can be accomplished by addition of reducing agents/factors such as cysteine to the broth, and/or stripping it of oxygen. As an example, a culture of a bacterial composition can be grown at 37° C., pH 7, in the medium above, pre-reduced with 1 g/L cysteine.HCl.

When the culture has generated sufficient biomass, it can be preserved for banking or storage. The organisms can be placed into a chemical milieu that protects from freezing (adding 'cryoprotectants'), drying ('lyoprotectants'), and/or osmotic shock ('osmoprotectants'), dispensing into multiple (optionally identical) containers to create a uniform bank, and then treating the culture for preservation. Containers are generally impermeable and have closures that assure isolation from the environment. Cryopreservation treatment is accomplished by freezing a liquid at ultra-low temperatures (e.g., at or below −80° C.). Dried preservation removes water from the culture by evaporation (in the case of spray drying or 'cool drying') or by sublimation (e.g., for freeze drying, spray freeze drying). Removal of water improves long-term bacterial composition storage stability at temperatures elevated above cryogenic. If the bacterial composition comprises spore forming species and results in the production of spores, the final composition can be purified by additional means such as density gradient centrifugation and preserved using the techniques described above. Bacterial composition banking can be done by culturing and preserving the strains individually, or by mixing the strains together to create a combined bank. As an example of cryopreservation, a bacterial composition culture can be harvested by centrifugation to pellet the cells from the culture medium, the supernatant decanted and replaced with fresh culture broth containing 15% glycerol. The culture can then be aliquoted into 1 mL cryotubes, sealed, and placed at −80° C. for long-term viability retention. This procedure achieves acceptable viability upon recovery from frozen storage.

Organism production can be conducted using similar culture steps to banking, including medium composition and culture conditions. It can be conducted at larger scales of operation, especially for clinical development or commercial production. At larger scales, there can be several sub-cultivations of the bacterial composition prior to the final cultivation. At the end of cultivation, the culture is harvested to enable further formulation into a dosage form for administration. This can involve concentration, removal of undesirable medium components, and/or introduction into a chemical milieu that preserves the bacterial composition and renders it acceptable for administration via the chosen route. For example, a bacterial composition can be cultivated to a concentration of $10^{10}$ CFU/mL, then concentrated 20-fold by tangential flow microfiltration; the spent medium may be exchanged by diafiltering with a preservative medium consisting of 2% gelatin, 100 mM trehalose, and 10 mM sodium phosphate buffer. The suspension can then be freeze-dried to a powder and titrated.

After drying, the powder can be blended to an appropriate potency, and mixed with other cultures and/or a filler such as microcrystalline cellulose for consistency and ease of handling, and the bacterial composition formulated as provided herein.

In one embodiment, one or more of the populations of bacterial cells in the composition are co-cultured.

In some embodiments, the bacteria are not grown in a medium consisting of 0-5% yeast extract broth. In other embodiments, the bacteria are grown in 0-5% yeast extract broth with glucose or another metabolizable monosaccharide (e.g., fructose) or disaccharide (e.g., sucrose) in order to optimize production of the metabolites as described herein. In some embodiments, the concentration of glucose or metabolizable monosaccharide or disaccharide is 0.5-5%. In one embodiment, the medium comprises 3% yeast extract broth.

In some embodiments, corn steep liquor is added to the bacterial medium to optimize metabolite production (e.g., 0.5-5% corn steep liquor). Corn steep liquor is a byproduct of wet corn milling. Its components are soluble proteins, amino acids, carbohydrates, organic acids (e.g., lactic acid), vitamins, and minerals. It is sometimes combined with other ingredients in corn gluten feed and widely used in complete feeds for dairy and beef cattle, poultry, swine, and pet foods. Some corn steep liquor is used in the production of acetic acid, food acids, and fermentation processes. Some corn steep liquor is used in the pharmaceutical industry in the production of intravenous solutions and drugs, most notably antibiotics (penicillin). In certain embodiments, the concentration of corn steep liquor is 0.5-4%, 0.5-3%, 0.5-2%, 0.5-1%, 2-4%, 3%, 2-5%, 3-5%, 4-5%, 1-4%, or any range therebetween. In one embodiment the concentration of corn steep liquor is 3%.

Dosage, Administration and Formulations

In some embodiments, cells over a range of, for example, $2-5\times10^5$, or more, e.g., $1\times10^6$, $1\times10^7$, $1\times10^8$, $5\times10^8$, $1\times10^9$, $5\times10^9$, $1\times10^{10}$, $5\times10^{10}$, $1\times10^{11}$ or more can be administered in a composition comprising a bacterium or collection of bacteria as described herein. The dosage range for the bacteria depends upon the potency, and includes amounts large enough to produce the desired effect, e.g., reduction in at least one symptom of a disease associated with mitochondrial dysfunction in a treated subject. The dosage should not be so large as to cause unacceptable adverse side effects. Generally, the dosage will vary with the type of illness, and with the age, condition, and sex of the patient. The dosage can be determined by one of skill in the art and can also be adjusted by the individual physician in the event of any complication.

For use in the various aspects described herein, an effective amount of cells in a composition as described herein comprises at least $1\times10^5$ bacterial cells, at least $1\times10^6$ bacterial cells, at least $1\times10^7$ bacterial cells, at least $1\times10^8$ bacterial cells, at least $1\times10^9$ bacterial cells, at least $1\times10^{10}$ bacterial cells, at least $1\times10^{11}$ bacterial cells, at least $1\times10^{12}$ bacterial cells or more. In some embodiments of the aspects described herein, the bacterial cells (e.g., isolated from rotting fruit) are expanded or maintained in culture prior to administration to a subject in need thereof. In one embodiment, the bacterial strain(s) is/are obtained from a microbe bank. In some embodiments, two or more bacterial strains are administered together, e.g., in a single admixture. However, it is specifically contemplated herein that two or more bacterial strains can be administered as separate dosage forms or sub-mixtures or sub-combinations of the strains. Thus, for a consortium of e.g., three members, the consortium can be administered, for example, as a single preparation including all three members (in one or more dosage units, e.g., one or more capsules) or as two or more separate preparations that, in sum, include all members of the given strains. While administration as a single admixture is preferred, a potential advantage of the use of e.g., individual units for each strain, is that the actual strains administered to any given subject can be tailored, if necessary, by selecting the appropriate combination of, for example, single species dosage units that together comprise the desired consortium.

In some embodiments, the compositions described herein can be administered in a form containing one or more pharmaceutically acceptable carriers. Suitable carriers are well known in the art and vary with the desired form and mode of administration of the composition. For example, pharmaceutically acceptable carriers can include diluents or excipients such as fillers, binders, wetting agents, disintegrators, surface-active agents, glidants, lubricants, and the like. Typically, the carrier may be a solid (including powder), liquid, or combinations thereof. Each carrier is preferably "acceptable" in the sense of being compatible with the other ingredients in the composition and not injurious to the subject. The carrier can be biologically acceptable and inert (e.g., it permits the composition to maintain viability of the biological material until delivered to the appropriate site).

Oral compositions can include an inert diluent or an edible carrier. For the purpose of oral therapeutic administration, the active compound can be incorporated with excipients and used in the form of tablets, lozenges, pastilles, troches, or capsules, e.g., gelatin capsules. Oral compositions can also be prepared by combining a composition of the present disclosure with a food. In some embodiments, the bacterium/bacteria can be formulated in a food item. Some non-limiting examples of food items to be used with the methods and compositions described herein include: popsicles, cheeses, creams, chocolates, milk, meat, drinks, pickled vegetables, kefir, miso, sauerkraut, etc. In other embodiments, the food items can be juices, refreshing beverages, tea beverages, drink preparations, jelly beverages, and functional beverages; alcoholic beverages such as beers; carbohydrate-containing foods such as rice food products, noodles, breads, and pastas; paste products such as fish, hams, sausages, paste products of seafood; retort pouch products such as curries, food dressed with a thick starchy sauce, and Chinese soups; soups; dairy products such as milk, dairy beverages, ice creams, and yogurts; fermented products such as fermented soybean pastes, fermented beverages, and pickles; bean products; various confectionery products including biscuits, cookies, and the like, candies, chewing gums, gummies, cold desserts including jellies, cream caramels, and frozen desserts; instant foods such as instant soups and instant soy-bean soups; and the like. It is preferred that food preparations not require cooking after admixture with the bacterial strain(s) to avoid killing the microbes.

In one embodiment a food used for administration is chilled, for instance, iced flavored water. In certain embodiments, the food item is not a potentially allergenic food item (e.g., not soy, wheat, peanut, tree nuts, dairy, eggs, shellfish or fish). Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, primogel, or corn starch; a lubricant such as magnesium stearate or sterotes; a glidant such as colloidal silicon dioxide; a sweetening agent such as sucrose or saccharin; or a flavoring agent such as peppermint, methyl salicylate, orange flavoring, or other suitable flavorings. These are for purposes of example only and are not intended to be limiting.

Formulations suitable for oral administration may be provided as discrete units, such as tablets, capsules, cachets, syrups, elixirs, prepared food items, microemulsions, solutions, suspensions, lozenges, or gel-coated ampules, each containing a predetermined amount of the active compound; as powders or granules; as solutions or suspensions in aqueous or non-aqueous liquids; or as oil-in-water or water-in-oil emulsions.

The compositions described herein can also be prepared in the form of suppositories (e.g., with conventional suppository bases such as cocoa butter and other glycerides) or retention enemas for rectal delivery. Formulations suitable for rectal administration include gels, creams, lotions, aqueous or oily suspensions, dispersible powders or granules, emulsions, dissolvable solid materials, douches, and the like. The formulations are preferably provided as unit-dose suppositories comprising the active ingredient in one or more solid carriers forming the suppository base, for example, cocoa butter. Suitable carriers for such formulations include petroleum jelly, lanolin, polyethyleneglycols, alcohols, and combinations thereof. Alternatively, colonic washes with the rapid recolonization deployment agent of the present disclosure can be formulated for colonic or rectal administration. The compositions can be prepared with carriers that will protect the bacteria against rapid elimination from the body, such as a controlled release formulation, including implants. Biodegradable, biocompatible polymers can be used, such as ethylene vinyl acetate, polyanhydrides, polyglycolic acid, collagen, polyorthoesters, and polylactic acid. Such formulations can be prepared using standard techniques. The materials can also be obtained commercially from, for instance, Alza Corporation and Nova Pharmaceuticals, Inc. Liposomal suspensions can also be used as pharmaceutically acceptable carriers. These can be prepared according to methods known to those skilled in the art.

In some embodiments, a composition can be encapsulated or microencapsulated (e.g., enteric-coated formulations). For instance, when the composition is to be administered orally, the dosage form is formulated so the composition is not exposed to conditions prevalent in the gastrointestinal tract before the small intestine, e.g., high acidity and digestive enzymes present in the stomach. An enteric coating can be stable at low pH (such as in the stomach) and can dissolve at higher pH (for example, in the small intestine). Material that can be used in enteric coatings includes, for example, alginic acid, cellulose acetate phthalate, plastics, waxes, shellac, and fatty acids (e.g., stearic acid, palmitic acid). Enteric coatings are described, for example, in U.S. Pat. Nos. 5,225,202, 5,733,575, 6,139,875, 6,420,473, 6,455,052, and 6,569,457, all of which are herein incorporated by reference in their entirety. The enteric coating can be an aqueous enteric coating. Examples of polymers that can be used in enteric coatings include, for example, shellac (trade name EmCoat 120 N, Marcoat 125); cellulose acetate phthalate (trade names AQUACOAT, AQUACOAT ECD, SEPIFILM™, KLUCEL™, and ETOLOSE™); polyvinylacetate phthalate (trade name SURETERIC™); and methacrylic acid (trade name EUDRAGIT™). The encapsulation of compositions for therapeutic use is known in the art. Encapsulation can include hard-shelled capsules, which can be used for dry, powdered ingredients, or soft-shelled capsules. Capsules can be made from aqueous solutions of gelling agents such as animal protein (e.g., gelatin), plant polysaccharides or derivatives like carrageenans and modified forms of starch and cellulose. Other ingredients can be added to a gelling agent solution such as plasticizers (e.g., glycerin and or sorbitol), coloring agents, preservatives, disintegrants, lubricants and surface treatment.

In one embodiment, an enteric coated probiotic composition as described herein is administered to a subject. In another embodiment, an enteric coated probiotic and prebiotic composition is administered to a subject.

Formulations of a bacterial composition or bacterial extract can be prepared by any suitable method, typically by uniformly and intimately admixing the bacterial cells with liquids or finely divided solid carriers or both, in the required proportions and then, if necessary, shaping the resulting mixture into the desired shape. In some embodiments, the bacterial strain(s) as described herein is/are combined with one or more additional probiotic organisms prior to treatment of a subject. As used herein, the term "probiotic" refers to microorganisms that form at least a part of the transient or endogenous flora and thereby exhibit a beneficial prophylactic and/or therapeutic effect on the host organism. Probiotics are non-pathogenic under normal circumstances and include, but are not limited to, those designated "Generally Regarded as Safe (GRAS)" by the U.S. Food & Drug Administration.

A nutrient supplement comprising the bacterium or bacterial consortium as described herein can include any of a variety of nutritional agents, including vitamins, minerals, essential and nonessential amino acids, carbohydrates, lipids, foodstuffs, dietary supplements, short chain fatty acids and the like. Preferred compositions comprise vitamins and/or minerals in any combination. Vitamins for use in a composition as described herein can include vitamins B, C, D, E, folic acid, K, niacin, and like vitamins. The composition can contain any or a variety of vitamins as may be deemed useful for a particular application, and therefore, the vitamin content is not to be construed as limiting. Typical vitamins are those, for example, recommended for daily consumption and in the recommended daily amount (RDA), although precise amounts can vary. The composition can preferably include a complex of the RDA vitamins, minerals and trace minerals as well as those nutrients that have no established RDA, but have a beneficial role in healthy human or mammal physiology. The preferred mineral format can include, for example, those that are in either the gluconate or citrate form which are more readily metabolized by lactic acid bacteria. Similar considerations can be employed to favor other classes of bacteria as needed. In a related embodiment, the compositions described herein are contemplated to comprise one or more bacteria or a bacterial consortium as described herein in combination with a viable lactic acid bacteria in combination with any material to be absorbed, including but not limited to nutrient supplements, foodstuffs, vitamins, minerals, medicines, therapeutic compositions, antibiotics, hormones, steroids, and the like compounds where it is desirable to insure efficient and healthy absorption of materials from the gastrointestinal tract into the blood. The amount of material included in the composition can vary widely depending upon the material and the intended purpose for its absorption, such that the composition is not to be considered as limiting.

The compositions as described herein can comprise from about 100 mg to about 100 g, alternatively from about 500 mg to about 50 g, and alternatively from about 1 g to about 40 g, of a prebiotic, per day or on a less than daily schedule.

Prior to administration of a bacterial composition, the patient may optionally have a pretreatment protocol with an antibiotic to prepare the gastrointestinal tract to receive the bacterial composition. In certain embodiments, the pretreatment protocol is advisable, such as when a patient has an acute infection with a highly resilient pathogen. In other embodiments, the pretreatment protocol is entirely optional, such as when a patient does not have an infection with a pathogen, or for example, when a pathogen causing an infection is not resilient, or the patient has had an acute infection that has been successfully treated but where the physician is concerned that the infection may recur. In these instances, the pretreatment protocol can enhance the ability of the bacterial composition to affect the patient's microbiome and/or enhance the therapeutic outcome. In an alternative embodiment, the subject is not pre-treated with an antibiotic.

As one way of preparing the patient for administration of the therapeutic microbes, at least one antibiotic can be administered to alter the bacteria in the patient. As another way of preparing the patient for administration, a standard colon-cleansing preparation can be administered to the patient to substantially empty the contents of the colon, such as used to prepare a patient for a colonoscopy. By "substantially emptying the contents of the colon," is meant removing at least 75%, at least 80%, at least 90%, at least 95%, or about 100% of the ordinary volume of colon contents. Antibiotic treatment can precede a colon-cleansing protocol.

If a patient has received an antibiotic for treatment of an infection, or if a patient has received an antibiotic as part of a specific pretreatment protocol, in one embodiment the antibiotic should be stopped in sufficient time to allow the antibiotic to be substantially reduced in concentration in the gut before a bacterial composition is administered. In one embodiment, the antibiotic may be discontinued 1, 2, or 3 days before the administration of the bacterial composition. In one embodiment, the antibiotic can be discontinued 3, 4, 5, 6, or 7 antibiotic half-lives before administration of the bacterial composition. If the pretreatment protocol is part of treatment of an acute infection, the antibiotic may be chosen so that the infection is sensitive to the antibiotic, but the constituents in the administered bacterial composition are not sensitive to the antibiotic.

Any of the preparations described herein can be administered once on a single occasion or on multiple occasions, such as once a day for several days or more than once a day on the day of administration (including twice daily, three times daily, or up to five times daily). Or the preparation can be administered intermittently according to a set schedule, e.g., once weekly, once monthly, or when the patient relapses from the primary illness. In another embodiment, the preparation can be administered on a long-term basis to assure the maintenance of a protective or therapeutic effect. Note that while description above and elsewhere herein refer to formulations for delivery of bacteria, formulations comprising metabolites produced by such bacteria can be prepared and administered in a similar manner.

Excluded Bacteria: As will be readily appreciated by one of skill in the art, a composition as described herein for treatment of disease will ideally not comprise one or more pathogenic bacteria. In one embodiment, a composition as described herein (e.g., a bacterial extract or a probiotic composition) does not include an organism conventionally classified as a pathogenic or opportunistic organism. It is possible that a function shared by all members of a given taxonomic group could be beneficial, e.g., for providing particular metabolites, yet for other reasons the overall effect of one or more particular members of the group is not beneficial and is, for example, pathogenic. Clearly, members of a given taxonomic group that cause pathogenesis, e.g., acute gastrointestinal pathologies, are to be excluded from the therapeutic or preventive methods and compositions described herein.

In one embodiment, the bacterial composition does not comprise at least one of *Acidaminococcus intestinalis, Lactobacillus casei, Lactobacillus paracasei, Raoultella* sp., and *Streptococcus mitis*. In another embodiment, the bacterial composition does not comprise any of these.

In another embodiment, the bacterial composition does not comprise at least one of *Barnesiella intestinihominis, Lactobacillus reuteri, Enterococcus hirae, Enterococus faecium,* or *Enterococcus durans, Anaerostipes caccae, Clostridium indolis, Staphylococcus wameri,* or *Staphylo-*

*coccus pasteuri*, and *Adlercreutzia equolifaciens*. In another embodiment, the bacterial composition does not comprise any of these.

In another embodiment, the bacterial composition does not comprise at least one of *Clostridium botulinum*, *Clostridium cadaveric*, *Clostridium chauvoei*, *Clostridium clostridioforme*, *Clostridium cochlearium*, *Clostridium difficile*, *Clostridium haemolyticum*, *Clostridium hastiforme*, *Clostridium histolyticum*, *Clostridium indolis*, *Clostridium irregulare*, *Clostridium limosum*, *Clostridium malenominatum*, *Clostridium novyi*, *Clostridium oroticum*, *Clostridium paraputrificum*, *Clostridium perfringens*, *Clostridium piliforme*, *Clostridium putrefaciens*, *Clostridium putrificum*, *Clostridium septicum*, *Clostridium sordellii*, *Clostridium sphenoides*, and *Clostridium tetani*. In another embodiment, the bacterial composition does not comprise any of these.

In another embodiment, the bacterial composition does not comprise at least one of *Escherichia coli* and *Lactobacillus johnsonii*. In another embodiment, the bacterial composition does not comprise any of these.

In another embodiment, the bacterial composition does not comprise at least one of *Clostridium innocuum*, *Clostridium butyricum*, and *Blautia producta* (previously known as *Peptostreptococcus productus*). In another embodiment, the bacterial composition does not comprise any of these.

In another embodiment, the bacterial composition does not comprise at least one of *Eubacteria, Fusobacteria, Propionibacteria, Escherichia coli*, and *Gemmiger*.

In another embodiment, the compositions described herein do not comprise pathogenic bacteria in the Genera *Yersinia, Vibrio, Treponema, Streptococcus, Staphylococcus, Shigella, Salmonella, Rickettsia, Orientia, Pseudomonas, Neisseria, Mycoplasma, Mycobacterium, Listeria, Leptospira, Legionella, Klebsiella, Helicobacter, Haemophilus, Francisella, Escherichia, Ehrlichia, Enterococcus, Coxiella, Corynebacterium, Chlamydia, Chlamydophila, Campylobacter, Burkholderia, Brucella, Borrelia, Bordetella, Bacillus*, multi-drug resistant bacteria, extended spectrum beta-lactam resistant Enterococci (ESBL), Carbapenem-resistant Enterobacteriaceae (CRE), or vancomycin-resistant Enterococci (VRE).

In other embodiments, the compositions described herein do not comprise pathogenic species or strains, such as *Aeromonas hydrophila, Campylobacter fetus, Plesiomonas shigelloides, Bacillus cereus, Campylobacter jejuni*, enteroaggregative *Escherichia coli*, enterohemorrhagic *Escherichia coli*, enteroinvasive *Escherichia coli*, enterotoxigenic *Escherichia coli* (such as, but not limited to, LT and/or ST), *Escherichia coli* 0157:H7, *Helicobacter pylori, Klebsiellia pneumonia, Lysteria monocytogenes, Plesiomonas shigelloides, Salmonella* spp., *Salmonella typhi, Salmonella paratyphi, Shigella* spp., *Staphylococcus* spp., *Staphylococcus aureus*, vancomycin-resistant *enterococcus* spp., *Vibrio* spp., *Vibrio cholerae, Vibrio parahaemolyticus, Vibrio vulnificus*, or *Yersinia enterocolitica*.

In one embodiment, the bacterial compositions or formulations as described herein do not comprise *Klebsiella pneumoniae, Proteus mirabilis, Enterobacter cloacae*, or *Bilophila wadsworthia*.

Efficacy Measurement

The term "effective amount" as used herein refers to the amount of a population of bacterial cells or their components or metabolites needed to alleviate at least one or more symptoms of a disease associated with mitochondrial dysfunction and relates to a sufficient amount of a composition to provide the desired effect. An effective amount as used herein also includes an amount sufficient to prevent or delay the development of a symptom of the disease, alter the course of a symptom of the disease (for example but not limited to, slow the progression of a symptom of the disease, such as myopathy), or reverse a symptom of the disease. It is understood that for any given case, an appropriate "effective amount" can be determined by one of ordinary skill in the art using routine experimentation. Given the intricacies of the body and the nature of cell establishment, the "effective amount" of cells may vary among different patients, however one can easily determine in hindsight if the amount of cells administered was indeed an 'effective amount." Thus, further treatments can be modified accordingly. Note that long-term colonization or establishment, while often desirable, is not necessary for effective treatment as regular administration can achieve effective treatment as well.

The efficacy of treatment can be determined by the skilled clinician. However, a treatment is considered "effective treatment," as the term is used herein, if any one or all of the symptoms, or other clinically accepted symptoms or markers of a disease associated with mitochondrial dysfunction are reduced, e.g., by at least 10% following treatment with a composition comprising bacterial cells or a bacterial extract as described herein. Methods of measuring these indicators are known to those of skill in the art and/or described herein.

In one embodiment, effective treatment is determined by a reduction in the dose of a conventional pharmacological treatment required to maintain adequate control of symptoms of a disease associated with mitochondrial dysfunction.

In some embodiments, the subject is further evaluated using one or more additional diagnostic procedures, for example, by medical imaging, physical exam, laboratory test(s), clinical history, family history, genetic test, and the like. Medical imaging is well known in the art. As such, the medical imaging can be selected from any known method of imaging, including, but not limited to, ultrasound, computed tomography scan, positron emission tomography, photon emission computerized tomography, and magnetic resonance imaging.

The present invention may be as described in any one of the following numbered paragraphs:

1. A composition comprising a measured amount of one or more bacterium that comprises and expresses one or more nucleic acid sequences encoding one or more of membrane-bound PQQ-dependent glucose dehydrogenase (mGDH), ubiquinol-cytochrome c reductase iron-sulfur subunit, TonB-dependent receptor, carbon-nitrogen hydrolase, and ubiquinol oxidase subunit II.

2. The composition of paragraph 1, wherein the bacterium is from the Acetobacteriaceae family.

3. The composition of paragraph 1 or 2, wherein the bacterium is *Gluconobacter* spp (e.g., *Gluconobacter* EBT 405), *Acetobacter* spp., *Gluconoacaetobacter* spp., *Acidomonas* spp, *Ameyamaea* spp., *Asaia* spp., *Granuhbacter* spp., *Kozakia* spp., *Neoasaia* spp., *Neokomagataea* spp., *Saccharibacter* spp., *Swaminathania* spp., or *Tantichaeroenia* spp.

4. The composition of any one of paragraphs 1-3, wherein one or more of the nucleic acid sequences are exogenous nucleic acid sequences.

5. The composition of any one of paragraphs 1-4, wherein the bacterium comprises and expresses nucleic acid sequences encoding each of membrane-bound PQQ-dependent glucose dehydrogenase (mGDH), ubiquinol-cytochrome c reductase iron-sulfur subunit, TonB-dependent receptor, carbon-nitrogen hydrolase, and ubiquinol oxidase subunit II.

6. The composition of any one of paragraphs 1-5, wherein the measured amount of the one or more bacterium is lyophilized.

7. The composition of any one of paragraphs 1-6, wherein the measured amount is an amount effective to induce expression and/or activity of mitochondrial transcription factor A (TFAM), or peroxisome proliferator activated receptor gamma coactivator 1 (PGC) in a human cell upon administration to a subject in need thereof.

8. The composition of paragraph 7, wherein the amount effective to induce expression and/or activity of TFAM, or PGC in a human cell is $1 \times 10^6$ bacteria.

9. The composition of any one of paragraphs 1-8, wherein the composition further comprises one or more added bacterial metabolites selected from the group consisting of gluconic acid, 2-keto-gluconic acid, 5-keto-gluconic acid, and 2,5-diketo-D-gluconic acid.

10. The composition of any one of paragraphs 1-9, wherein the bacterium is viable, attenuated or heat-inactivated.

11. The composition of any one of paragraphs 1-10, wherein the composition is formulated as a food, a beverage, a feed composition, a probiotic, a nutritional supplement, or a pharmaceutical composition.

12. The composition of any one of paragraphs 1-11, which further comprises a prebiotic.

13. The composition of paragraph 12, wherein the prebiotic comprises a fructooligosaccharide, an inulin, an isomaltooligosaccharide, lactilol, lactosucrose, lactulose, a soy oligosaccharide, a transgalactooligosaccharide or a xylooligosaccharide.

14. The composition of any one of paragraphs 1-13, further comprising a pharmaceutically acceptable carrier.

15. The composition of any one of paragraphs 1-14, wherein the composition is formulated for oral administration.

16. The composition of paragraph 15, wherein the composition is an enteric-coated formulation.

17. A composition comprising a therapeutically effective amount of an extract or fraction derived from at least one bacterium that comprises and expresses one or more nucleic acid sequences encoding an enzyme selected from the group consisting of membrane-bound PQQ-dependent glucose dehydrogenase (mGDH), ubiquinol-cytochrome c reductase iron-sulfur subunit, TonB-dependent receptor, carbon-nitrogen hydrolase, and ubiquinol oxidase subunit II.

18. The composition of paragraph 17, wherein the at least one bacterium comprises and expresses each of the enzymes membrane-bound PQQ-dependent glucose dehydrogenase (mGDH), ubiquinol-cytochrome c reductase iron-sulfur subunit, TonB-dependent receptor, carbon-nitrogen hydrolase, and ubiquinol oxidase subunit II.

19. The composition of paragraph 17 or 18, wherein the extract or fraction comprises one or more metabolites selected from gluconic acid, 2-keto-gluconic acid, 5-keto-gluconic acid, and 2,5-diketo-D-gluconic acid.

20. The composition of any one of paragraphs 17-19, wherein the extract or fraction is from bacterial cells cultured in a medium comprising: (i) standard Lysogeny broth (1% tryptone, 0.5% yeast extract, and 1% sodium chloride) containing 1% glucose, (ii) standard Hestrin-Schramm broth (D-glucose 2%, 0.5% yeast extract, 0.5% peptone, 0.27% disodium phosphate, 0.115% citric acid) or (iii) $CaCO_3$ medium comprising 8% glucose, 0.5% yeast extract, 0.2% mannitol, 0.05% magnesium sulphate, and 10% calcium carbonate.

21. The composition of any one of paragraphs 17-20, wherein the extract or fraction comprises metabolites or bacterial byproducts that promote ATP production in at least one cell type of a host mammal administered the composition.

22. The composition of any one of paragraphs 17-21, wherein the extract or fraction does not comprise viable bacterial cells.

23. The composition of any one of paragraphs 17-22, wherein the extract or fraction lacks detectable bacteria.

24. The composition of any one of paragraphs 17-23, wherein the extract or fraction further comprises attenuated or heat-inactivated bacteria.

25. The composition of any one of paragraphs 17-24, wherein the bacterium is from the Acetobacteriaceae family.

26. The composition of paragraph 25, wherein the bacterium is *Gluconobacter* spp (e.g., *Gluconobacter* EBT 405), *Acetobacter* spp., *Gluconoacaetobacter* spp., *Acidomonas* spp, *Ameyamaea* spp., *Asaia* spp., *Granuhbacter* spp., *Kozakia* spp., *Neoasaia* spp., *Neokomagataea* spp., *Saccharibacter* spp., *Swaminathania* spp., or *Tanticharoenia* spp.

27. The composition of any one of paragraphs 17-26, wherein one or more of the nucleic acid sequences is/are an exogenous nucleic acid sequence(s).

28. The composition of any one of paragraphs 17-27, wherein the composition is formulated as a food, a beverage, a feed composition, a nutritional supplement, or a pharmaceutical composition.

29. The composition of any one of paragraphs 17-28, wherein the composition further comprises a pharmaceutically acceptable carrier.

30. The composition of any one of paragraphs 17-29, wherein the composition is formulated for oral administration.

31. A method for increasing cellular ATP production in at least one cell type of a subject in need thereof, the method comprising administering to the subject a composition comprising an amount of at least one non-pathogenic bacterium that comprises and expresses one or more nucleic acid sequences encoding one or more of membrane-bound PQQ-dependent glucose dehydrogenase (mGDH), ubiquinol-cytochrome c reductase iron-sulfur subunit, TonB-dependent receptor, carbon-nitrogen hydrolase, and ubiquinol oxidase subunit II, or an extract or fraction thereof, effective to increase cellular ATP production in at least one cell type.

32. The method of paragraph 31, wherein the at least one bacterium expresses each of membrane-bound of membrane-bound PQQ-dependent glucose dehydrogenase (mGDH), ubiquinol-cytochrome c reductase iron-sulfur subunit, TonB-dependent receptor, carbon-nitrogen hydrolase, and ubiquinol oxidase subunit II.

33. The method of any one of paragraphs 31-32, wherein the at least one bacterium produces one or more of gluconic acid, 2-keto-gluconic acid, 5-keto-gluconic acid, and 2,5-diketo-D-gluconic acid.

34. The method of any one of paragraphs 31-33, wherein the at least one bacterium produces each of gluconic acid, 2-keto-gluconic acid, 5-keto-gluconic acid, and 2,5-diketo-D-gluconic acid.

35. The method of any one of paragraphs 31-34, wherein one or more of the nucleic acid sequences is exogenous to the bacterium.

36. The method of any one of paragraphs 31-35, wherein the activity of complex I and/or complex II of the mitochondrial electron transport chain is increased in the one or more cell types.

37. The method of any one of paragraphs 31-36, wherein the administering increases mitochondrial membrane potential.

38. The method of any one of paragraphs 31-37, wherein the subject is human.

39. The method of any one of paragraphs 31-38, wherein expression of peroxisome proliferator-activated receptor gamma coactivator 1-α (PGC-1α), and/or mitochondrial transcription factor A (TFAM) is increased.

40. The method of any one of paragraphs 31-39, wherein AMP-activated protein kinase (AMPK) phosphorylation levels, nuclear respiratory factor-2 (Nrf2) protein levels, PGCα mRNA levels TFAM mRNA levels and/or mitochondrial DNA replication is increased.

41. The method of any one of paragraphs 31-40, wherein the mitochondrial DNA copy numbers (mtDNA) is increased.

42. The method of any one of paragraphs 31-41, wherein the method increases the developmental growth rate of a subject carrying a mutations in mitochondrial respiratory Complex I NADH:ubiquinone reductase.

43. The method of any one of paragraphs 31-42, wherein the expression of at least one mitochondrial β-oxidation enzyme is increased.

44. The method of paragraph 43, wherein the at least one mitochondrial β-oxidation enzyme is B0303.3, cpt-2, cpt-1, ech-1.2, or acdh-7.

45. The method of any one of paragraphs 31-44, wherein the longevity of the subject is increased.

46. The method of any one of paragraphs 31-45, wherein mitochondrial biogenesis is maintained or increased.

47. The method of any one of paragraphs 31-46, wherein cellular ATP production is increased by at least 10% compared to the cellular ATP production prior to administration of the composition.

48. A method for making a bacterial extract, the method comprising culturing at least one bacterium that comprises and expresses one or more nucleic acid sequences encoding one or more of membrane-bound PQQ-dependent glucose dehydrogenase (mGDH), ubiquinol-cytochrome c reductase iron-sulfur subunit, TonB-dependent receptor, carbon-nitrogen hydrolase, and ubiquinol oxidase subunit II in a medium comprising: (i) standard Lysogeny broth (1% tryptone, 0.5% yeast extract, and 1% sodium chloride) containing 1% glucose, (ii) standard Hestrin-Schramm broth (D-glucose 2%, 0.5% yeast extract, 0.5% peptone, 0.27% disodium phosphate, 0.115% citric acid) or (iii) $CaCO_3$ medium comprising 8% glucose, 0.5% yeast extract, 0.2% mannitol, 0.05% magnesium sulphate, and 10% calcium carbonate.

49. The method of paragraph 48, wherein the at least one bacterium comprises and expresses nucleic acid sequences encoding each of membrane-bound PQQ-dependent glucose dehydrogenase (mGDH), ubiquinol-cytochrome c reductase iron-sulfur subunit, TonB-dependent receptor, carbon-nitrogen hydrolase, and ubiquinol oxidase subunit II.

50. The method of paragraph 48 or 49, wherein the at least one bacterium produces one or more of gluconic acid, 2-keto-gluconic acid, 5-keto-gluconic acid, and 2,5-diketo-D-gluconic acid.

51. A composition comprising an amount of gluconic acid, 2-keto-gluconic acid, 5-keto-gluconic acid, and/or 2,5-diketo-D-gluconic acid effective to increase cellular ATP production in at least one cell type of a host mammal administered the composition.

52. A composition comprising an amount of gluconic acid, 2-keto-gluconic acid, 5-keto-gluconic acid, and/or 2,5-diketo-D-gluconic acid effective to increase the expression and/or activity of mitochondrial transcription factor A (TFAM), or peroxisome proliferator activated receptor gamma coactivator 1 (PGC) in at least one cell type of a human subject administered the composition.

53. The composition of paragraph 51 or 52, wherein the composition comprises a bacterial extract or active fraction thereof.

54. The composition of paragraph 51, 52 or 53, wherein the composition is formulated as a food, a beverage, a feed composition, a nutritional supplement, or a pharmaceutical composition.

55. A method of treating Parkinson's disease, the method comprising administering to a subject having Parkinson's disease, a composition comprising a therapeutically effective amount of at least one bacterium that comprises and expresses one or more nucleic acid sequences encoding one or more of membrane-bound PQQ-dependent glucose dehydrogenase (mGDH), ubiquinol-cytochrome c reductase iron-sulfur subunit, TonB-dependent receptor, carbon-nitrogen hydrolase, and ubiquinol oxidase subunit II, or an extract or fraction thereof, thereby reducing at least one symptom of Parkinson's disease.

56. The method of paragraph 55, wherein the at least one bacterium expresses each of membrane-bound PQQ-dependent glucose dehydrogenase (mGDH), ubiquinol-cytochrome c reductase iron-sulfur subunit, TonB-dependent receptor, carbon-nitrogen hydrolase, and ubiquinol oxidase subunit II.

58. The method of paragraph 55 or 56, wherein the at least one bacterium produces one or more of gluconic acid, 2-keto-gluconic acid, 5-keto-gluconic acid, and/or 2,5-diketo-D-gluconic acid 59. The method of any one of paragraphs 55-58, wherein (i) the at least one bacterium produces each of gluconic acid, 2-keto-gluconic acid, 5-keto-gluconic acid, and/or 2,5-diketo-D-gluconic acid and/or (ii) the bacterium comprises *Gluconobacter* EBT 405.

60. The method of any one of paragraphs 55-59, wherein the at least one symptom is selected from the group consisting of: tremor, sleep disturbance, mobility impairment, involuntary movement, muscle rigidity, rhythmic muscle contraction, slow bodily movement, slow shuffling gait, fatigue, dizziness, impaired balance, restlessness, amnesia, confusion, dementia, cognitive impairment, impaired speech, anxiety, apathy, distorted or loss of sense of smell, urinary incontinence, reduced facial expression, weight loss and constipation.

61. A method of treating a mitochondrial electron transport chain disorder, the method comprising administering to a subject having a mitochondrial electron transport chain disorder, a composition comprising a therapeutically effective amount of at least one bacterium that comprises and expresses one or more nucleic acid sequences encoding one or more of membrane-bound PQQ-dependent glucose dehydrogenase (mGDH), ubiquinol-cytochrome c reductase iron-sulfur subunit, TonB-dependent receptor, carbon-nitrogen hydrolase, and ubiquinol oxidase subunit II, or an extract or fraction thereof, thereby reducing at least one symptom of the mitochondrial electron transport chain disorder.

62. The method of paragraph 61, wherein the mitochondrial electron transport chain disorder comprises a disorder or impaired activity in Complex I and/or Complex II.

63. The method of paragraph 61 or 62, wherein the mitochondrial electron transport chain disorder is NADH dehydrogenase (NADH-CoQ reductase) deficiency, succinate dehydrogenase deficiency, Leigh Disease, mitochondrial DNA depletion, or mitochondrial insufficiency.

64. The method of any one of paragraphs 61-63, wherein the at least one symptom is selected from the group consisting of: myopathy, mitochondrial encephalomyopathy, failure to thrive, developmental delay, hypotonia, lethargy, respiratory failure, ataxia, myoclonus, lactic acidosis, seizures, fatigue, nystagmus, poor reflexes, difficulty eating or swallowing, breathing difficulties, ataxia, congenital myopathy, infantile myopathy and hepatopathy.

65. The method of any one of paragraphs 61-64, wherein the at least one bacterium expresses each of membrane-bound PQQ-dependent glucose dehydrogenase (mGDH), ubiquinol-cytochrome c reductase iron-sulfur subunit, TonB-dependent receptor, carbon-nitrogen hydrolase, and ubiquinol oxidase subunit II.

66. The method of any one of paragraphs 61-65, wherein the at least one bacterium produces one or more of gluconic acid, 2-keto-gluconic acid, 5-keto-gluconic acid, and/or 2,5-diketo-D-gluconic acid.

67. The method of any one of paragraphs 61-66, wherein the at least one bacterium produces each of gluconic acid, 2-keto-gluconic acid, 5-keto-gluconic acid, and/or 2,5-diketo-D-gluconic acid.

68. A method of treating a peroxisomal disorder, the method comprising administering to a subject having a peroxisomal disorder, a composition comprising a therapeutically effective amount of at least one bacterium that comprises one or more nucleic acid sequences such that the bacterium expresses the following enzymes: membrane-bound PQQ-dependent glucose dehydrogenase (mGDH), ubiquinol-cytochrome c reductase iron-sulfur subunit, TonB-dependent receptor, carbon-nitrogen hydrolase, and ubiquinol oxidase subunit II, or a bacterial extract thereof, thereby reducing at least one symptom of the peroxisomal disorder.

69. The method of paragraph 68, wherein the peroxisomal disorder is Zellweger syndrome spectrum (PBD-ZSD), or rhizomelic chondrodysplasia punctate type 1 (RCDP1).

70. The method of paragraph 68 or 69, wherein the PBD-ZSD is infantile Refsum disease, neonatal adrenoleukodystrophy, or Zellweger syndrome.

71. The method of any one of paragraphs 68-70, wherein the at least one symptom is selected from the group consisting of: skeletal and craniofacial dysmorphism, liver dysfunction, progressive sensorineural hearing loss and retinopathy.

72. The method of any one of paragraphs 68-71, wherein the at least one bacterium expresses each of membrane-bound PQQ-dependent glucose dehydrogenase (mGDH), ubiquinol-cytochrome c reductase iron-sulfur subunit, TonB-dependent receptor, carbon-nitrogen hydrolase, and ubiquinol oxidase subunit II.

73. The method of any one of paragraphs 68-72, wherein the at least one bacterium produces one or more of gluconic acid, 2-keto-gluconic acid, 5-keto-gluconic acid, and/or 2,5-diketo-D-gluconic acid.

74. The method of any one of paragraphs 68-73, wherein the at least one bacterium produces each of gluconic acid, 2-keto-gluconic acid, 5-keto-gluconic acid, and/or 2,5-diketo-D-gluconic acid.

75. A method for increasing the biogenesis of cellular mitochondria or peroxisomes, the method comprising administering to a subject, a composition comprising an amount of at least one bacterium that comprises and expresses one or more nucleic acid sequences encoding membrane-bound PQQ-dependent glucose dehydrogenase (mGDH), ubiquinol-cytochrome c reductase iron-sulfur subunit, TonB-dependent receptor, carbon-nitrogen hydrolase, and ubiquinol oxidase subunit II, or a fraction or extract thereof, effective to increase the biogenesis of cellular mitochondria or peroxisomes.

76. The method of paragraph 75, wherein the size and/or number of peroxisomes is increased.

77. The method of paragraph 75 or 76, wherein mitochondrial activity is increased.

78. The method of paragraph 75, 76, or 77, wherein the at least one bacterium expresses each of encoding membrane-bound PQQ-dependent glucose dehydrogenase (mGDH), ubiquinol-cytochrome c reductase iron-sulfur subunit, TonB-dependent receptor, carbon-nitrogen hydrolase, and ubiquinol oxidase subunit II.

79. The method of any one of paragraphs 75-78, wherein the at least one bacterium produces one or more of gluconic acid, 2-keto-gluconic acid, 5-keto-gluconic acid, and/or 2,5-diketo-D-gluconic acid.

80. The method of any one of paragraphs 75-79, wherein the at least one bacterium produces each of gluconic acid, 2-keto-gluconic acid, 5-keto-gluconic acid, and/or 2,5-diketo-D-gluconic acid.

81. A method of treating Alzheimer's disease, the method comprising administering to a subject having Alzheimer's disease, a composition comprising a therapeutically effective amount of at least one bacterium that comprises and expresses one or more nucleic acid sequences encoding one or more of membrane-bound PQQ-dependent glucose dehydrogenase (mGDH), ubiquinol-cytochrome c reductase iron-sulfur subunit, TonB-dependent receptor, carbon-nitrogen hydrolase, and ubiquinol oxidase subunit II, or an extract or fraction thereof, thereby reducing at least one symptom of Alzheimer's disease.

82. The method of paragraph 81, wherein the at least one bacterium expresses each of membrane-bound PQQ-dependent glucose dehydrogenase (mGDH), ubiquinol-cytochrome c reductase iron-sulfur subunit, TonB-dependent receptor, carbon-nitrogen hydrolase, and ubiquinol oxidase subunit II.

83. The method of paragraph 81 or 82, wherein the at least one bacterium produces one or more of gluconic acid, 2-keto-gluconic acid, 5-keto-gluconic acid, and/or 2,5-diketo-D-gluconic acid 84. The method of paragraph 81, 82 or 83, wherein the at least one bacterium produces each of gluconic acid, 2-keto-gluconic acid, 5-keto-gluconic acid, and/or 2,5-diketo-D-gluconic acid.

85. The method of any one of paragraphs 81-84, wherein the at least one symptom is selected from the group consisting of: cognitive decline, confusion, delusion, disorientation, forgetfulness, difficulty concentrating, inability to generate new memories, inability to do simple math, inability to recognize common items, aggression, agitation, irritability, meaningless repetition of own words, personality changes, restlessness, lack of restraint, wandering, anger, apathy, general discontent, loneliness, mood swings, depression, hallucination, paranoia, loss of appetite, inability to combine muscle movements and jumbled speech.

86. The method of any one of paragraphs 81-85, wherein the bacterium comprises *Gluconobacter* EBT 405.

EXAMPLES

The following provides non-limiting Examples demonstrating and supporting the technology as described herein.

Example 1: Results

Six microbes that suppress the slow developmental growth rate phenotype of three mitochondrial mutants of *C. elegans*: spg-7(ad2249)[1], gas-1(fc21)[2], and nduf-7(et19)[3] were identified using a qualitative visual screen. spg-7 encodes a homolog of AFG3L2, which is a conserved m-AAA metalloprotease[1]. Along with another m-AAA metalloprotease paraplegin, AFG3L2 is involved in the removal of abnormal proteins from the mitochondria and thus maintenance of the mitochondrial proteome. nduf-7 encodes NADH-ubiquinone oxidoreductase Fe—S, which is a component of complex I in the mitochondrial electron transport chain[3]. gas-1 encodes a NADH dehydrogenase [ubiquinone] iron-sulfur protein 2, which is a component of complex I in the mitochondrial electron transport chain[2]. gas-1(fc21) mutant animals exhibit significantly decreased mitochondrial mass and membrane potential and thus, reduced respiratory capacity[4,5,6]. spg-7(ad2249), gas-1(fc21), and nduf-7(et19) mutants grow at a significantly slower rate compared to the wildtype animals (FIG. 1A) when fed on *E. coli* OP50. *E. coli* OP50 is the standard microbial strain on which *Caenorhabditis elegans* are typically grown in the laboratory. A screen was performed to test whether any of the microbes that are naturally associated with *C. elegans* in the wild can modify the slow growth phenotype of the mitochondrial mutants. In the screen, ~200 strains of wild microbes were fed individually to synchronized L1-stage spg-7(ad2249), gas-1(fc21), and nduf-7(et19) mutants. Mutant animals that grew at a significantly faster rate compared to the animals fed on *E. coli* OP50 (FIG. 5A) were identified. In this screen, 6 microbes were identified that partially suppress the slow growth phenotype of the mitochondrial mutants. This study focuses on three of the microbes: *Gluconacetobacter* spp, *Acetobacter* spp, and *Gluconobacter* spp (FIG. 5A). Each of these microbes belong to the family Acetobacteraceae of the phylum Proteobacteria and are characterized by the ability to oxidize sugars or ethanol and produce acetic acid during fermentation[7]. They are naturally present in sugary and acidic niches such as fruits'[8] and particularly in fermented beverages such as natural Apple cider vinegar[9] and Kombucha[10]. Interestingly, it was found that these three bacteria (i.e., *Gluconobacter, Acetobacter*, and *Gluconoacetobacter*) were able to accelerate the developmental growth rate of even wildtype animals (FIGS. 5B-5D). Among the three species, *Gluconacetobacter* spp were comparatively better in accelerating the developmental growth rate (FIGS. 5A-5B). To determine specifically how *Gluconacetobacter* spp enhance developmental growth rate, the developmental acceleration rate was examined at each larval stage. It was found that *Gluconacetobacter* spp feeding specifically shortened the time taken for animals to reach egg-laying adult stage from L4-larval stage (FIGS. 5E-5F).

To test whether the enhancement of developmental growth rate was general for all mitochondrial mutants, mutations in other mitochondrial respiratory chain namely mev-1(kn1) and isp-1(qm150) were tested. mev-1 encodes a subunit of succinate-coenzyme Q oxidoreductase in the complex II of mitochondrial electron transport chain[11]. isp-1 is an iron sulfur protein (isp-1) of cytochrome bc1 complex (complex III)[12]. *Gluconacetobacter* spp feeding failed to suppress the slow developmental growth rate of mev-1(kn1) and isp-1(qm150) mutants, indicating that enhancement of complex I and/or complex II activity is a likely mode-of-action. It was hypothesized that *Gluconacetobacter* spp feeding might enhance the developmental growth rate of wildtype and the mitochondrial mutants by increasing the mitochondrial ATP production. To test this hypothesis, a transgenic firefly luciferase-expressing *C. elegans* strain[13] was used for rapid in vivo assessment of the ATP levels. Transgenic luciferase expressing strain fed on *Gluconacetobacter* spp had higher bioluminescence compared to the animals fed on *E. coli* OP50, indicating increased ATP content (FIG. 1B). This result was confirmed using an in vitro ATP determination assay (FIG. 1C). An increase in bioluminescence was observed as quickly as within 6 hours of initiating feeding with *Gluconacetobacter* spp (FIG. 5G). Further, it was found that the ATP levels were reduced in spg-7(ad2249) mutant fed on *E. coli* OP50 compared to the wildtype animals fed on *E. coli* OP50. In addition, *Gluconacetobacter* spp feeding was able to restore the ATP content of spg-7(ad2249) mutant (FIG. 1D). Similarly, it was found that *Gluconacetobacter* spp feeding was able to partially restore the ATP content of nduf-7(et19) mutant (FIG. 1E).

It was found that the mitochondrial membrane potential was significantly decreased in spg-7(ad2249), gas-1(fc21), and nduf-7(et19) mutants fed on *E. coli* OP50 compared to the wildtype animals fed on *E. coli* OP50 as assessed using Mitotracker™ CMXRos (FIG. 1F). Mitotracker™ CMXRos stains mitochondria and its accumulation in live cells is dependent upon membrane potential. *Gluconacetobacter* spp feeding was able to partially restore the mitochondrial membrane potential of spg-7(ad2249), gas-1(fc21), and nduf-7(et19) mutants (FIG. 1F). Using another dye, Tetramethylrhodamine, ethyl ester (TMRE), which is sequestered by active mitochondria, it was found that spg-7(ad2249) mutants fed on *Gluconacetobacter* spp had significantly increased dye levels compared to animals fed on *E. coli* OP50 (FIG. 5H) indicating that the mitochondrial membrane potential was increased.

Next, the effect of different mitochondrial poisons on the increased ATP production phenotype of animals fed on *Gluconacetobacter* spp was assessed. It was found that animals fed on *Gluconacetobacter* spp and treated with Rotenone or Paraquat or Sodium Azide had significantly higher levels of bioluminescence compared to animals fed on *E. coli* OP50 and treated with Rotenone or Paraquat or Sodium Azide (FIGS. 1G-1H; FIG. 5I). Both Paraquat (1,1'-dimethyl-4,4'-bipyridinium dichloride) and Rotenone are inhibitors of complex I in the mitochondrial electron transport chain while Sodium Azide and Antimycin are inhibitors of complex III.

It was found that animals fed on *Gluconacetobacter* spp were more resistant to Rotenone or Paraquat than animals fed on *E. coli* OP50 (FIG. 6A). However, animals fed on *Gluconacetobacter* spp were not more resistant to Sodium Azide or Antimycin compared to animals fed on *E. coli* OP50 (FIG. 6A).

The unfolded protein response of the mitochondria (UPR$^{mt}$) is initiated by mitochondrial stress and activates the expression of several nuclear genes, including the hsp-6 mitochondrial chaperone[14]. Using a hsp-6::gfp transgenic animal strain, it was determined whether *Gluconacetobacter* spp affects UPR$^{mt}$ induction. Transgenic hsp-6::gfp animals fed on *E. coli* OP50 or *Gluconacetobacter* spp were treated with either MPP+ or 6-OHDA or Paraquat and induction of GFP expression was assessed after 24 hours of treatment. MPTP [1-methyl-4-phenylpyridinium (MPP+)] and 6-hydroxydopamine (6-OHDA) are neurotoxins that induce ROS production and are used in animal models of Parkinson's Disease (PD). While worms fed *E. coli* OP50 and treated with either MPP+ or 6-OHDA or Paraquat induced GFP expression, worms fed on *Gluconacetobacter* spp failed to induce GFP expression (FIG. 2A). Genetic mutations in gas-1(fc21), nduf-7(et19), mev-1(kn1) and isp-1(qm150) induced hsp-6::gfp expression constitutively. Feeding these mutants on *Gluconacetobacter* spp did not suppress the hsp-6::gfp expression. While the induction of hsp-6::gfp during UPR$^{mt}$ is mediated by the ATFS-1 transcription factor[15], a subset of the genes upregulated in UPR$^{mt}$ are activated in an ATFS-1 independent fashion. Recently, tbb-6, which encodes an uncharacterized β-tubulin, was shown to be upregulated independently of ATFS-1 following mitochondrial ETC disruption[16]. A tbb-6::gfp transgenic strain was generated and it was found this GFP was induced in the spg-7 (ad 2249) mutant (FIG. 6B; FIG. 2B). Feeding spg-7 (ad2249); tbb-6::gfp animals on *Gluconacetobacter* spp suppressed the tbb-6::gfp expression (FIG. 6B; FIG. 2B).

To address how *Gluconacetobacter* spp feeding improves mitochondrial function, a variety of transgenic worm strains were tested, including worms that carry a construct encoding a fusion protein comprising a GFP reporter protein and a gene product that is involved in stress response, mitochondrial activity, peroxisomal function, innate immune response, and different signaling pathways (Table 1; FIGS. 2C-2K; FIGS. 6C-6L; FIGS. 7A-7D).

TABLE 1

| Transcriptional GFP fusion gene | Gene description |
| --- | --- |
| cyp-35B1 | Cytochrome P450 |
| haf-7 | ABC-type multidrug transport system |
| ugt-61 | UDP-glucuronosyl and UDP-glucosyl transferase |
| pgp-3 | ABC-type multidrug transport system |
| mrp-2 | ABC-type multidrug transport system |
| abch-1 | ABC-type multidrug transport system |
| pmp-4 | ABC-type multidrug transport system |
| ugt-58 | UDP-glucuronosyl and UDP-glucosyl transferase |
| dhs-9 | short-chain dehydrogenases/reductases family (SDR) |
| cyp-37A1 | Cytochrome P450 |
| dhs-19 | short-chain dehydrogenases/reductases family (SDR) |
| cyp-34A9 | Cytochrome P450 |
| cyp-14A3 | Cytochrome P450 |
| ugt-8 | UDP-glucuronosyl and UDP-glucosyl transferase |
| cyp-13a7 | Cytochrome P450 |
| pgp-4 | ABC-type multidrug transport system |
| cyp-31a3 | Cytochrome P450 |
| pgp-6 | ABC-type multidrug transport system |
| cyp-25a2 | Cytochrome P450 |
| ugt-22 | UDP-glucuronosyl and UDP-glucosyl transferase |
| pgp-9 | ABC-type multidrug transport system |
| pgp-5 | ABC-type multidrug transport system |
| sod-3 | Superoxide dismutase/daf-16 target |
| gst-4 | Glutathione S-transferase/oxidative stress reporter |
| gcs-1 | Gamma GlutamylCysteine Synthetase/oxidative stress reporter |
| hsp-60 | Mitochondrial specific chaperone of GroE/Hsp 10/60 family |
| hsp-4 | Heat shock response 70 (hsp70) protein/Endoplasmic reticulum stress reporter |
| hsp-6 | Mitochondrion-specific chaperone of the DnaK/Hsp70family/mitochondrial stress reporter |
| nlp-29 | Neuropeptide like protein/Anti-fungal innate immune response reporter |
| clec-60 | C-type lectin family/innate immune response reporter |

TABLE 1-continued

| Transcriptional GFP fusion gene | Gene description |
| --- | --- |
| irg-1 | Innate immune response reporter |
| hsp-16.2 | Heat shock protein of hsp16/hsp20/alphaB-crystallin (HSP16) family/heat shock reporter |
| nhr-57 | Nuclear hormone receptor; hypoxia stress reporter |
| rpt-3 | triple A ATPase subunit of the 26S proteasome's 19S regulatory particle (RP) base subcomplex |
| fat-7 | delta-9 fatty acid desaturase |
| tbb-6 | human TUBB8 (tubulin beta 8 class VIII) |
| hphd-1 | human ADHFE1 (alcohol dehydrogenase, iron containing 1) |
| B0303.3 | 3-Keto-coA thiolase beta-subunit of Trifunctional protein (HADHB) |
| prx-11 | vertebrate peroxisomal membrane protein 11C |
| cpt-2 | carnitine palmitoyltransferase |
| acox-1.2 | ACOX1 (acyl-CoA oxidase 1) |
| ech-1.2 | enoyl-CoA hydratases/long-chain 3-hydroxyacyl-CoA dehydrogenases |
| acdh-7 | ACADM (acyl-CoA dehydrogenase, C-4 to C-12 straight chain) |
| prx-6 | Pex6 (peroxisomal biogenesis factor 6) |
| cpt-1 | Carnitine Palmitoyltransferase I |
| icl-1 | isocitrate lyase/malate synthase, an enzyme known to function in the glyoxylate cycle |
| lgg-1 | ortholog of Saccharomyces cerevisiae Atg8p and mammalian MAP-LC3 |
| UbV-gfp | a UFD model substrate in which a noncleavable ubiquitin is N-terminally fused to GFP (UbV-GFP) |
| lipl-1 | human Lipases family including LIPF |
| hsp-70 | heat-shock protein that is a member of the hsp70 family of molecular chaperones |
| ftn-2 | ferritin heavy chain homolog |
| ftn-1 | ferritin heavy chain homolog |
| fzo-1 | GTPase orthologous to MFNl(Mitofusin)/FZO1 |
| crtc-1 | CREB-regulated transcriptional coactivator orthologous to mammalian CRTCs |
| cts-1 | citrate synthase |
| acdh-1 | Short-chain acyl-CoA dehydrogenase |
| acdh-2 | short-chain acyl-CoA dehydrogenase |
| acdh-11 | acyl-CoA dehydrogenase |
| ads-1 | AGPS (alkylglycerone phosphate synthase |
| agxt-1 | Alanine-Glyoxylate aminotransferase (AGXT) |
| acox-1.6 | ACOX1 (acyl-CoA oxidase 1) |
| nhr-64 | NR2 subfamily of nuclear receptors that contains Drosophila and human HNF4 |
| daf-22 | ortholog of human sterol carrier protein SCP2 |
| nhr-69 | NR2 subfamily of nuclear receptors that contains Drosophila and human HNF4 |
| spg-20 | human SPG20 (spastic paraplegia 20 (Troyer syndrome) |
| cyp-29A2 | CYP19A1 (cytochrome P450 family 19 subfamily A member 1) |
| dhs-28 | human 17-BETA-HYDROXYSTEROID DEHYDROGENASE 4 (HSD17B4 |
| mtl-1 | metallothioneins, small, cysteine-rich, metal-binding proteins |
| kap-1 | kinesin-associated protein |
| C01H6.4 | N,N-dimethylaniline monooxygenase activity |
| tmem-135 | TMEM135 (transmembrane protein 135) |
| C53B4.3 | Solute Carrier Family 22 (Organic Cation Transporter), Member 18 |
| far-3 | Fatty Acid/Retinol binding protein |
| irg-4 | CUB-like domain-containing protein |
| irg-5 | Infection Response Gene |
| lys-7 | antimicrobial lysozyme encoded by the LYS4 |
| abf-1 | antibacterial factor ASABF |
| abf-3 | antibacterial factor ASABF |
| spp-7 | SPP-protein family, called caenopores |
| lys-1 | putative lysozyme |
| dod-22 | human EPHX1 (epoxide hydrolase 1) |
| F55G11.7 | human EPHX1 (epoxide hydrolase 1) |
| K08D8.5 | CUB-like domain-containing protein |
| clec-85 | C-type LECtin |
| F10A3.4 | Nematode-specific gene |

In this screen, it was found that *Gluconacetobacter* spp feeding induced the expression of a subset of genes required for either mitochondrial function or peroxisomal activity. These include B0303.3 (ortholog of human HADHB [3-Ketoacyl-coA Thiolase beta subunit]) (FIG. 2D; FIG. 6H), prx-11 (ortholog of human PEX11G [peroxisomal biogenesis factor 11G]) (FIG. 2E), cpt-2 (ortholog of human CPT2 [Carnitine Palmitoyl transferase]) (FIG. 2F; FIG. 6C), acox-1.2 (ortholog of human ACOX1 [Acyl CoA oxidase 1]) (FIG. 2G; FIG. 6D; FIG. 6J), ech-1.2 (ortholog of human HADHA [3-Ketoacyl-coA Thiolase alpha subunit]) (FIG. 2H; FIG. 6G), acdh-7 (ortholog of human ACADM [Acyl-CoA dehydrogenase, medium-chain]) (FIG. 2I; FIG. 6F, FIG. 6I), pmp-4 (ortholog of human ABCD1 [peroxisomal membrane ABC transporter]) (FIG. 2J; FIG. 6E), prx-6 (ortholog of human PEX6 [peroxisomal biogenesis factor 6]) (FIG. 2K), cpt-1 (ortholog of human CPT1 [Carnitine Palmitoyl transferase]) (FIG. 6K), and icl-1 (encodes isocitrate lyase/malate synthase) (FIG. 7A). Expression of one gene, hphd-1 (an ortholog of Human ADHFE1 [Alcohol dehydrogenase]) was significantly reduced in worms fed on *Gluconacetobacter* spp (FIG. 2C). CPT (carnitine 0-palmitoyltransferase) and ACADM (medium chain acyl CoA dehydrogenase) each play a pivotal role in mitochondrial fatty acid uptake and β-oxidation, two critical steps for energy production from fatty acids. Similarly, HADHA and HADHB encode the alpha and beta subunit of the mitochondrial hydroxyacyl-CoA dehydrogenase/3-ketoacyl-CoA thiolase/enoyl-CoA hydratase (trifunctional protein), which catalyzes mitochondrial beta-oxidation of long chain fatty acids. ACOX1 catalyzes the desaturation of acyl-CoAs to 2-trans-enoyl-CoAs and is the first enzyme of the peroxisomal fatty acid beta-oxidation pathway. ICL-1 functions in the glyoxylate shunt, which converts isocitrate and acetyl-CoA to succinate, malate, and CoA using glyoxylate as an intermediate[17]. It was found that the *Gluconacetobacter* spp feeding induced cpt-2::gfp and that ech-1.2::gfp expression was dependent on tcer-1 (ortholog of TCERG1 [Transcription elongation regulator 1])[18,19] (FIGS. 2F & 2H) while acox-1.2 (FIG. 2G), acdh-7 (FIG. 2I), pmp-4 (FIG. 2J), and prx-6 (FIG. 2K), expression was dependent on nhr-49 (encodes a nuclear hormone receptor with sequence similarity to HNF4a but functionally resemble more like peroxisome proliferator-activated receptor alpha (PPARα)[20]. tcer-1 (tm1452) and nhr-49(nr2041) animals fed on *Gluconacetobacter* spp feeding grew slower compared to wildtype worms fed on *Gluconacetobacter* spp (FIG. 3A) indicating that TCER-1 and NHR-49 activities promote accelerated developmental growth rate. Intestine-specific overexpression of nhr-49 was sufficient to accelerate growth rate of nhr-49(nr2041) mutants fed on *Gluconacetobacter* spp (FIG. 7E). Further, a strong induction of nhr-49::gfp was observed in the worms fed on *Gluconacetobacter* spp (FIG. 7F). To test whether NHR-49 itself is sufficient to accelerate developmental growth rate, gain-of-function alleles were determined in nhr-49(et7), nhr-49(et8), nhr-49(et13)[21]. None of these strains had accelerated growth rate phenotype when fed on *E. coli* OP50, while they still showed accelerated growth when fed on *Gluconacetobacter* spp.

In addition, a strong nuclear localization of TCER-1::GFP was observed in the intestinal cells of worms fed on *Gluconacetobacter* spp compared to worms fed on *E. coli* OP50 (FIG. 7G).

Since genes associated with peroxisomal function were upregulated in response to *Gluconacetobacter* spp feeding, it was tested whether RNAi of peroxisomal genes affect the accelerated developmental growth rate phenotype. RNAi of prx-5 (ortholog of PXR1 or PEX5 [human receptor for type I peroxisomal targeting signal protein]) or prx-11 (ortholog of human PEX11G [peroxisomal biogenesis factor 11G]) suppressed the accelerated developmental growth rate phenotype of wildtype worms fed on *Gluconacetobacter* spp (FIG. 3A). It was found that RNAi of tcer-1, nhr-49, and prx-5 suppressed the *Gluconacetobacter* spp feeding-induced increase in bioluminescence phenotype (FIG. 3B), indicating that these genes are required for increased ATP production upon *Gluconacetobacter* spp feeding. Further, RNAi of nhr-49 or prx-5 was able to suppress the accelerated developmental progression phenotype of spg-7 (ad2249) and nduf-7(et19) mutant worms fed on *Gluconacetobacter* spp (FIGS. 3C-3D). Compared to wildtype worms, spg-7(ad2249) mutant have reduced mitochondrial membrane potential as assessed using Mito CMXRos and this reduction was further exacerbated by nhr-49 RNAi (FIG. 3E). A partial reduction of mitochondrial membrane potential was observed in wildtype worms fed on nhr-49 RNAi (FIG. 3E).

To examine the effect of *Gluconacetobacter* spp feeding on the mitochondrial morphology, a transgenic strain was used that expresses a fusion protein of *C. elegans* mitochondrial import receptor subunit TOMM-20 and monomeric red fluorescent protein (mRFP) and the expression is driven in body wall muscle cells by the myo-3 promoter[22]. In the transgenic worms fed on *Gluconacetobacter* spp, the mitochondria appear to be more fused compared to the worms fed on *E. coli* OP50 (FIG. 3F). Using Rhodamine 6G dye, which stains mitochondria, it was determined that the mitochondria in the hypodermis of worms fed on *Gluconacetobacter* spp appear more fused compared to worms fed on *E. coli* OP50 (FIG. 7H). Mitochondria are dynamic organelles that constantly undergo fusion and fission events. The elongated morphology is associated with increased ATP production efficiency[23] and decreased ROS formation[24]. Thus, without wishing to be bound by theory, the increased number of fused mitochondria phenotype in worms fed on *Gluconacetobacter* spp may explain the increased ATP production phenotype. The mitochondrial fission and fusion dynamics are tightly regulated by drp-1 (Ortholog of human DNML1 [dynamin-related protein]) and fzo-1 (ortholog of human MFN1[Mitofusin]/FZO1GTPase)[25]. Mutants in fzo-1(tm1133) or drp-1(tm1108) are extremely slow-growing (takes 6 days to reach adulthood from L1-stage) when fed on *E. coli* OP50 or on *Gluconacetobacter* spp. Without wishing to be bound by theory, these data indicate that the beneficial effects of *Gluconacetobacter* spp on mitochondrial function might be via regulation of mitochondrial dynamics.

Since *Gluconacetobacter* spp feeding induced the expression of peroxisomal biogenesis factors, peroxisomes were examined using a transgenic strain that expresses DAF-22 fusion protein that was tagged with green fluorescent protein (GFP) at its N terminus, under the control of vha-6 intestinal promoter[26]. In this strain, a punctate signal is observed, which denotes the peroxisomal targeting of the GFP-DAF-22 fusion protein. An increase in the punctate structures was observed in worms fed on *Gluconacetobacter* spp, indicating an increase in peroxisomes (FIG. 3G). The punctate peroxisomal structures were not observed in worms that were treated with RNAi of prx-5 (ortholog of PXR1 or PEX5 [human receptor for type I peroxisomal targeting signal protein]), which is required for the targeting of GFP-DAF-22 fusion protein to the peroxisomes and fed on either *E. coli* OP50 or on *Gluconacetobacter* spp (FIG. 8A). This increase in peroxisomal numbers is specific, changes in the number or morphology of other subcellular structures such as Golgi, gut lysosomal granules, and Endoplasmic reticulum (FIG. 8B-8D) was not observed. Since peroxisomes are a major endogenous source of hydrogen peroxide ($H_2O_2$), it was examined whether *Gluconacetobacter* spp feeding increases $H_2O_2$. To measure endogenous $H_2O_2$ levels, transgenic jrIs1 [Prp1-17::HyPer] worms expressing HyPer sensor[27] were fed on *Gluconacetobacter* spp and *E. coli* OP50. Compared to the worms fed on *E. coli* OP50, worms fed on *Gluconacetobacter* spp had slightly lower levels of $H_2O_2$ indicating that *Gluconacetobacter* spp does not increase endogenous $H_2O_2$ production (FIG. 3H). Even in HyPer sensor worms fed on *Gluconacetobacter* spp and treated with $H_2O_2$ had slightly lower level of $H_2O_2$ levels compared to the worms fed on *E. coli* OP50 (FIG. 3H) indicating an increased efficiency of $H_2O_2$ detoxification. Consistent with this observation, worms fed on *Gluconacetobacter* spp and treated with $H_2O_2$ had slightly lower levels of $H_2O_2$ compared to the worms fed on *E. coli* OP50 as assessed using the Amplex red assay (FIG. 8E). One of the major ways in which organisms handle ROS such as $H_2O_2$ is through glutathione oxidation[27]. Using a transgenic worm strain that expresses Grx1-roGFP2, which is a ratiometric biosensor that detects glutathione redox potential[27], it was found that the glutathione intracellular concentrations were not affected in worms fed on *Gluconacetobacter* spp compared to worms fed on *E. coli* OP50 (FIG. 8F). Without wishing to be bound by theory, it is possible that worms fed on *Gluconacetobacter* spp have higher levels of peroxisomal catalases, which detoxifies $H_2O_2$.

Aging-related changes in mitochondria are associated with decline in mitochondrial activity[28]. In aging animals, impairment of mitochondrial function such as decreased oxidative capacity, decreased ATP production, reduced oxidative phosphorylation, and increased ROS production are observed[29]. Age-dependent decline in ATP production, metabolism, mitochondrial content and function were observed in *C. elegans*[30,31]. The effect of *Gluconacetobacter* spp feeding on mitochondrial function was assessed in aging worms. It was found that in worms fed on *E. coli* OP50, ATP levels decrease significantly as the worms age (FIG. 4A). However, worms fed on *Gluconacetobacter* spp had significantly higher ATP content compared to worms fed on *E. coli* OP50 even as the worms age (FIG. 4A). The effects of *Gluconacetobacter* spp feeding is dominant because mixture of *Gluconacetobacter* spp with *E. coli* OP50 was sufficient to induce increased ATP production (FIG. 4B).

To test whether the phenotypes associated with *Gluconacetobacter* spp feeding are strain-specific, the ATP production was assessed in response to other *Gluconacetobacter* strains. It was found that other *Gluconacetobacter* strains including *Gluconacetobacter hansenii* (MGH isolate), the canonical *Gluconacetobacter hanseni* ATCC 23769, and non-cellulose producing mutant of *G. hanseni* ATCC 23769 each induced increased ATP production compared worms fed on *E. coli* OP50 (FIG. 4C).

Further, a variety of *Gluconobacter* and *Acetobacter* strains were isolated from rotting apples and grapes, by selecting for bacteria that produce acids and form a characteristic clear halo around media plates containing $CaCO_3$[7] (FIG. 8G). All these microbes were able to induce increased ATP production compared to worms fed on *E. coli* OP50 (FIG. 4D) except for *G. kondanii* and *G. frateuri*, which were pathogenic to *C. elegans* (FIG. 4D).

One of the key questions that the inventors wanted to answer was how *Gluconacetobacter* spp feeding suppresses defects associated with mitochondrial mutants. To address this question, a forward genetic transposon screen for mutant microbial strains that failed to suppress the developmental growth phenotype of spg-7(ad2249) mutants was conducted. Since the *Gluconacetobacter* spp are very slow growing, the mutant screen was conducted on *Gluconobacter oxydans*. ~2000 *G. oxydans* transposon mutants were isolated and fed individually to synchronized L1-stage spg-7(ad2249) mutants. After 3 days of incubation, the worms were scored for percent of worms that reached L4-stage or adulthood. In this screen, 11 mutants were identified that failed to suppress the slow developmental growth phenotype of spg-7(ad2249) mutants (FIGS. 8H-8I). Further, these 11 mutants failed to accelerate the developmental growth rate of wildtype worms (FIG. 9A). In addition, in worms fed on mutants in membrane-bound PQQ-dependent glucose dehydrogenase (GOX0265; mGDH), Cytochrome o ubiquinol oxidase subunit II (GOX1911), and ubiquinol-cytochrome c reductase iron-sulfur subunit, the ATP production was decreased compared to worms fed on Wildtype *G. oxydans* (FIG. 4E). However, in the worms fed on mutants in Carbon-Nitrogen hydrolase and TonB-dependent outer membrane receptor protein, the ATP levels were similar to the worms fed on Wildtype *G. oxydans* (FIG. 4E).

It was next tested whether the *G. oxydans* mutants affect the ability to produce acids using the $CaCO_3$ clearance assay. It was found that mutants in membrane-bound PQQ-dependent glucose dehydrogenase (GOX0265; mGDH), Cytochrome o ubiquinol oxidase subunit II (GOX1911), ubiquinol-cytochrome c reductase iron-sulfur subunit, and Carbon-Nitrogen hydrolase fail to form a clear halo around media plates containing $CaCO_3$ (FIG. 5B).

Six independent alleles of a gene encoding for Membrane-bound PQQ-dependent glucose dehydrogenase (Table 2), which oxidizes D-glucose to D-gluconate that can be further oxidized to two different keto-D-gluconates, 2-keto-D-gluconate and 5-keto-D-gluconate, as well as 2,5-di-keto-D-gluconate[32,33] were isolated.

TABLE 2

|  | Alleles |
| --- | --- |
| Membrane bound glucose dehydrogenase | 6 |
| Cytochrome o ubiquinol oxidase | 1 |
| Ubiquinol-cytochrome C reductase iron-sulfur subunit | 1 |
| tonB-dependent receptor protein | 2 |
| Carbon nitrogen hydrolase | 1 |

Figure 9C:
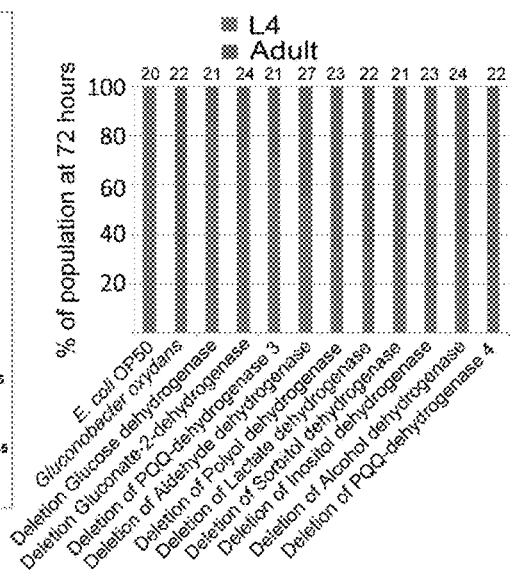

An independent deletion mutation in glucose dehydrogenase of *G. oxydans* isolated by another lab[34] also failed to suppress the slow developmental growth phenotype of spg-7(ad2249) mutants (FIG. 9C).

One of the characteristic attributes of acetic acid bacteria, including *G. oxydans*, is their ability to incompletely oxidize a variety of substrates including sugars[33]. This incomplete oxidation is catalyzed by various membrane-bound dehydrogenases including Membrane-bound PQQ-dependent glucose dehydrogenase[34]. Independent deletion alleles in various dehydrogenases were tested and it was found that spg-7(ad2249) mutant worms fed on deletion mutations in Membrane-bound PQQ-dependent glucose dehydrogenase, FAD-dependent Membrane-bound dehydrogenase, and Membrane-bound PQQ-dependent dehydrogenase 3 grew slower compared to worms fed on wildtype *G. oxydans* (FIG. 9C). FAD-dependent membrane-bound dehydrogenase is the D-gluconate-2-dehydrogenase, which oxidizes D-gluconate to 2-keto-gluconate[34]. The function of Membrane-bound PQQ-dependent dehydrogenase 3 is not known. Further, it was found that ATP production was decreased in worms fed on deletion mutations in Membrane-bound PQQ-dependent glucose dehydrogenase, FAD-dependent Membrane-bound dehydrogenase, and Membrane-bound PQQ-dependent dehydrogenase 3 compared to worms fed on wildtype *G. oxydans* (FIG. 4F).

Figure 9D:
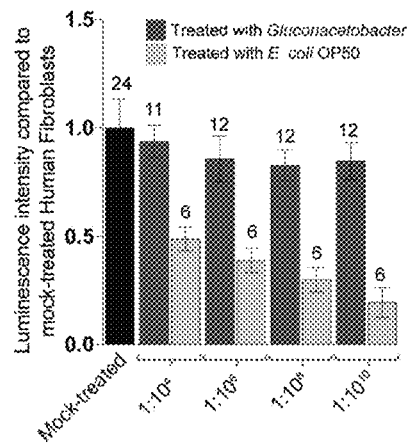
Figure 9E:
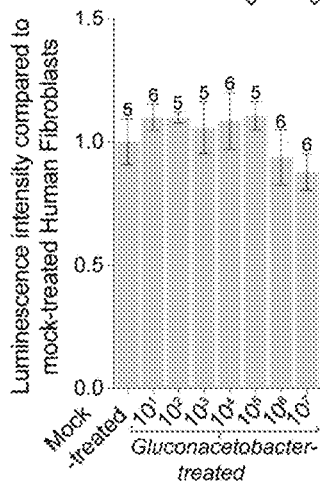

To determine whether *Gluconacetobacter* spp has similar biological effects in humans, human primary dermal fibroblasts were exposed to *Gluconacetobacter* spp and *E. coli* OP50. Exposure of *E. coli* OP50 to human primary dermal fibroblasts results in significant reduction in the ATP production while *Gluconacetobacter* spp does not affect ATP production compared to the mock-treated cells (FIG. 9D-9E). Since ATP levels are an indicator of metabolically active cells, which is a measure of cellular viability, the reduction of ATP levels in cells exposed to *E. coli* OP50 is an indicator of cell death or reduced viability. Without wishing to be bound by theory, the reduced viability may be a result of infection. Interestingly, *Gluconacetobacter* spp does not reduce the cellular ATP production even at higher doses of the bacteria (Fig.S5E) indicating that *Gluconacetobacter* spp is not toxic or pathogenic to cells. PGC-1α (Peroxisome proliferator-activated receptor gamma coactivator 1-alpha) is the master regulator of mitochondrial biogenesis and it regulates several genes involved in energy metabolism by its interaction with the nuclear hormone receptor, PPAR alpha[35]. Using RT-QPCR, it was found that PGC-1α gene expression was increased in human primary dermal fibroblasts exposed to *Gluconacetobacter* spp compared to mock-treated cells (FIG. 4H). PGC-1α induces the transcription of nuclear respiratory factor 1, leading to the increased expression of mitochondrial transcription factor A (TFAM)[36,37]. TFAM is the master regulator of mitochondrial phosphorylative oxidation (mOXPHOS) required for mitochondrial transcription and mitochondrial genome replication[38]. Using RT-QPCR, it was found that TFAM gene expression was increased in human primary dermal fibroblasts exposed to *Gluconacetobacter* spp compared to mock-treated cells (FIG. 4H). Since TFAM induces the mitochondrial DNA replication, QPCR for mitochondrial DNA copy numbers (mtDNA) was conducted. It was found that the mtDNA copy numbers were increased in human primary dermal fibroblasts exposed to *Gluconacetobacter* spp compared to mock-treated cells (FIG. 4I). An increase in the PGC-1α and TFAM expression, and mtDNA copy number reveals an overall enhancement of mitochondrial activity.

References for Example 1

1. Zubovych, I. O., Straud, S. & Roth, M. G. Mitochondrial dysfunction confers resistance to multiple drugs in *Caenorhabditis elegans*. *Mol Biol Cell* 21, 956-969 (2010).
2. Kayser, E. B., Morgan, P. G. & Sedensky, M. M. GAS-1: a mitochondrial protein controls sensitivity to volatile anesthetics in the nematode *Caenorhabditis elegans*. *Anesthesiology* 90, 545-554 (1999).
3. Rauthan, M., Ranji, P., Abukar, R. & Pilon, M. A Mutation in *Caenorhabditis elegans* NDUF-7 Activates the Mitochondrial Stress Response and Prolongs Lifespan via ROS and CED-4. *G3 (Bethesda)* 5, 1639-1648 (2015).
4. Dingley, S. et al. Mitochondrial respiratory chain dysfunction variably increases oxidant stress in *Caenorhabditis elegans*. *Mitochondrion* 10, 125-136 (2010).
5. Dancy, B. M., Sedensky, M. M. & Morgan, P. G. Effects of the mitochondrial respiratory chain on longevity in *C. elegans*. *Exp. Gerontol.* 56, 245-255 (2014).
6. McCormack, S. et al. Pharmacologic targeting of sirtuin and PPAR signaling improves longevity and mitochondrial physiology in respiratory chain complex I mutant *Caenorhabditis elegans*. *Mitochondrion* 22, 45-59 (2015).
7. The Family Acetobacteraceae: *The Genera Acetobacter, Acidomonas, Asaia, Gluconacetobacter, Gluconobacter, and Kozakia*. (Springer-Verlag, 2011). doi:10.1007/SpringerReference_3770
8. Swings, J. & De Ley, J. in *The Prokaryotes* 771-778 (Springer Berlin Heidelberg, 1981). doi:10.1007/978-3-662-13187-9_64
9. Trček, J., Mahnič, A. & Rupnik, M. Diversity of the microbiota involved in wine and organic apple cider submerged vinegar production as revealed by DHPLC analysis and next-generation sequencing. *Int. J. Food Microbiol.* 223, 57-62 (2016).
10. Coton, M. et al. Unraveling microbial ecology of industrial-scale Kombucha fermentations by metabarcoding and culture-based methods. *FEMS Microbiol. Ecol.* 93, (2017).
11. Ishii, N. et al. A mutation in succinate dehydrogenase cytochrome b causes oxidative stress and ageing in nematodes. *Nature* 394, 694-697 (1998).
12. Feng, J., Bussière, F. & Hekimi, S. Mitochondrial electron transport is a key determinant of life span in *Caenorhabditis elegans*. *Dev. Cell* 1, 633-644 (2001).
13. Lagido, C., McLaggan, D. & Glover, L. A. A Screenable In Vivo Assay for Mitochondrial Modulators Using Transgenic Bioluminescent *Caenorhabditis elegans*. *J Vis Exp* e53083-e53083 (2015). doi:10.3791/53083
14. Haynes, C. M. & Ron, D. The mitochondrial UPR-protecting organelle protein homeostasis. *J. Cell. Sci.* (2010).
15. Pellegrino, M. W., Fiorese, C. J., Baker, B. M. & Haynes, C. M. Mitochondrial import efficiency of ATFS-1 regulates mitochondrial UPR activation. *Science* (2012).
16. Munkácsy, E. et al. DLK-1, SEK-3 and PMK-3 Are Required for the Life Extension Induced by Mitochondrial Bioenergetic Disruption in *C. elegans*. *PLoS Genet* 12, e1006133 (2016).
17. Erkut, C., Gade, V. R., Laxman, S. & Kurzchalia, T. V. The glyoxylate shunt is essential for desiccation tolerance in *C. elegans* and budding yeast. *Elife* 5, 12897 (2016).
18. Amrit, F. R. G. et al. DAF-16 and TCER-1 Facilitate Adaptation to Germline Loss by Restoring Lipid Homeostasis and Repressing Reproductive Physiology in *C. elegans*. *PLoS Genet* 12, e1005788 (2016).
19. Ratnappan, R. et al. Germline signals deploy NHR-49 to modulate fatty-acid β-oxidation and desaturation in somatic tissues of *C. elegans*. *PLoS Genet* 10, e1004829 (2014).
20. Van Gilst, M. R., Hadjivassiliou, H., Jolly, A. & Yamamoto, K. R. Nuclear hormone receptor NHR-49 controls fat consumption and fatty acid composition in *C. elegans*. *PLoS Biol* 3, e53 (2005).
21. Lee, K., Goh, G. Y. S., Wong, M. A., Klassen, T. L. & Taubert, S. Gain-of-Function Alleles in *Caenorhabditis elegans* Nuclear Hormone Receptor nhr-49 Are Functionally Distinct. *PLoS ONE* 11, e0162708 (2016).
22. Sapir, A. et al. Controlled sumoylation of the mevalonate pathway enzyme HMGS-1 regulates metabolism during aging. *Proc Natl Acad Sci USA* 111, E3880-9 (2014).
23. Tondera, D. et al. SLP-2 is required for stress-induced mitochondrial hyperfusion. *EMBO J* 28, 1589-1600 (2009).
24. Babbar, M. & Sheikh, M. S. Metabolic Stress and Disorders Related to Alterations in Mitochondrial Fission or Fusion. *Mol Cell Pharmacol* 5, 109-133 (2013).

25. Rolland, S. G., Lu, Y., David, C. N. & Conradt, B. The BCL-2-like protein CED-9 of *C. elegans* promotes FZO-1/Mfn1,2- and EAT-3/Opa1-dependent mitochondrial fusion. *J. Cell Biol.* 186, 525-540 (2009).
26. Zhang, S. O. et al. Genetic and dietary regulation of lipid droplet expansion in *Caenorhabditis elegans*. *Proc Natl Acad Sci USA* 107, 4640-4645 (2010).
27. Back, P. et al. Exploring real-time in vivo redox biology of developing and aging *Caenorhabditis elegans*. *Free Radic. Biol. Med.* 52, 850-859 (2012).
28. Haigis, M. C. & Yankner, B. A. The aging stress response. *Mol. Cell* 40, 333-344 (2010).
29. Balaban, R. S., Nemoto, S. & Finkel, T. Mitochondria, oxidants, and aging. *Cell* 120, 483-495 (2005).
30. Brys, K., Castelein, N., Matthijssens, F., Vanfleteren, J. R. & Braeckman, B. P. Disruption of insulin signalling preserves bioenergetic competence of mitochondria in ageing *Caenorhabditis elegans*. *BMC Biol.* 8, 91 (2010).
31. Gruber, J. et al. Mitochondrial changes in ageing *Caenorhabditis elegans*—what do we learn from superoxide dismutase knockouts? *PLoS ONE* 6, e19444 (2011).
32. Matsushita, K., Toyama, H. & Adachi, O. Respiratory chains and bioenergetics of acetic acid bacteria. *Adv. Microb. Physiol.* 36, 247-301 (1994).
33. Saichana, N., Matsushita, K., Adachi, O., Frébort, I. & Frebortova, J. Acetic acid bacteria: A group of bacteria with versatile biotechnological applications. *Biotechnol. Adv.* 33, 1260-1271 (2015).
34. Peters, B. et al. Characterization of membrane-bound dehydrogenases from *Gluconobacter oxydans* 621H via whole-cell activity assays using multideletion strains. *Appl. Microbiol. Biotechnol.* 97, 6397-6412 (2013).
35. Lin, J., Handschin, C. & Spiegelman, B. M. Metabolic control through the PGC-1 family of transcription coactivators. *Cell Metab.* 1, 361-370 (2005).
36. Scarpulla, R. C. Metabolic control of mitochondrial biogenesis through the PGC-1 family regulatory network. *Biochim. Biophys. Acta* 1813, 1269-1278 (2011).
37. Goffart, S. & Wiesner, R. J. Regulation and Co-Ordination of Nuclear Gene Expression During Mitochondrial Biogenesis. *Experimental Physiology* 88, 33-40 (2004).
38. Jornayvaz, F. R. & Shulman, G. I. Regulation of mitochondrial biogenesis. *Essays Biochem.* 47, 69-84 (2010).

Example 2: Materials and Methods

*Caenorhabditis elegans* strains were maintained on NGM plates and OP50 *Escherichia coli* bacteria at 20° C. as described[1]. The wild-type strain was N2 Bristol. The strains used are described in Table 3.

TABLE 3

| Strain Name | Description |
| --- | --- |
| SAL150 | denEx28 [F10A3.4::GFP + pha-1(+)] |
| SAL146 | denEx24 [clec-85p::GFP + pha-1(+)] |
| SAL144 | denEx22 [K08D8.5::GFP + pha-1(+)] |
| SAL143 | denEx21 [F55G11.7::GFP + pha-1(+)] |
| SAL139 | denEx17 [dod-22::GFP + pha-1(+)] |
| SAL129 | denEx14 [lys-1::GFP + pha-1(+)] |
| SAL117 | denEx11 [spp-7::GFP + pha-1(+)] |
| SAL109 | denEx6 [abf-3::GFP + pha-1(+)] |
| SAL107 | denEx4 [abf-1::GFP + pha-1(+)] |
| SAL105 | denEx2 [lys-7::GFP + pha-1(+)] |
| AY101 | acIs101 [F35E12.5p::GFP + rol-6(su1006)] |
| SAL148 | denEx26 [F08G5.6::GFP + pha-1(+)] |
| BC14852 | sEx14852[rCesF15B9.1::GFP + pCeh36] |
| DM7065 | raEx65 [C53B4.3::GFP + pha-1(+) + rol-6]. |

TABLE 3-continued

| Strain Name | Description |
| --- | --- |
| BC15698 | sEx15698 [rCes K02G10.3::GFP + pCeh36] |
| BC11949 | sEx11949 [rCes C01H6.4::GFP + pCeh36] |
| BC16086 | sEx16086 [rCes F08F8.3a::GFP + pCeh36] |
| CF2222 | muEx336 [mtl-1::RFP + rol-6(su1006)] |
| BC15536 | sEx15536 [rCes T19B10.1::GFP + pCeh36] |
| BC14979 | sEx14979 [rCesF57B10.9::GFP + pCeh36]. |
| SD1631 | ccIs4251 [(pSAK2) myo-3p::GFP::LacZ::NLS + (pSAK4) myo-3p::mitochondrial GFP + dpy-20(+)] I. stIs10656 [nhr-69p::HIS-24::mCherry + unc-119(+)]. |
| VS11 | hjIs73 [vha-6p::GFP::daf-22 + C. briggsae unc-119(+)]. |
| RW11514 | stIs11514 [nhr-64::H1-wCherry + unc-119(+)]. |
| BC14632 | sEx14632 [rCes F59F4.1::GFP + pCeh361] |
| BC14386 | sEx14386 [rCes T14D7.1::GFP + pCeh361]. |
| BC11106 | sEx11106 [rCes Y50D7A.7::GFP + pCeh361]. |
| BC11207 | sIs10648 [rCes Y45F3A.3::GFP + pCeh36]. |
| VL714 | wwEx53 [acdh-2p::GFP]. |
| VL717 | wwEx54 [acdh-1p::GFP]. |
| BC11314 | sEx11314 [rCesT20G5.2::GFP + pCeh36] |
| AGD418 | uthIs205 [crtc-1p::crtc-1::RFP::unc-54 3'UTR + rol-6(su1006)] |
| BC10214 | sEx10214 [rCes ZK1248.14::GFP + pCeh36] |
| XA6900 | qaEx6900 [ftn-1p::pes-10::GFP-his + pha-1(+)]. |
| XA6901 | qaEx6901 [ftn-2p::pes-10::GFP::his + lin-15(+)]. |
| BC10060 | sEx884 [rCesC12C8.1::GFP + pCeh36] |
| BC14666 | sEx14666 [rCesF54F3.3::GFP + pCeh36] |
| PP563 | unc-119(ed4)III; hhIs64 [unc-119(+); sur-5::UbV-GFP]III |
| DA2123 | adIs2122 [lgg-1p::GFP::lgg-1 + rol-6(su1006)] icl-1::gfp |
| BC10434 | sEx10434 [rCes Y46G5A.17::GFP + pCeh361] |
| BC14873 | sEx14873 [rCes F39G3.7::GFP + pCeh361]. |
| BC12611 | sIs11096 [rCes T25G12.5::GFP + pCeh361] |
| BC15507 | sEx15507 [rCesT08B2.7b::GFP + pCeh361] |
| BC14661 | sEx14661[rCes F08A8.2::GFP + pCeh361]. |
| BC11281 | sEx11281 [rCes R07H5.2::GFP + pCeh361] |
| BC14848 | sEx14848 [rCesC47B2.8::GFP + pCeh361] |
| BC12923 | sIs12801 [rCes B0303.3::GFP + pCeh361] |
| BC14789 | sEx14789 [rCes Y38F1A.6::GFP + pCeh361] tbb-6::gfp |
| BC15777 | sEx15777 [rCesF10D2.9::GFP + pCeh361] |
| GR2183 | mgIs72 [rpt-3p::GFP + dpy-5(+)] II. |
| RW10592 | zuIs178 [his-72(1kb 5' UTR)::his-72::SRPVAT::GFP::his-72 (1KB 3' UTR) + 5.7 kb XbaI - HindIII unc-119(+)]. stIs10024 [pie-1::H2B::GFP::pie-1 3' UTR + unc-119(+)]. stIs10520 [nhr-57::H1-wCherry + unc-119(+)]. |
| CL2070 | dvIs70 [hsp-16.2p::GFP + rol-6(su1006)]. |
| AU133 | agIs17 [myo-2p::mCherry + irg-1p::GFP] IV. clec-60::gfp |
| IG274 | frIs7 [nlp-29p::GFP + col-12p::DsRed] IV. |
| SJ4100 | zcIs13[hsp-6::GFP]. |
| SJ4005 | zcIs4 [hsp-4::GFP] V |
| SJ4058 | zcIs9 [hsp-60::GFP + lin-15(+)]. |
| LDH71 | ldIs3 [gcs-1p::GFP + rol-6(su1006)]. |
| CL2166 | dvIs19 [(pAF15)gst-4p::GFP::NLS] III. |
| CF1553 | muIs84 [(pAD76) sod-3p::GFP + rol-6(su1006)]. |
| JG1 | ajIs1(pgp-5::gfp) |
| BC15680 | sEx15680 [rCesC47A10.1::GFP + pCeh361] |
| SD1448 | gaIs240 [ugt-22p::his-24::mCherry + unc-119(+)] |
| SD1444 | gaIs237 [cyp-25A2p::his-24::mCherry + unc-119(+)]. |
| BC10034 | sEx868 [rCesT21E8.1::GFP + pCeh361] |
| BC13865 | sEx13865 [rCesY17G9B.3::GFP + pCeh361]. |
| BC14956 | sEx14956 [rCesF42E11.1::GFP + pCeh361] |
| JG4 | cyp-13A7::GFP |
| BC15565 | sEx15565 [rCesH23N18.3::GFP + pCeh361] |
| BC14926 | sEx14926 [rCesK09A11.4::GFP + pCeh361] |
| BC13846 | sEx13846 [rCesB0213.15::GFP + pCeh361] |
| BC14562 | sEx14562[rCesTHF9.11::GFP + pCeh361] |
| BC15044 | sEx15044 [rCes F01D5.9::GFP + pCeh361] |
| BC10338 | sIs10109 [rCesY32H12A.3::GFP + pCeh361] |
| BC10672 | sIs10263[rCesF35H8.6::GFP + pCeh361]. |
| BC10366 | sEx10366 [rCes T02D1.5::GFP + pCeh361] |
| BC10058 | sEx10058 [rCes C56E6.5::GFP + pCeh36[ |
| BC12028 | sEx12028 [rCesF57C12.4::GFP + pCeh361] |
| BC10257 | sEx10257 [rCesZK455.7::GFP + pCeh361] |
| BC11571 | sEx11571 contains [rCes F39G3.1::GFP + pCeh36] |
| BC10027 | sEx861 [rCes Y50E8A.16::GFP + pCeh361]. |
| CY573 | bvIs5 [cyp-35B1p::GFP + gcy-7p::GFP] |
| STE68 | nhr-49(nr2041) I |
| WBM409 | nhr-49(nr2041) I; wbmEx149[ges-1p::3xHA::nhr- |

TABLE 3-continued

| Strain Name | Description |
|---|---|
| | 49(cDNA)::unc-54 3'UTR + myo-3p::mCherry::unc-54 3'UTR]. |
| MH5239 | prx-5(ku517) II |
| CF2167 | tcer-1(tm1452) II |
| CF2031 | muEx306 [tcer-1::GFP + odr-1::RFP] |
| DA2249 | spg-7(ad2249) I |
| QC134 | nduf-7(et19) I |
| CW152 | gas-1(fc21) X |
| TK22 | mev-1(kn1) III |
| MQ887 | isp-1(qm150) IV |
| PE254 | fels4 [sur-5p::luciferase::GFP + rol-6(su1006)] V |
| PS6187 | pha-1(e2123) unc-119(ed4) III;syEx1155 [myo-3p::tomm-20::mRFP::3xMyc + Cbr-unc-119(+)] |
| VS11 | hjIs73 [vha-6p::GFP::daf-22 + C. briggsae unc-119(+)] |
| VS8 | dhs-28(hj8) X |
| VS17 | hjIs9 [ges-1p::glo-1::GFP + unc-119(+)] |
| VS25 | hjIs14 [vha-6p::GFP::C34B2.10(SP12) + unc-119(+)] |
| JV1 | unc-119(ed3) III;jrIs1 [rpl-17p::HyPer + unc-119(+)]. |
| JV2 | unc-119(ed3) III;jrIs2 [rpl-17p::Grx1-roGFP2 + unc-119(+)] |

E. coli OP50, Gluconobacter oxydans DSM 2343 (621H) and its mutant derivatives were cultivated in a medium containing LB medium containing 1% glucose. The cultures were centrifuged and seeded onto NGM media without any antibiotics.

Gluconacetobacter strains were routinely grown in standard Hestrin-Schramm agar (D-glucose 20 g/L, yeast extract 5 g/L, peptone 5 g/L, disodium phosphate 2.7 g/L, citric acid 1.15 g/L, and agar 15 g/L) and incubated for 4 days at 30° C. For liquid culture, agar in the media was omitted. E. coli OP50 was also grown in the same media at 30° C. The liquid cultures were spotted onto NGM media plates without any antibiotics and left to grow at room temperature for at least 3 days.

Screening for Transcription Factors Responsible for Induction of Metabolic Genes in Response to Gluconoacetobacter spp To identify the transcription factor(s) that mediate the induction of metabolic genes in response to Gluconacetobacter feeding, the inventors conducted a cherry-picked RNAi screen of genes that were previously implicated in metabolism[2-13].

Feeding RNAi clones corresponding to dsRNA-control, daf-16, pha-4, hlh-30, skn-1, hsf-1, daf-12, nhr-80, nhr-49, tcer-1, sbp-1, nhr-69, and nhr-64 were grown in LB media with 25 µg/ml carbenicillin overnight and seeded onto RNAi agar plates containing 1 mM IPTG. The plates were dried in a laminar flow hood and incubated at room temperature overnight to induce dsRNA expression. 200 synchronized L1 larvae each of pmp-4::gfp, cpt-2::gfp, ech-1.2::gfp, acox-1.2::gfp, acdh-7::gfp, and prx-6::gfp expressing animals were placed onto each of the RNAi-containing agar plates, allowed to develop at 20° C. for 4 days. When the animals reached adult-stage, the worms were bleach-prepped. 20 synchronized L1 larvae were then placed on Gluconacetobacter seeded plates and scored for failure to induce GFP expression. dsRNA-control RNAi treated worms fed on Gluconacetobacter-seeded plates were used as controls.

Screening for Microbes that Suppress the Slow Developmental Growth Rate Phenotype of Spg-7(ad2249) Mutants ~200 Microbial strains were grown individually and seeded onto NGM media plates. ~20 Synchronized L1-stage spg-7(ad2249) mutant animals were placed on the 24-well plates and visually screened at 60 hours for the wells that contained animals that were fast growing compared to the worms fed on E. coli OP50. 6 microbial strains were recovered in the screen.

Isolation of G. oxydans Tn5 Transposon Mutants

Tn5 transposon mutagenesis in G. oxydans was performed using vector pME9978 obtained from Prof. Stephan Heeb, University of Nottingham, UK. pME9978 was transformed into E. coli S17-1 and selected on gentamicin and ampicillin LB media plates. pME9978 present in E. coli S17-1 cells were transferred into G. oxydans through conjugation. Conjugation was performed by mixing E. coli S17-1 bearing pME9978 and G. oxydans in suspension, plating them on LB medium, and incubating at 30° C. for 4 hours. The culture was scrapped from the LB plate and resuspended in 10 ml of M9 buffer. The resultant cell suspension was serially diluted up to $10^{-6}$ and plated out on the selection media plates (LB media containing 1% glucose, 10 µg/ml-1 gentamicin, and 50 µml-1 cefoxitin). G. oxydans is naturally resistant cefoxitin while E. coli S17-1 is sensitive. Gentamicin-resistant G. oxydans colonies appeared after 4 days of incubation at 30° C. ~2000 of these colonies were picked onto 96-well blocks filled with liquid selection media (LB media containing 1% glucose, 10 µg/ml-1 gentamicin, and 50 µg ml$^{-1}$ cefoxitin), grown at 30° C. for 2 days and stored at −80° C.

Screening for G. oxydans Mutants that Failed to Suppress the Slow Developmental Growth Rate Phenotype of Spg-7 (ad2249) Mutants G. oxydans Tn5 mutants were grown in LB liquid media containing 1% glucose, 10 µg/ml$^{-1}$ gentamicin, and 50 µg ml$^{-1}$ cefoxitin and spotted onto 24-well NGM media plates. ~20 Synchronized L1-stage spg-7(ad2249) mutant animals were placed on the 24-well plates and visually screened at 60 hours for the wells that contained animals that were slow-growing compared to the worms fed on wildtype G. oxydans. 11 mutants were recovered in the screen.

Identification of Transposon Insertion Sites in the G. oxydans Tn5 Mutants

The transposon mutant bacteria were grown in 100 ml of LB liquid media containing 1% glucose, 10 µg/ml-1 gentamicin, and 50 µg ml-1 cefoxitin and centrifuged at 2500 g for 15 minutes. Genomic DNA isolation was performed using a commercial genomic DNA isolation kit (Qiagen). The isolated genomic DNA was subjected to restriction digestion using NcoI (does not cut pME9978 plasmid) and heat-inactivated. The restriction fragments were self-ligated with T4 DNA ligase and electroporated into pir E. coli strain and selected on gentamicin containing LB media plates at 37° C. overnight. Since the transposon contains R6Kγori origin of replication, it can grow as independent plasmid in the pir E. coli strain. Multiple colonies from the gentamicin plates were pooled together and grown in gentamicin containing LB media plates at 37° C. overnight. The cultures were centrifuged and plasmid isolation was performed. The plasmid was sequenced to find the transposon insertion site using the following primers:

tpnRL17 (SEQ ID NO: 11): 5'-AACAAGCCAGG-GATGTAACG-3' tpnRL13 (SEQ ID NO: 12): 5'-CAGCAACACCTTCTT-CACGA-3'

Transposon Insertion Site in the Mutants

Glucose dehydrogenase_G7 (SEQ ID NO: 13 and SEQ ID NO: 34, respectively, in order of appearance):

```
CAGCTGACGCTTCGTCCGAAGAACCCGCTCTCCGATGCCGATATCTGGG
GTGGCACAATC...Tn5...GGCACAATCTTCGACCAGATGTTCTGCAG
CATCTACTTCCACTCCCTGCGCTACGAAGGT
```

Glucose dehydrogenase_G9 (SEQ ID NO: 14 and SEQ ID NO: 35, respectively, in order of appearance):

```
CTACATCCCGACCAAGACGGGCGATATCTTTGTCCTCGACCGCCGTACG
GGCAAGGAAG....Tn5...GGGCAAGGAAGTCGTCGCTGCTCCTGAAA
CACCAGTTCCAGGTGGTGCAGCTCCGGGCGA
```

Cytochrome O Ubiquinol oxidase subunit_G1 (SEQ ID NO: 15 and SEQ ID NO: 36, respectively, in order of appearance):

```
AGCACCCACGCCTACGACCCGTACCGCCCCCTTCAGACGGCTGACAACG
TCAAGCCCTG...Tn5...GACAGCGTCAAGCCACTGAATGTTCAGGTG
GTCTCTCTCGACTGGAAATGGCTGTTCATC
```

Glucose dehydrogenase_G6 (SEQ ID NO: 16 and SEQ ID NO: 37, respectively, in order of appearance):

```
CGCACCAACAAGGTGGTCTGGCAGCATCGTAACGGTACGCTCCGTGACT
CCATGCACGGC...Tn5...ATGCACGGCAGCTCCCTGCCCATCCCGCT
GCCTCCGATCAAGATCGGTGTTCCGAGCCTT
``` tonB_G2 (SEQ ID NO: 17 and SEQ ID NO: 38, respectively, in order of appearance):

```
TACAAGTGGTATCGATTGGGATTTTGATTATCGGATCCGTCTGACTAGC
ATGGATTCCAT...Tn5...GGATTCCATCACTGTCAGCAATAACCTGC
AGAACCTGGTCAATTTTTCCCAGCAGCAGAC
```

Ubiquinol-cytochrome C reductase iron-sulfur subunit_G3 (SEQ ID NO: 18 and SEQ ID NO: 39, respectively, in order of appearance):

```
CATCGGCGTCATGATCGGGATCTGCACGCATCTGGGC...Tn5...TGC
GTGCCGACTTTCGACGCCCCGACGCAGGCAGAACCTGCCGGGAA
```

Glucose dehydrogenase_G14 (SEQ ID NO: 19 and SEQ ID NO: 40, respectively, in order of appearance):

```
CGATGCAGAAACCGGGCAGAAGTGTTCCGGCTTTGGCAACGACGGCGAA
CTGGAACCTG...Tn5....GAACTGGAACTGCGCGAGCCGAACCAGCC
TTACGTCACGCCAGGCATGTATGAGCCGACG
```

Glucose dehydrogenase_promoter_G15 (SEQ ID NO: 20 and SEQ ID NO: 41, respectively, in order of appearance):

```
TCTTAATGCGCTTCTATGTGTTTGTCCGAAGGTCAAGTGC...Tn5...
AGGTCAAGTGCTGCACCAAATAACAGCTCTAGGAACATCATGAGCACAT
CTTCCCGGC
``` tonB_G11 (SEQ ID NO: 21 and SEQ ID NO: 42, respectively, in order of appearance):

```
GCAGTAATTTCGTGTCTGCTTCCTCCAGTCAGGTTCCGACCCTGTTT...
Tn5...GGTGGTAATACAAAGCTGCGTCCAGAAGCAGGGCGTACCTACAC
CTTTGGT
```

Glucose dehydrogenase_G13 (SEQ ID NO: 22 and SEQ ID NO: 43, respectively, in order of appearance):

```
TGGCGATCGCTGGTCTCCGCTGAAGCAGATCAATTCGACCAATGTTCAG
AACCTCAAGGT...Tn5...CCTCAAGGTGGCATGGCACATCCACACCA
AGGATCTGATGGGACCGAATGATCCGGGCGA
```

Carbon-Nitrogen Hydrolase_G5 (SEQ ID NO: 23 and SEQ ID NO: 44, respectively, in order of appearance):

```
AGACTCAATAGCGCGAGCACGGACAAGAATGTCCCAGTGAGCTTCACCC
GTTTGCTGCGT...Tn5...AAACGCTGCGGGCAGAACAATCATCTCAA
CATCCGCAGCCCGAAG
```

Isolation of Acetobacteraceae from Fruits

Members of the Acetobacteraceae family are characterized by acid production resulting in clearing of $CaCO_3$ and formation of halo around the colonies on calcium carbonate-containing media[2]. Samples of rotting apples, grapes, and oranges were crushed aseptically and mixed with 9 ml of M9 buffer and serially diluted up to $10^{-6}$ dilution. 100 µl of dilutions were spread on $CaCO_3$ medium (8% Glucose, 0.5% Yeast extract, 0.2% Mannitol, 0.05% Magnesium Sulphate, 10% Calcium carbonate, 100 µg/ml Cycloheximide, 10 µg/ml Nystatin).

Plates were incubated under aerobic conditions at 30° C. for 3-4 days. Colonies showing a clear halo were selected. Colony PCRs were conducted using the following primers: 27F (SEQ ID NO: 24): AGAGTTTGATCMTGGCTCAG 1492R (SEQ ID NO: 25): TACGGYACCTTGTTACGACTT The conditions used for touchdown colony PCR were as follows: 95° C. for 10 minutes followed by 15 cycles of 30 s at 95° C., 30 s at 65° C. (step down of –1° C. for every cycle) and 1 minute at 72° C. This was followed by 40 cycles of 30 s at 95° C., 30 s at 50° C. and 1:30 minutes at 72° C.

16S rRNA sequencing on the isolates were conducted for identification of the isolates.

Microscopy

For high-magnification differential interference contrast and fluorescence images, worms treated with appropriate conditions were mounted onto agar pads and images were acquired using a Zeiss AXIO™ Imager Z1 microscope fitted with a Zeiss AxioCam™ HRc camera and Axiovision™ software. Fluorescent images were converted to 16-bit images, thresholded and quantified using ImageJ. Student's t test was used determine statistical significance. GraphPad™ Prism 8.0 was used for these calculations and generating graphs. Low-magnification bright-field images were acquired using a Zeiss AxioZoom™ V16 Microscope, equipped with a Hammamatsu Orca™ flash 4.0 digital camera, and using Axiovision™ software. Immunofluorescence images (shown in FIG. 2) were acquired with an IX-70 microscope (Olympus, Waltham, Mass.) fitted with a cooled CCD camera (CH350; Roper Scientific) driven by the Delta Vision system (Applied Precision, Pittsburgh, Pa.). Images were deconvolved using the SoftWoRx 3.3.6 software (Applied Precision).

Measuring Endogenous Hydrogen Peroxide Levels Using HyPer Strain

To measure endogenous hydrogen peroxide levels, transgenic jrIs1 [Prp1-17::HyPer] worms expressing a HyPer as described 3 was used. Synchronized L1-stage transgenic jrIs1[Prp1-17::HyPer] animals were grown in E. coli OP50 and G. hansenii and about 1000 L4-stage worms were harvested in 96 microtiter well plates. For $H_2O_2$ treatment experiment, $H_2O_2$ was added to the worms in the 96-well itself and measurements were taken within 15 minutes. An excitation wavelength of either 490 nm or 405 nm was used to measure oxidized or reduced HyPer™ probe fluorescence respectively with an emission filter of 535 nm. The absorbance at 620 nm was used to normalize for worm numbers. The statistical significance of differences between conditions was determined by using unpaired t-test. GraphPad™ Prism 8.0 was used for these calculations.

Measuring Endogenous GSSG/2GSH Ratios

To measure in vivo GSSG/2GSH ratios, transgenic jrIs2 [Prp1-17::Grx1-roGFP2] worms expressing a Grx1-roGFP2 as described[3] were used. Synchronized L1-stage transgenic jrIs2[Prp1-17::Grx1-roGFP2] animals were grown in E. coli OP50 and G. hansenii and about 1000 L4-stage worms were harvested in 96 microtiter well plates after washing at least six times in M9 buffer. For $H_2O_2$ treatment experiment, $H_2O_2$ was added to the worms in the 96-well itself and measurements were taken within 15 minutes. An excitation wavelength of either 490 nm or 405 nm was used to measure reduced or oxidized Grx1-roGFP2 probe fluorescence respectively with an emission filter of 535 nm. The absorbance at 620 nm was used to normalize for worm numbers. The statistical significance of differences between conditions was determined by using unpaired t-test. GraphPad™ Prism 8.0 was used for these calculations.

Measuring Endogenous Hydrogen Peroxide Levels Using Amplex™ Red Assay

Measuring endogenous hydrogen peroxide levels using Amplex™ Red assay was performed as described[4].

To measure ROS production, synchronized L1-stage wildtype worms were grown in E. coli OP50 and G. hansenii and about 1000 L4-stage worms were harvested in 96 microtiter well plates after washing at least six times in M9 buffer, followed by 3 washes with the reaction buffer supplied with the Amplex™ Red Hydrogen Peroxide/Peroxidase assay kit. Equal volume of the Amplex™ Red reaction buffer was then added to the wells, the absorbance at 540 nm was read after 3 hours with a plate reader (SpectraMax™ plate reader). For $H_2O_2$ treatment experiment, $H_2O_2$ was added to the worms in the 96-well itself and measurements were taken after 2 hours. The absorbance at 620 nm was used to normalize for worm numbers. All the values were normalized to the values of control untreated worms. The statistical significance of differences between conditions was determined by using unpaired t-test. GraphPad™ Prism 8.0 was used for these calculations.

Human mtDNA Copy Number Estimation

Human dermal primary Fibroblasts (Coriell GM25438) were grown in 6-well plates with EMEM containing 10% Fetal Bovine Serum, 1% MEM non-essential amino acids, and 1% Penicillin-Streptomycin until the cells were ~90% confluent in a 37° C., 5% $CO_2$ humidified incubator. The cells were treated with Mock-treatment or $10^6$ CFU of G. hansenii-treatment for 24 hours and the genomic DNA was isolated using a commercial DNA isolation kit (Qiagen). The quantity and purity of the isolated DNA was assayed using a Nanodrop™ 2000 spectrophotometer (Thermo Scientific, Wilmington, Del., USA) and the samples were stored at −70° C. until use. The relative mtDNA copy number was measured by qPCR as described[5]. The values were normalized to that of a single copy nuclear DNA gene as described. The primer sequences used were:

L394 (SEQ ID NO: 26): 5'-CACCAGCCTAACCAGAT-TTC-3'

H475 (SEQ ID NO: 27): 5'-GGGTTGTATTGATGAGATT-AGT-3'

HBG1F (SEQ ID NO: 28): 5'-GCTTCTGACACAACTGTGTTCACTAGC-3'

HBG1R (SEQ ID NO: 29): 5'-CACCAACTTCATC-CACGTTCACC-3'

L394/H475 were for the mtDNA content, and HBG1F/R primers were for nuclear β-globin gene[5]. qPCR was performed with an iCycler™ machine (Bio-Rad) using iQ SYBR Master Mix (Bio-Rad) and the assays were performed under the following conditions: denaturation at 95° C. for 10 minutes followed by 40 cycles of 10 s at 95° C., 30 at 60° C. and 30 s at 72° C. All assays were carried out in triplicate using 10 ng DNA template per reaction. All reactions were performed in triplicate and on 3 biological replicates. The relative mtDNA copy number was calculated using the ΔCt method.

RNA Isolation and Quantitative RT-PCR Analysis of PGC-1 and TFAM

Human primary Fibroblasts were grown in 6-well plates with EMEM containing 10% Fetal Bovine Serum, 1% MEM non-essential amino acids, and 1% Penicillin-Streptomycin until the cells were ~90% confluent in a 37™ C, 5% $CO_2$ humidified incubator. The cells were treated with Mock-treated or $10^6$ CFU of G. hansenii-treated for 24 hours. After incubation for 24 h in each condition, total cellular RNA was isolated from cells using commercial RNA isolation kit (Qiagen). Total RNA was DNAase treated using the TURBO DNA-free kit (Applied Biosystems). cDNA was prepared using the First strand cDNA synthesis kit from Invitrogen. qRT-PCR assays were performed under the following conditions: denaturation at 95° C. for 10 minutes followed by 40 cycles of 10 s at 95° C., 30 at 55° C. and 30 s at 72° C. The primer sequence used[6,7]:

hTfamF (SEQ ID NO: 30): TGTTCACAATGGA-TAGGCAC hTfamF (SEQ ID NO: 31): TCTGGGTTTTC-CAAAGCAAG hPGC-1αF (SEQ ID NO: 32): TGAAGACGGATTGCCCT-CATT hPGC-1αR (SEQ ID NO: 33): GCTGGTGCCAGTAAGAGCTT All reactions were done in triplicate and on 3 biological replicates. All the values are normalized to the nuclear β-globin gene as internal control as well as to the transcript levels in mock-treated cells.

ATP Determination Assay

ATP determination was performed as described[8]. To measure ATP levels, synchronized L1-stage worms were grown in E. coli OP50 and G. hansenii and were harvested after washing at least six times in M9 buffer and approximately 1000 worms in 100 μl of M9 were frozen in liquid nitrogen and stored at −80° C. until analysis. The samples were placed immediately in boiling water bath for 15 min. After adding twice the amount of distilled water, centrifugation was done at 14,000 rpm for 5 min and supernatant was transferred into a second tube. Equal volume of luciferase reagent (Promega™) was added and luminescence was measured using a plate reader (SpectraMax™ Microplate reader). Protein content was measured using BCA method. ATP concentrations were normalized to protein content of samples. All the values were normalized to wildtype fed on E. coli OP50.

ATP Determination Assay Using the Luciferase Strain

ATP determination assay using the Luciferase strain was described[9]. To measure in vivo ATP production, synchronized L1-stage Psur-5::luc+::gfp worms were grown in E. coli OP50 and G. hansenii and about 1000 adult-stage worms/well were harvested in 96 microtiter well plates after washing at least six times in M9 buffer. 100 μM D-luciferin was added to the wells and the luminescence was measured within 5 min in a SpectraMax™ microplate reader. GFP fluorescence was quantified in SpectraMax™ microplate reader using 485 nm excitation and a 520 nm emission filter. Background measurements were subtracted from readings. Luminescence values were normalized to GFP fluorescence of samples. All the values were normalized to wildtype fed on *E. coli* OP50. For the RNAi experiments, synchronized L1-stage Psur-5::luc+::gfp worms were grown in *E. coli* HT115 strain carrying the corresponding the dsRNA until adulthood and egg-prepped. The L1-stage worms were then transferred to either *E. coli* OP50 or *G. hansenii*-seeded media plates. For the experiment using rotenone, paraquat, azide, and, antimycin, the worms grown on *E. coli* OP50 or *G. hansenii* were washed at least 6 times and transferred to *E. coli* OP50 plates containing the drugs. The *E. coli* OP50 plates with proper concentrations of drugs were made one day before use. All the assays were conducted on *E. coli* OP50 plates to avoid potential drug detoxification by *G. hansenii*.

Mitotracker CMXRos Staining

For the experiment using Mitotracker™ CMXRos, the worms grown on *E. coli* OP50 or *G. hansenii* were washed at least 6 times and transferred to *E. coli* OP50 plates containing the 10 µM of Mitotracker™ CMXRos. After 24 hours, worms were washed at least 6 times to remove the dye and dropped onto *E. coli* OP50 plates to clear off non-specific gut staining. After 2 hours, worms were washed at least 6 times and transferred to agar plates for imaging.

Tetramethylrhodamine Ethylester (TMRE) Staining

For the experiment using TMRE, the worms grown on *E. coli* OP50 or *G. hansenii* were washed at least 6 times and transferred to *E. coli* OP50 plates containing the 1 µM of TMRE. After 24 hours, worms were washed at least 6 times to remove the dye and dropped onto *E. coli* OP50 plates to clear off non-specific gut staining. After 2 hours, worms were washed at least 6 times and ~1000 worms were transferred to each well of 96-well plate and the fluorescence was quantified in SpectraMax™ microplate reader using 549 nm excitation and a 575 nm emission filter.

Optimization of Metabolite Production

It was discovered that when the bacteria are grown in either 0-5% yeast extract broth, the metabolites are not produced. Further, it was found that addition of glucose or other metabolizable monosaccharide sugars such as fructose or disaccharides such as sucrose to the 3% yeast extract medium is required for metabolite production. In addition, it was discovered that as little as 0.5% of such sugars is enough for optimal metabolite production. Thus, it is recommended that any medium used for metabolite production comprise at least 0.5-5% of a metabolizable sugar source.

Further experiments indicate that 3% corn steep liquor is sufficient for optimal metabolite production, thus 0.5-5% corn steep liquor is recommended for optimal production of metabolites. It is contemplated herein that when bacteria are grown on a commercial scale, 3% corn steep liquor may be the preferred method for fermentation.

References for Example 2

1. Brenner, S. The genetics of *Caenorhabditis elegans*. Genetics 77, 71-94 (1974).
2. The Family Acetobacteraceae: The Genera *Acetobacter, Acidomonas, Asaia, Gluconacetobacter, Gluconobacter*, and *Kozakia*. (Springer-Verlag, 2011). doi:10.1007/SpringerReference_3770
3. Back, P. et al. Exploring real-time in vivo redox biology of developing and aging *Caenorhabditis elegans*. Free Radic. Biol. Med. 52, 850-859 (2012).
4. Chávez, V., Mohri-Shiomi, A., Maadani, A., Vega, L. A. & Garsin, D. A. Oxidative stress enzymes are required for DAF-16-mediated immunity due to generation of reactive oxygen species by *Caenorhabditis elegans*. Genetics 176, 1567-1577 (2007).
5. Chen, S. et al. Elevated mitochondrial DNA copy number in peripheral blood cells is associated with childhood autism. BMC Psychiatry 15, 50 (2015).
6. Zaccagnino, P. et al. An active mitochondrial biogenesis occurs during dendritic cell differentiation. Int. J. Biochem. Cell Biol. 44, 1962-1969 (2012).
7. Oral, E. A. et al. Inhibition of IKKε and TBK1 Improves Glucose Control in a Subset of Patients with Type 2 Diabetes. Cell Metab. 26, 157-170.e7 (2017).
8. Palikaras, K. & Tavernarakis, N. Intracellular Assessment of ATP Levels in *Caenorhabditis elegans*. Bio Protoc 6, (2016).
9. Lagido, C., McLaggan, D. & Glover, L. A. A Screenable In Vivo Assay for Mitochondrial Modulators Using Transgenic Bioluminescent *Caenorhabditis elegans*. J Vis Exp e53083-e53083 (2015). doi:10.3791/53083

Example 3: Treatment of Parkinson's Disease

Parkinson's Disease (PD) is the most common motor-related disorder in middle or late life disease, affecting ~6.2 million people worldwide.[1] PD is characterized by accumulation of α-synuclein inclusions in the neurons and degeneration and/or loss of dopaminergic neurons. The cardinal clinical symptoms of PD includes slow movement, resting tremor, rigidity, and postural instability.[2] While a majority of PD cases are of unknown origin and sporadic, mutations in some genes have been associated with rare, familial forms of the disease. Several lines of evidence implicate defects in mitochondrial respiration in the etiology and pathogenesis of PD. First, MPTP, an inhibitor of complex I of the electron transport chain, can induce PD.[3,4] Inhibition of complex I results in decreased mitochondrial ATP production, increased production of mitochondria-derived Reactive Oxygen Species (ROS), and activation of mitochondria-dependent apoptotic pathways. Second, post mortem studies of PD patients found elevated levels of oxidative stress markers/products[5-7] in the dopaminergic neurons. Third, a reduction of mitochondrial complex I activity by 30% was observed in brain as well as peripheral tissues of PD patients.[8,9] Fourth, neurotoxins such as rotenone, paraquat, and 6-hydroxydopamine (6-OHDA) induce mitochondrial dysfunction resulting in PD-associated phenotypes in animal models.[10] Finally, PD-associated genes such as α-synuclein, LRRK2 (leucine-rich repeat kinase 2), parkin, PINK1, and DJ-1 affect mitochondrial dynamics, trafficking, autophagy, and quality control.[11,12]

All cells require mitochondria for their energy demands including neurons, which are critically dependent on proper mitochondrial function. Neurons have high metabolic activity and they depend heavily on mitochondria for their bioenergetic demand. Several factors make the neurons in general, and dopaminergic neurons in particular, susceptible to degeneration; these include ROS (which result from dopamine metabolism and mitochondrial dysfunction), low endogenous antioxidant levels, and high levels of iron and calcium (which are known to promote ROS formation).[13] Further, neuronal tissues contain high levels of polyunsaturated fatty acids, which are prone to lipid peroxidation and the generation of toxic products.[14] Regardless of whether a primary or secondary cause, mitochondrial dysfunction holds promise as a potential therapy target. Aging is the greatest risk factor for PD,[15] thus with increasing average life expectancy worldwide,[16] the number of people affected by PD will rise considerably in the near future. Thus, there is a significant clinical unmet need for new therapeutic approaches that not only can be used for slowing down PD, but also as preventive measures for the aging population.

Mitochondria are highly dynamic organelles required for cellular energy production, response to oxidative stress, and apoptosis. Thus, it is not surprising that mitochondrial dysfunction, characterized by a loss of efficiency in the electron transport chain and reduction in ATP synthesis, is a characteristic of aging, and aging-related neurodegenerative diseases.[17,18] Despite having distinct pathological and clinical features, several other neurodegenerative disorders including Alzheimer's disease, Huntington's disease, and amyotrophic lateral sclerosis are associated with mitochondrial dysfunction-derived oxidative stress[19] as well; this suggests a common mechanism that contributes to neuronal degeneration[20].

While most of the earlier studies on PD focus entirely on the brain pathologies, the gastrointestinal (GI) system is now recognized as an important source for PD pathogenesis.[21-23] GI symptoms, such as constipation, affects ~80% of PD-patients and idiopathic constipation is an important risk factor for PD.[24] In PD, constipation is associated with alpha-synuclein accumulation in the enteric nervous system,[25] gut inflammation, and increased gut permeability.[26] Further, the intestinal mucosal inflammation is thought to lead to synuclein accumulation in the enteric nerves, which can then spread in a prion-like fashion to the central nervous system via autonomic connections.[27-29] Many of the GI tract changes are observed even before the onset of neuronal symptoms;[30] thus, PD pathogenesis might act primarily via the GI tract[31,32].

C. elegans as a model is well-positioned to play an important role in PD-associated discoveries.[33] C. elegans contain well-defined dopaminergic (DA) neurons that are visible under fluorescence microscopy and have a range of locomotor activities.[34] All orthologs of genes linked to familial PD are present in C. elegans, except α-synuclein. Ectopic overexpression of α-synuclein produces neurotoxic effects, which can be blocked by neuroprotective genes. A number of worm models of PD have been generated through either exposing worms to neurotoxins such as MPP+ or 6-OHDA or by introducing the mutations or human genes implicated in inherited forms of PD.[35-41] These worm models exhibit PD-associated phenotypes including degeneration or loss of dopamine neurons, low dopamine levels, defects in dopamine-dependent behaviors, and movement defects.

Figure 10B:
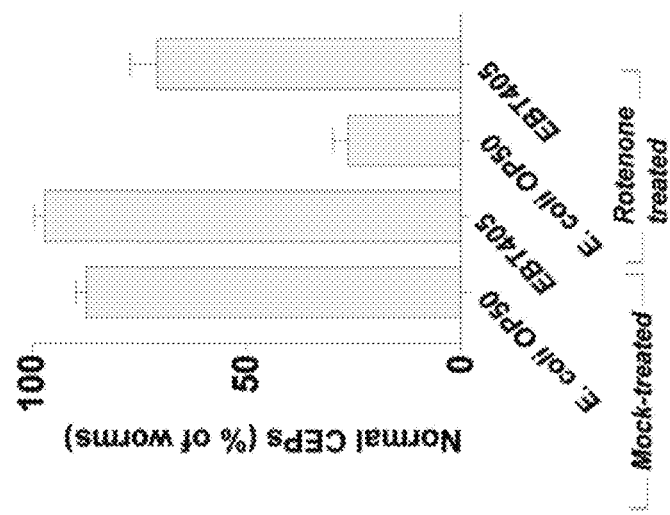
FIGS. 10A-10B.
Figure 10A:
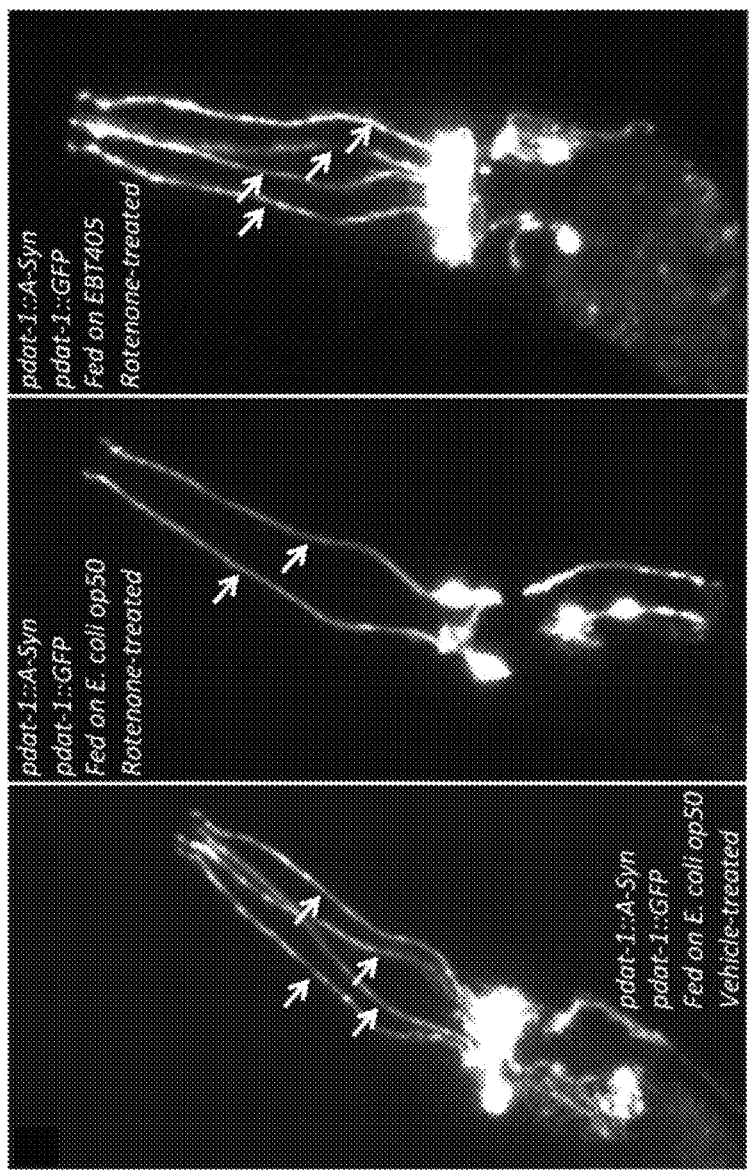

Overexpression of human alpha-synuclein under the control of a DA neuron-specific promoter results in age-dependent neurodegeneration.[42] Using this strain, over 30 strains of microbes were screened for prospective neuroprotective potential. Expression of human alpha-synuclein in the dopaminergic neurons induces complete degeneration and loss of the neurons by day 10 of adulthood. It was observed that when combined with 1 uM of Rotenone, the dopaminergic neuron loss is achieved more rapidly in 4 days. Rotenone is a broad-spectrum insecticide that has been demonstrated to induce PD-like symptoms in animal models accompanied by the selective destruction of DAergic neurons. In C. elegans, chronic exposure of rotenone caused dopaminergic neurodegeneration.[43] Rotenone acts by inhibiting mitochondrial respiratory complex I.[44] In the screen, the human alpha-synuclein animals were fed ad-libitum on a single strain of microbial lawn starting from the first larval stage and subjected to rotenone treatment at the fourth larval stage. After 60 hours of rotenone treatment, the animals were screened for survival of the anterior CEP (cephalic) dopaminergic neurons, which were visualized via co-expression of GFP driven in the dopaminergic neurons. While ~75% of the worms fed on the control E. coli op50 had lost the CEP neurons, worms fed on Gluconoacetobacter EBT405 decreased CEP neurodegeneration (FIGS. 10A-10B).

References for Example 3

1. GBD 2015 Disease and Injury Incidence and Prevalence Collaborators. Global, regional, and national incidence, prevalence, and years lived with disability for 310 diseases and injuries, 1990-2015: a systematic analysis for the Global Burden of Disease Study 2015. Lancet 388, 1545-1602 (2016).
2. Pires, A. O. et al. Old and New Challenges in Parkinson's Disease Therapeutics. Prog. Neurobiol. (2017). doi: 10.1016/j.pneurobio.2017.04.006
3. Nicklas, W. J., Vyas, I. & Heikkila, R. E. Inhibition of NADH-linked oxidation in brain mitochondria by 1-methyl-4-phenyl-pyridine, a metabolite of the neurotoxin, 1-methyl-4-phenyl-1,2,5,6-tetrahydropyridine. Life Sci. 36, 2503-2508 (1985).
4. Ramsay, R. R., Salach, J. I., Dadgar, J. & Singer, T. P. Inhibition of mitochondrial NADH dehydrogenase by pyridine derivatives and its possible relation to experimental and idiopathic parkinsonism. Biochem Biophys Res Commun 135, 269-275 (1986).
5. Yoritaka, A. et al. Immunohistochemical detection of 4-hydroxynonenal protein adducts in Parkinson disease. Proceedings of the National Academy of Sciences 93, 2696-2701 (1996).
6. Floor, E. & Wetzel, M. G. Increased Protein Oxidation in Human Substantia Nigra Pars Compacta in Comparison with Basal Ganglia and Prefrontal Cortex Measured with an Improved Dinitrophenylhydrazine Assay. J Neurochem 70, 268-275 (2002).
7. Zhang, J. et al. Parkinson's disease is associated with oxidative damage to cytoplasmic DNA and RNA in substantia nigra neurons. Am. J. Pathot 154, 1423-1429 (1999).
8. Schapira, A. H. V. et al. MITOCHONDRIAL COMPLEX I DEFICIENCY IN PARKINSON'S DISEASE. The Lancet 333, 1269 (1989).
9. Parker, W. D., Boyson, S. J. & Parks, J. K. Abnormalities of the electron transport chain in idiopathic Parkinson's disease. Ann. Neurol. 26, 719-723 (1989).
10. Tieu, K. A guide to neurotoxic animal models of Parkinson's disease. Cold Spring Harb Perspect Med 1, a009316-a009316 (2011).
11. Moore, D. J., West, A. B., Dawson, V. L. & Dawson, T. M. Molecular pathophysiology of Parkinson's disease. Annu. Rev. Neurosci. 28, 57-87 (2005).
12. Robinson, P. A. (2010). Understanding the molecular basis of Parkinson's disease, identification of biomarkers and routes to therapy. Expert Review of Proteomics, 7(4), 565-578.
13. Dias, V., Junn, E., & Mouradian, M. M. The role of oxidative stress in Parkinson's disease. Journal of Parkinson's Disease, 3(4), 461-491 (2013).
14. Liu, X., Yamada, N., Maruyama, W., & Osawa, T. Formation of dopamine adducts derived from brain polyunsaturated fatty acids: mechanism for Parkinson disease. *Journal of Biological Chemistry*, 283(50), 34887-34895 (2008).
15. Collier, T. J., Kanaan, N. M., & Kordower, J. H. Ageing as a primary risk factor for Parkinson's disease: evidence from studies of non-human primates. *Nature Reviews. Neuroscience*, 12(6), 359-366 (2011).
16. GBD 2013 Mortality and Causes of Death Collaborators, Lancet 385, 117 (2015).
17. Federico, A., Cardaioli, E., Da Pozzo, P., Formichi, P., Gallus, G. N. and Radi, E. Mitochondria, oxidative stress and neurodegeneration. *J. Neurol. Sci*, 322, 254-262 (2012).
18. Winklhofer, K. F., and Haass, C. Mitochondrial dysfunction in Parkinson's disease. Biochim. Biophys. Acta 1802, 29-44 (2010).
19. Albers, D. S., and Flint Beal, M. Mitochondrial dysfunction and oxidative stress in aging and neurodegenerative disease. In Advances in Dementia Research (pp. 133-154) (2000).
20. Andersen, J. K. Oxidative stress in neurodegeneration: cause or consequence? Nature Reviews. Neuroscience, 10(7), S18-S25. (2004).
21. Mukherjee, A., Biswas, A., & Das, S. K. Gut dysfunction in Parkinson's disease. World Journal of Gastroenterology, 22(25), 5742-5752 (2016).
22. Pellegrini, C., Colucci, R., Antonioli, L., Barocelli, E., Ballabeni, V., Bernardini, N., et al. Intestinal dysfunction in Parkinson's disease: Lessons learned from translational studies and experimental models. Neurogastroenterology & Motility, 28(12), 1781-1791 (2016).
23. Kuo, Y.-M., Li, Z., Jiao, Y. N., Gaborit, A. K. Pani, B. M. Orrison, B. G. Bruneau, B. I. Giasson, R. J. Smeyne, M. D. Gershon, and R. L. Nussbaum. Extensive enteric nervous system abnormalities in mice transgenic for artificial chromosomes containing Parkinson disease-associated α-synuclein gene mutations precede central nervous system changes. 19, 1633-1650 (2010).
24. Noyce, A. J., Bestwick, J. P., Silveira-Moriyama, L., Hawkes, C. H., Giovannoni, G., Lees, A. J and Schrag, A. Meta-analysis of early nonmotor features and risk factors for Parkinson disease. 72, 893-901 (2012).
25. Cersosimo, M. G and Benarroch, E. E. Pathological correlates of gastrointestinal dysfunction in Parkinson's disease. 46, 559-564 (2012).
26. Devos, D., Lebouvier, T., Lardeux, B. M., Biraud, Rouaud, T., Pouclet, H., E. Coron, Bruley des Varannes, S., Naveilhan, P., Nguyen, J.-M., Neunlist, M., and Derkinderen, P. Colonic inflammation in Parkinson's disease. 50, 42-48 (2013).
27. Braak, H., Rüb, U., Gai, W. P and Del Tredici, K. Idiopathic Parkinson's disease: possible routes by which vulnerable neuronal types may be subject to neuroinvasion by an unknown pathogen. 110, 517-536 (2003).
28. Hawkes, C. H., Del Tredici, K and Braak, H. Neuropathol. Parkinson's disease: a dual-hit hypothesis. 33, 599-614 (2007).
29. Hawkes, C. H., Del Tredici, K and Braak, H. Parkinson's disease: the dual hit theory revisited. 1170, 615-622 (2009).
30. Verbaan, D., Marinus, J., Visser, M., van Rooden, S. M., Stiggelbout, A. M., and van Hilten, J. J. Patient-reported autonomic symptoms in Parkinson disease. Neurology 69, 333-341 (2007).
31. Shannon, K. M., Keshavarzian, A., Dodiya, H. B., Jakate S., and Kordower, J. H. Is alpha-synuclein in the colon a biomarker for premotor Parkinson's disease? Evidence from 3 cases. Mov. Disord. 27, 716-719 (2012).
32. Kieburtz, K and Wunderle, K. B. Parkinson's disease: evidence for environmental risk factors. 28, 8-13 (2013).
33. Caldwell, G. A., & Caldwell, K. A. Traversing a wormhole to combat Parkinson's disease. Disease Models & Mechanisms, 1(1), 32-36 (2008).
34. Nass, R., Hall, D. H., Miller, D. M. & Blakely, R. D. Neurotoxin-induced degeneration of dopamine neurons in *Caenorhabditis elegans*. Proceedings of the National Academy of Sciences 99, 3264-3269 (2002).
35. Lakso, M. et al. Dopaminergic neuronal loss and motor deficits in *Caenorhabditis elegans* overexpressing human alpha-synuclein. *J Neurochem* 86, 165-172 (2003).
36. Ved, R. et al. Similar patterns of mitochondrial vulnerability and rescue induced by genetic modification of alpha-synuclein, parkin, and DJ-1 in *Caenorhabditis elegans*. *J Biol Chem* 280, 42655-42668 (2005).
37. van Ham, T. J. et al. *C. elegans* model identifies genetic modifiers of alpha-synuclein inclusion formation during aging. *PLoS Genet* 4, e1000027 (2008).
38. Caldwell, G. A. & Caldwell, K. A. Traversing a wormhole to combat Parkinson's disease. *Dis Model Mech* 1, 32-36 (2008).
39. Harrington, A. J., Hamamichi, S., Caldwell, G. A. & Caldwell, K. A. *C. elegans* as a model organism to investigate molecular pathways involved with Parkinson's disease. *Dev. Dyn.* 239, 1282-1295 (2010).
40. Braungart, E., Gerlach, M., Riederer, P., Baumeister, R. & Hoener, M. C. *Caenorhabditis elegans* MPP+ model of Parkinson's disease for high-throughput drug screenings *Neurodegener Dis* 1, 175-183 (2004).
41. Cao, S., Gelwix, C. C., Caldwell, K. A. & Caldwell, G. A. Torsin-mediated protection from cellular stress in the dopaminergic neurons of *Caenorhabditis elegans*. *J. Neurosci.* 25, 3801-3812 (2005).
42. Hamamichi, S. et al. Hypothesis-based RNAi screening identifies neuroprotective genes in a Parkinson's disease model. *Proc Natl Acad Sci USA* 105, 728-733 (2008)
43. Zhou, S., Wang, Z. & Klaunig, J. E. *Caenorhabditis elegans* neuron degeneration and mitochondrial suppression caused by selected environmental chemicals. *Int J Biochem Mol Biol* 4, 191-200 (2013).
44. Gao, H.-M., Liu, B. & Hong, J.-S. Critical role for microglial NADPH oxidase in rotenone-induced degeneration of dopaminergic neurons. *J. Neurosci.* 23, 6181-6187 (2003).

Example 4: Treatment of Alzheimer's Disease

AD is a fatal neurodegenerative disease characterized by progressive decline in memory and cognitive functions. Early-onset familial AD associated with the mutations in APP or γ-secretase gene accounts for less than 5% of the all cases while 95% of the sporadic or late-onset AD has unknown etiology[1]. The pathological hallmarks of AD are accumulation of extracellular senile plaques and intracellular neurofibrillary tangles (NFTs) in the AD patient's brain. The senile plaques consist of β-amyloid peptide (Aβ) as the primary component while NFTs consist of abnormal fibrillar forms of microtubule-associated protein tau as the primary component[2]. Aβ accumulation and NFTs are thought to indicate neuronal dysfunction and impending neuronal demise[2].

Mitochondrial dysfunction and defects in energy metabolism have been consistently observed in human AD patients[3,4]. Aβ and tau pathologies are strongly associated with mitochondrial dysfunction in AD. Aβ and tau directly affect mitochondrial function causing impairment of ATP production, increased reactive oxygen species (ROS) production, decreased oxygen consumption, and decreased mitochondrial complex I and IV function[5]. Mitochondrial dysfunction is found to be an early event in AD. In the case of sporadic AD, progressive increase in oxidative stress with advancing age is shown to cause Aβ deposition and NFTs formation[6]. This could lead to a continuous cycle of events where the Aβ and tau exacerbates mitochondrial dysfunction leading to rapidly progressive AD symptoms. Thus, therapeutic efforts aimed at restoring mitochondrial function or protecting mitochondria against Aβ-induced damage or replenishing the mitochondrial numbers and function in the aging population is a promising route for identifying AD therapeutics.

C. elegans as a model is well-positioned to play an important role in AD-associated discoveries. Ortholog of genes associated with the cause of AD are conserved in C. elegans including amyloid precursor protein (APP) and tau. A number of worm models of AD have been generated by introducing the mutations or human genes implicated in AD[7-9]. These worm models exhibit AD-associated phenotypes including amyloid deposits, increased oxidative stress and progressive paralysis[7-9]. Further, impairment of electron transport chain function and mitochondrial dysfunction were found in the C. elegans AD models[10,11], similar to those observed in AD patients. Further, these models have been used successfully in identifying neuroprotective compounds[9].

About one third of the drugs used in the clinic today were initially isolated from plants or microbes. Though chemical synthesis of compounds has taken over the pharmaceutical industry as the source for identifying novel therapeutics, bioprospecting natural sources like plants and microbes continues to play important role as therapeutic agents. Recent studies have started to explore the human microbiome as a source of drugs.[12] The human body is home to a society of benign, symbiotic, commensal and pathogenic microbes collectively known as the microbiome. These microbes can modulate host brain function and behavior via the gut-brain axis and production of several metabolites such as GABA, glutamate and serotonin.

Dysfunction in the microbiome-derived metabolite signaling can contribute to neurological disorders including AD.[13,14] In summary, the microbiome presents an untapped rich resource for mining novel neuroprotective compounds or live biotherapeutics that will be relevant for AD.

The inventors have developed a high-throughput screening (HTS) assay to rapidly prioritize "single" microbial species for identifying microbiome-based therapeutics for AD using C. elegans whole-animal model system. In the transgenic strains expressing AD-relevant human pathogenic Aβ or tau in all the neurons, it was found that mitochondrial unfolded protein response (as assessed by (UPRmt) reporter construct phsp-6::gfp) was turned on in many tissues, including the gut (FIGS. 11&12). hsp-6 encodes a mitochondrial matrix chaperone HSP70, which is specifically upregulated in response to impaired mitochondrial structure or function[15] and can be assessed using the phsp-6::gfp strain in which the promoter of hsp-6 gene is tagged with GFP. These data are consistent with previous studies that show expression of Aβ in C. elegans results in the accumulation of abnormal mitochondria[16] and muscle-specific expression of A β induced mitochondrial stress genes including hsp-6.[11] Expression of Aβ or tau in the neurons using the neuronal-specific (unc-119) promoter induces mitochondrial stress reporter expression (UPRmt) primarily in the gut (FIGS. 11 & 12), this response is cell-non-autonomous in nature. Similarly, neuron to gut cell-non-autonomous induction of UPRmt has been observed by other labs and proposed to function through neuropeptide and serotonin signaling pathways in C. elegans.[17-19]

Interestingly, modulation of serotonin signaling is considered to be a potential symptomatic treatment for cognitive symptoms in AD.[20,21] To determine whether the activation of UPRmt is a direct consequence of Aβ aggregates, transgenic worms expressing Aβ and phsp-6::gfp reporter were treated with Thioflavin T, which is an amyloid fibril-binding flavonoid shown to reduce Aβ aggregation in vivo and rescue the paralysis phenotype.[22] It was found that in worms treated with Thioflavin T, the induction of UPRmt was reduced, indicating that the induction of UPRmt is directly due to Aβ aggregation. Thus, it is possible to screen for interventions that will reduce the UPRmt induction by modulating the Aβ aggregation or toxicity of Aβ on mitochondria.

Figure 11:
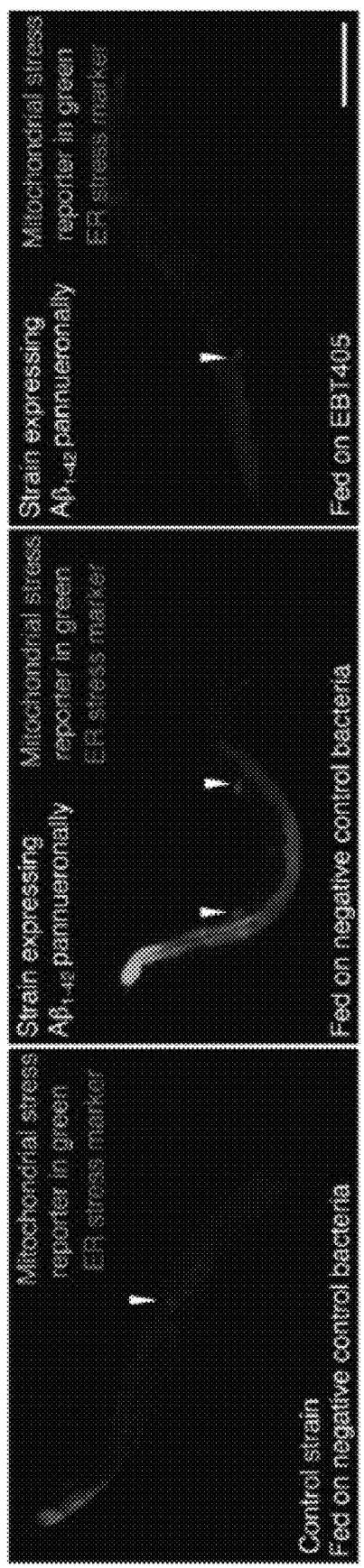
FIG. 11 Panneuronal expression of human $A1\beta 1_{1-42}$ is sufficient to induce UPR$^{mt}$ reporter phsp-6::gfp in the intestine. Representative fluorescence micrographs of strains either not expressing human $A\beta_{1-42}$ (control strain on the left) and strain expressing the human $A\beta_{1-42}$ (Center and right images) fed on either negative control bacteria or *Gluconoacetobacter* EBT405 bacteria. All the strains contain phsp-6::gfp and phsp-4::mcherry reporters. While only basal levels of phsp-6::gfp expression is observed in the control strain (Left image), the GFP is activated in the gut of strain carrying human $A\beta_{1-42}$ (Center image); however, in the strain fed on the *Gluconoacetobacter* EBT405 bacteria, the phsp-6::gfp expression is reduced. The ER unfolded protein response UPR$^{ER}$ reporter phsp-4::mcherry is only weakly activated in the spematheca (white arrowheads). Scale bar on the left image is 200 μM.
Figure 12:
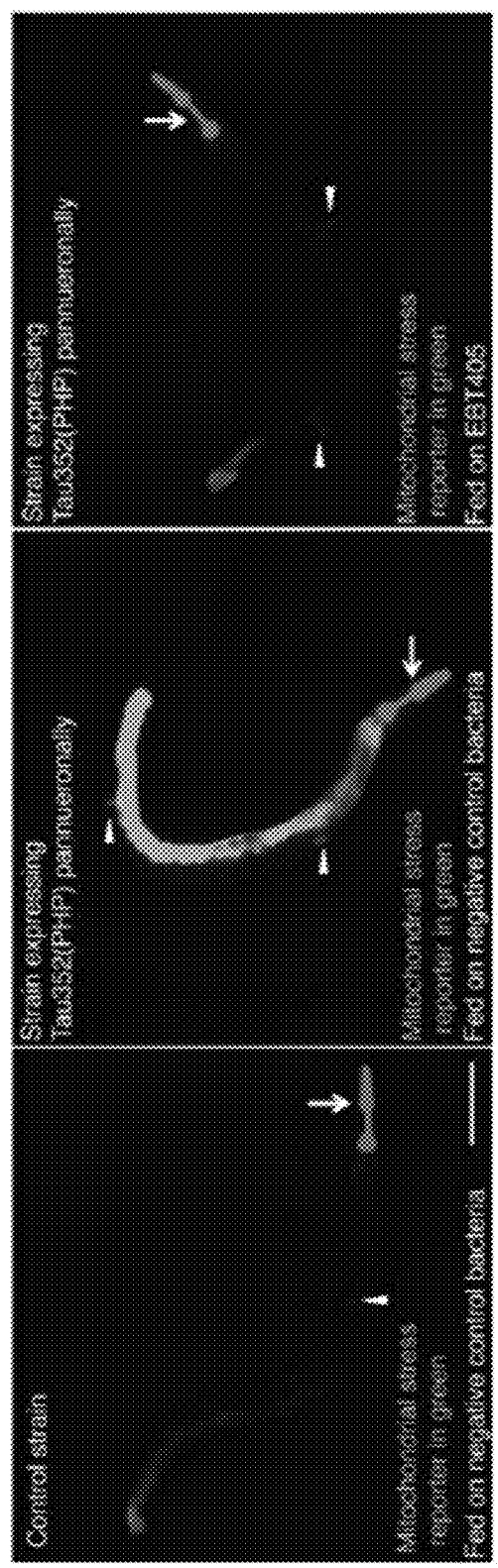
FIG. 12 Panneuronal expression of human aggregative tau mutant is sufficient to induce UPRmt stress reporter phsp-6::gfp in the intestine. Representative fluorescence micrographs of strains either not expressing human tau mutant (control strain on the left) and strain expressing the human tau mutant (Center and right images) fed on either negative control bacteria or EBT405 bacteria. All the strains contain phsp-6::gfp, phsp-4::mcherry reporters and a pharnygeal marker (white arrows), pmyo-2:mcherry. While only basal levels of phsp-6::gfp expression is observed in the control strain (Left image), the GFP is activated in the gut of strain carrying human tau mutant (Center image); however, in the strain fed on the *Gluconoacetobacter* EBT405 bacteria, the phsp-6::gfp expression is reduced. This reduction is specific because the expression of the pharygeal marker is not affected. The UPRER reporter phsp-4::mcherry is only weakly activated in the spematheca (white arrowheads). Scale bar on the left image is 200 μM.
Figure 13:
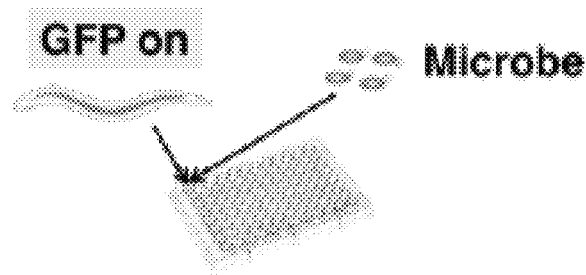
FIG. 13 shows a schematic representation of the HTS strategy.

For the screen, thirty microbial strains including the negative control bacteria E. coli OP50 were grown in appropriate culture media conditions and spotted onto standard nematode growth medium plates. ~30 synchronized L1-larval-stage transgenic worm expressing Aβ 1-42 or tau in the pan-neurons were dropped onto the seeded plates and scored visually after 4 days under a fluorescent microscope for changes in phsp-6::gfp expression (FIG. 13). To synchronize worms, a bleach-prepping method was used, which also created germ-free animals that were fed on monocultures. The inventors screened for changes in the expression of phsp-6::gfp reporter and found that worms fed on Gluconobacter EBT 405 bacteria showed significant reduction in the expression of phsp-6::gfp induced by Aβ1-42 expressing or transgenic tau (FIGS. 11 & 12).

Figure 14:
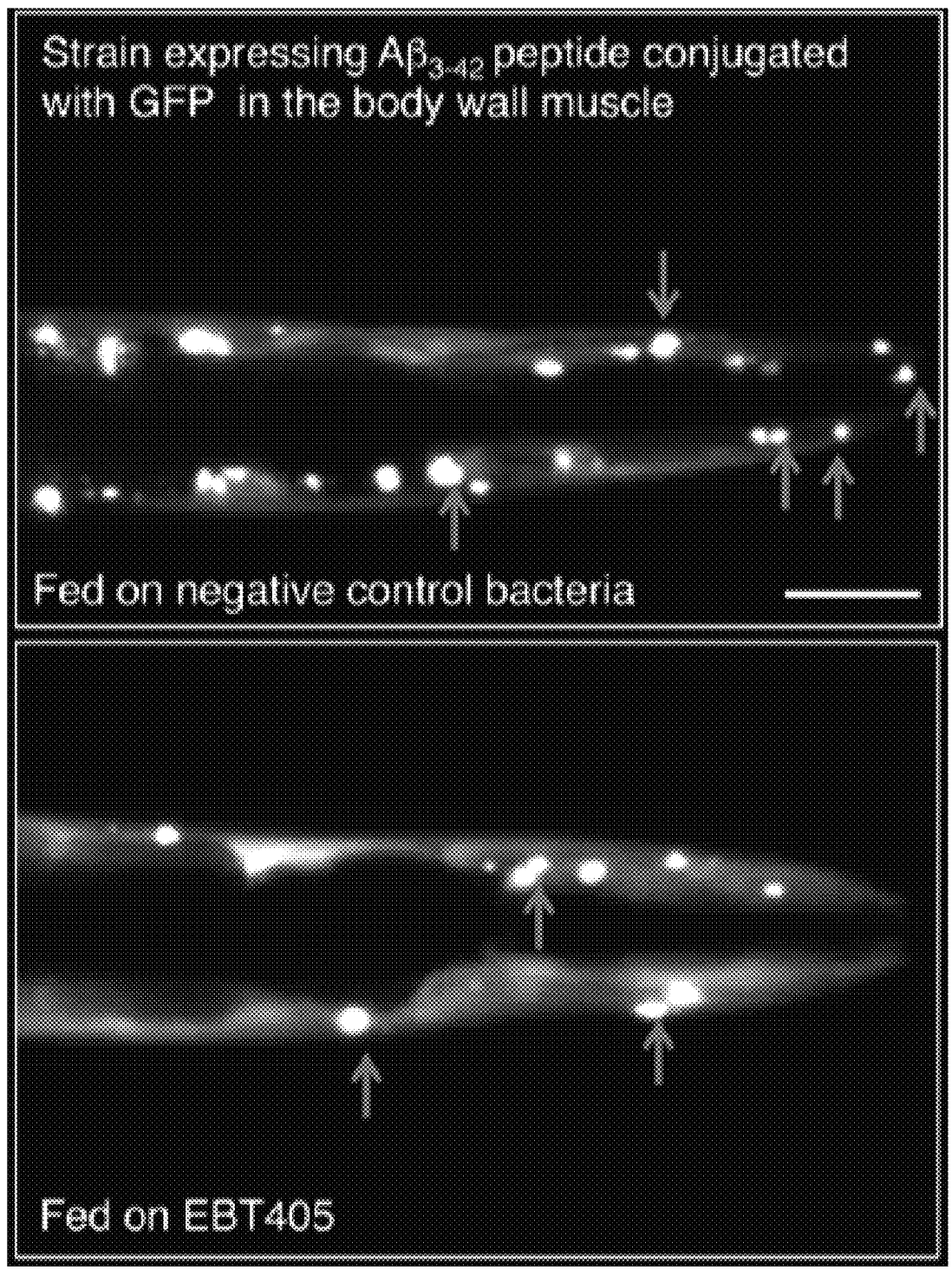
FIG. 14 shows data indicating that EBT 405 feeding reduces $A\beta_{3-42}$ aggregates. Representative fluorescence micrographs of CL2331 strain expressing the $A\beta_{3-42}$ peptide conjugated with GFP fed on negative control bacteria or EBT405 and imaged 60 hours post L1 stage. Arrows indicate amyloid deposits. Scale bar, 200 μM

To evaluate the Aβ aggregation state in vivo, a transgenic strain expressing human Aβ 3-42 conjugated in the body wall muscle[23] was used; EBT405 bacteria were tested on this model and found a significant reduction of A β deposits compared to transgenic worms fed on negative control bacteria (FIG. 14). This strain will be used to test the hits from the HTS screen for reduction of Aβ deposits.

To evaluate the ability of Gluconobacter EBT 405 to suppress Aβ-induced paralysis phenotype, the inventors used a strain that expresses full-length human Aβ1-42 peptide in body wall muscle cells[24]. Shifting L4 or young adult animals from 20° C. to 25° C. causes paralysis in worms fed on the control bacteria while the time of onset of paralysis is significantly delayed in worms fed on Gluconobacter EBT 405.

References for Example 4

1. Masters, C. L. et al. Alzheimer's disease. Nat Rev Dis Primers 1, 15056 (2015).
2. Nelson, P. T. et al. Correlation of Alzheimer disease neuropathologic changes with cognitive status: a review of the literature. J. Neuropathol. Exp. Neurol. 71, 362-381 (2012).
3. Halliwell, B. Oxidative stress and neurodegeneration: where are we now? J Neurochem 97, 1634-1658 (2006).
4. Cheignon, C. et al. Oxidative stress and the amyloid beta peptide in Alzheimer's disease. Redox Biol 14, 450-464 (2018).
5. Müller, W. E., Eckert, A., Kurz, C., Eckert, G. P. & Leuner, K. Mitochondrial dysfunction: common final pathway in brain aging and Alzheimer's disease—therapeutic aspects. Mol. Neurobiol. 41, 159-171 (2010).
6. Moreira, P. I., Carvalho, C., Zhu, X., Smith, M. A. & Perry, G. Mitochondrial dysfunction is a trigger of Alzheimer's disease pathophysiology. Biochim. Biophys. Acta 1802, 2-10 (2010).
7. Link, C. D. *C. elegans* models of age-associated neurodegenerative diseases: lessons from transgenic worm models of Alzheimer's disease. Exp. Gerontol. 41, 1007-1013 (2006).
8. Lublin, A. L. & Link, C. D. Alzheimer's disease drug discovery: in vivo screening using *Caenorhabditis elegans* as a model for β-amyloid peptide-induced toxicity. Drug Discov Today Technol 10, e115-9 (2013).
9. Chen, X., Barclay, J. W., Burgoyne, R. D. & Morgan, A. Using *C. elegans* to discover therapeutic compounds for ageing-associated neurodegenerative diseases. Chem Cent J 9, 65 (2015).
10. Ng, L. F. et al. The mitochondria-targeted antioxidant MitoQ extends lifespan and improves healthspan of a transgenic *Caenorhabditis elegans* model of Alzheimer disease. Free Radic. Biol. Med. 71, 390-401 (2014).
11. Sorrentino, V. et al. Enhancing mitochondrial proteostasis reduces amyloid-β proteotoxicity. Nature 552, 187-193 (2017).
12. Donia, M. S. & Fischbach, M. A. HUMAN MICROBIOTA. Small molecules from the human microbiota. Science 349, 1254766-1254766 (2015).
13. Sharon, G., Sampson, T. R., Geschwind, D. H. & Mazmanian, S. K. The Central Nervous System and the Gut Microbiome. Cell 167, 915-932 (2016).
14. Hill, J. M., Bhattacharjee, S., Pogue, A. I. & Lukiw, W. J. The gastrointestinal tract microbiome and potential link to Alzheimer's disease. Front Neurol 5, 43 (2014).
15. Yoneda, T. et al. Compartment-specific perturbation of protein handling activates genes encoding mitochondrial chaperones. J. Cell. Sci. 117, 4055-4066 (2004).
16. Fonte, V. et al. A glycine zipper motif mediates the formation of toxic β-amyloid oligomers in vitro and in vivo. Mol Neurodegener 6, 61 (2011).
17. Shao, L.-W., Niu, R. & Liu, Y. Neuropeptide signals cell non-autonomous mitochondrial unfolded protein response. Cell Res. 26, 1182-1196 (2016).
18. Durieux, J., Wolff, S. & Dillin, A. The cell-non-autonomous nature of electron transport chain-mediated longevity. Cell 144, 79-91 (2011).
19. Berendzen, K. M. et al. Neuroendocrine Coordination of Mitochondrial Stress Signaling and Proteostasis. Cell 166, 1553-1563.e10 (2016).
20. Ferrero, H., Solas, M., Francis, P. T. & Ramirez, M. J. Serotonin 5-HT6Receptor Antagonists in Alzheimer's Disease: Therapeutic Rationale and Current Development Status. CNS Drugs 31, 19-32 (2017).
21. Claeysen, S., Bockaert, J. & Giannoni, P. Serotonin: A New Hope in Alzheimer's Disease? ACS Chem Neurosci 6, 940-943 (2015).
22. Alavez, S., Vantipalli, M. C., Zucker, D. J. S., Klang, I. M. & Lithgow, G. J. Amyloid-binding compounds maintain protein homeostasis during ageing and extend lifespan. Nature 472, 226-229 (2011).
23. Link, C. D. et al. The beta amyloid peptide can act as a modular aggregation domain. Neurobiol. Dis. 32, 420-425 (2008).
24. McColl, G. et al. Utility of an improved model of amyloid-beta ($A\beta_{1-42}$) toxicity in *Caenorhabditis elegans* for drug screening for Alzheimer's disease. Mol Neurodegener 7, 57 (2012).

The invention claimed is:

1. A method of treating Alzheimer's Disease, the method comprising:
   administering to a subject at risk of or suffering from Alzheimer's Disease, a therapeutically effective amount of a composition, thereby reducing the severity of at least one symptom of Alzheimer's Disease compared to a subject without the administration, and
   wherein the composition comprises:
      a measured amount of a bacterial species that comprises and expresses nucleic acid sequences encoding membrane-bound PQQ-dependent glucose dehydrogenase (mGDH), ubiquinol-cytochrome c reductase iron-sulfur subunit, TonB-dependent receptor, carbon-nitrogen hydrolase, and ubiquinol oxidase subunit II, or an extract or fraction derived therefrom,
      wherein the extract or fraction of the bacterial species comprises membrane-bound PQQ-dependent glucose dehydrogenase (mGDH), ubiquinol-cytochrome c reductase iron-sulfur subunit, TonB-dependent receptor, carbon-nitrogen hydrolase, and ubiquinol oxidase subunit II expressed from the nucleic acid sequences,
      wherein the bacterial species is from the Acetobacteriaceae family.

2. The method of claim 1, wherein the bacterium is *Gluconobacter* spp, *Acetobacter* spp., *Gluconoacaetobacter* spp., *Acidomonas* spp, *Ameyamaea* spp., *Asaia* spp., *Granulibacter* spp., *Kozakia* spp., *Neoasaia* spp., *Neokomagataea* spp., *Saccharibacter* spp., *Swaminathania* spp., or *Tanticharoenia* spp.

3. The method of claim 1, wherein one or more of the nucleic acid sequences are exogenous nucleic acid sequences.

4. The method of claim 1, wherein the composition further comprises one or more added bacterial metabolites selected from the group consisting of gluconic acid, 2-keto-gluconic acid, 5-keto-gluconic acid, and 2,5-diketo-D-gluconic acid.

5. The method of claim 1, wherein the bacterial species expresses and/or produces one or more added bacterial metabolites selected from the group consisting of gluconic acid, 2-keto-gluconic acid, 5-keto-gluconic acid, and 2,5-diketo-D-gluconic acid.

6. The method of claim 1, wherein the composition is formulated as a food, a beverage, a feed composition, a probiotic, a nutritional supplement, or a pharmaceutical composition.

7. The method of claim 1, wherein the composition further comprises a prebiotic.

8. The method of claim 1, wherein the composition further comprises a pharmaceutically acceptable carrier.

9. The method of claim 1, wherein the step of administering comprises orally administering the composition.

10. The method of claim 8, wherein the composition is formulated for oral administration.

11. The method of claim 9, wherein the composition is an enteric-coated formulation.

12. The method of claim 1, wherein the subject is human.

13. The method of claim 1, wherein the administering increases one or more of expression of peroxisome proliferator-activated receptor gamma coactivator 1-α (PGC-1α), mitochondrial transcription factor A (TFAM), AMP-activated protein kinase (AMPK) phosphorylation level, nuclear respiratory factor-2 (Nrf2) protein level, PGC-1α mRNA level, TFAM mRNA level, mitochondrial DNA replication, mitochondrial DNA copy number (mtDNA), and expression of at least one mitochondrial β-oxidation enzyme, compared to a subject without the administration.

14. The method of claim 1, wherein the at least one symptom is selected from the group consisting of reduction in plaques, cognitive decline, confusion, delusion, disorientation, forgetfulness, difficulty concentrating, inability to generate new memories, inability to do simple math, inability to recognize common items, aggression, agitation, irritability, meaningless repetition of own words, personality changes, restlessness, lack of restraint, wandering, anger, apathy, general discontent, loneliness, mood swings, depression, hallucination, paranoia, loss of appetite, inability to combine muscle movements, and jumbled speech.

15. The method of claim 1, wherein the at least one symptom is reduction in plaques.

16. A method of treating Parkinson's Disease, the method comprising:
   administering to a subject at risk of or suffering from Parkinson's Disease, a therapeutically effective amount of a composition, thereby reducing the severity of at least one symptom of Parkinson's Disease compared to a subject without the administration, and
   wherein the composition comprises:
      a measured amount of a bacterial species that comprises and expresses nucleic acid sequences encoding membrane-bound PQQ-dependent glucose dehydrogenase (mGDH), ubiquinol-cytochrome c reductase iron-sulfur subunit, TonB-dependent receptor, carbon-nitrogen hydrolase, and ubiquinol oxidase subunit II, or an extract or fraction derived therefrom,
      wherein the extract or fraction of the bacterial species comprises membrane-bound PQQ-dependent glucose dehydrogenase (mGDH), ubiquinol-cytochrome c reductase iron-sulfur subunit, TonB-dependent receptor, carbon-nitrogen hydrolase, and ubiquinol oxidase subunit II expressed from the nucleic acid sequences, wherein the bacterial species is from the Acetobacteriaceae family.

17. A method of treating Huntington's Disease, the method comprising:
   administering to a subject at risk of or suffering from Huntington's Disease, a therapeutically effective amount of a composition, thereby reducing the severity of at least one symptom of Huntington's Disease compared to a subject without the administration, and
   wherein the composition comprises:
      a measured amount of a bacterial species that comprises and expresses nucleic acid sequences encoding membrane-bound PQQ-dependent glucose dehydrogenase (mGDH), ubiquinol-cytochrome c reductase iron-sulfur subunit, TonB-dependent receptor, carbon-nitrogen hydrolase, and ubiquinol oxidase subunit II, or an extract or fraction derived therefrom,
      wherein the extract or fraction of the bacterial species comprises membrane-bound PQQ-dependent glucose dehydrogenase (mGDH), ubiquinol-cytochrome c reductase iron-sulfur subunit, TonB-dependent receptor, carbon-nitrogen hydrolase, and ubiquinol oxidase subunit II expressed from the nucleic acid sequences,
      wherein the bacterial species is from the Acetobacteriaceae family.

* * * * *